United States Patent
Li et al.

(10) Patent No.: US 12,024,511 B2
(45) Date of Patent: *Jul. 2, 2024

(54) SUBSTITUTED IMIDAZO[1,2-A]PYRIDIN-2-YLAMINE COMPOUNDS, AND PHARMACEUTICAL COMPOSITIONS AND METHODS OF USE THEREOF

(71) Applicant: Shanghai Fudan-Zhangjiang Bio-Pharmaceutical Co., Ltd., Shanghai (CN)

(72) Inventors: Jin Li, Nanjing (CN); Shung Wu, Princeton, NJ (US); Minmin Yang, Nanjing (CN); Sean Chen, Princeton, NJ (US); Wenshan Hao, Parsippany, NJ (US)

(73) Assignee: Shanghai Fudan-Zhangjiang Bio-Pharmaceutical Co., Ltd., Shanghai (CN)

( * ) Notice: Subject to any disclaimer, the term of this patent is extended or adjusted under 35 U.S.C. 154(b) by 363 days.

This patent is subject to a terminal disclaimer.

(21) Appl. No.: 16/984,110

(22) Filed: Aug. 3, 2020

(65) Prior Publication Data

US 2020/0361934 A1    Nov. 19, 2020

Related U.S. Application Data

(63) Continuation of application No. 16/425,761, filed on May 29, 2019, now Pat. No. 10,730,875, which is a continuation of application No. 15/545,276, filed as application No. PCT/CN2016/072341 on Jan. 27, 2016, now abandoned.

(60) Provisional application No. 62/109,028, filed on Jan. 28, 2015.

(51) Int. Cl.
| | | |
|---|---|---|
| *C07D 471/04* | (2006.01) | |
| *A61K 9/00* | (2006.01) | |
| *A61K 9/10* | (2006.01) | |
| *A61K 31/437* | (2006.01) | |
| *A61K 31/4545* | (2006.01) | |
| *A61K 31/496* | (2006.01) | |
| *A61K 31/5377* | (2006.01) | |
| *A61K 31/541* | (2006.01) | |
| *A61K 45/06* | (2006.01) | |
| *A61K 47/10* | (2017.01) | |
| *A61K 47/38* | (2006.01) | |
| *C07D 487/04* | (2006.01) | |

(52) U.S. Cl.
CPC .......... *C07D 471/04* (2013.01); *A61K 9/0019* (2013.01); *A61K 9/0053* (2013.01); *A61K 9/10* (2013.01); *A61K 31/437* (2013.01); *A61K 31/4545* (2013.01); *A61K 31/496* (2013.01); *A61K 31/5377* (2013.01); *A61K 31/541* (2013.01); *A61K 45/06* (2013.01); *A61K 47/10* (2013.01); *A61K 47/38* (2013.01); *C07D 487/04* (2013.01)

(58) Field of Classification Search
CPC .................................................... C07D 471/04
See application file for complete search history.

(56) References Cited

U.S. PATENT DOCUMENTS

| | | |
|---|---|---|
| 7,563,788 B2 | 7/2009 | Sciotti et al. |
| 8,853,240 B2 | 10/2014 | Menet et al. |
| 9,181,234 B2 | 11/2015 | Palmer et al. |
| 2013/0089512 A1 | 4/2013 | Eastwood et al. |
| 2013/0216498 A1 | 8/2013 | Eastwood et al. |

FOREIGN PATENT DOCUMENTS

| | | |
|---|---|---|
| WO | 2011076419 A1 | 6/2011 |
| WO | 2014164409 A1 | 10/2014 |

OTHER PUBLICATIONS

Qiao "Structure-activity relationship study of EphB3 receptor tyrosine kinase inhibitors" Bioorganic & Medicinal Chemistry Letters 2009 19, 6122-6126.*
Berge et al., "Pharmaceutical salts," J. Pharm. Sci. 1977, 66, 1-19.
Clark et al., "Discovery and development of Janus kinase (JAK) inhibitors for inflammatory diseases," J. Med. Chem. 2014, 57, 5023-38.
Darnell et al., "Jak-STAT pathways and transcriptional activation in response to IFNs and other extracellular signaling proteins," Science 1994, 264, 1415-21.

(Continued)

*Primary Examiner* — David K O'Dell

(74) *Attorney, Agent, or Firm* — Lin Yu, Esq.; Juniv LLP

(57) ABSTRACT

Provided herein are substituted imidazo[1,2-a]pyridin-2-ylamine compounds, for example, of formula (A), and pharmaceutical compositions thereof; and methods of their use for treating, preventing, or ameliorating one or more symptoms of a Janus kinase-mediated disease.

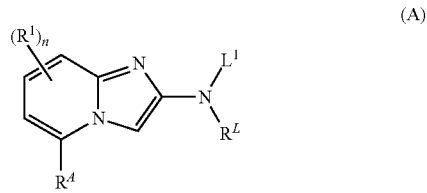

(A)

20 Claims, 3 Drawing Sheets

(56) References Cited

OTHER PUBLICATIONS

Fridman et al., "Selective inhibition of JAK1 and JAK2 is efficacious in rodent models of arthritis: preclinical characterization of INCB028050," J. Immunol. 2010, 184, 5298-307.

Gadina et al., "Signaling by type I and II cytokine receptors: ten years after," Curr. Opin. Immunol. 2001, 13, 363-73.

Hofmann et al., "Cytokines and their role in lymphoid development, differentiation and homeostasis," Curr. Opin. Allergy Clin. Immunol. 2002, 2, 495-506.

Ihle, "Cytokine receptor signaling," Nature 1995, 377, 591-4.

Kawahito et al., "Localization of quantitative trait loci regulating adjuvant-induced arthritis in rats: evidence for genetic factors common to multiple autoimmune diseases," J. Immunol. 1998, 161, 4411-9.

Kliwinski et al., "Prophylactic administration of abatacept prevents disease and bone destruction in a rat model of collagen-induced arthritis," J. Autoimmun. 2005, 25, 165-71.

Leonard et al., "Jaks and STATs: biological implications," Annu. Rev. Immunol. 1998, 16, 293-322.

O'Shea et al., "Back to the future: oral targeted therapy for RA and other autoimmune diseases," Nat. Rev. Rheumatol. 2013, 9, 173-82.

O'Shea et al., "The JAK-STAT pathway: impact on human disease and therapeutic intervention," Annu. Rev. Med. 2015, 66, 311-28.

Quintas-Cardama et al., "Janus kinase inhibitors for the treatment of myeloproliferative neoplasias and beyond," Nat. Rev. Drug Discov. 2011, 10, 127-40.

Rompaey et al., "Preclinical characterization of GLPG0634, a selective inhibitor of JAK1, for the treatment of inflammatory diseases," J. Immunol. 2013, 191, 3568-77.

Starr et al., "5-(2-Pyrimidinyl)-imidazo[1,2-a]pyridines are antibacterial agents targeting the ATPase domains of DNA gyrase and topoisomerase IV," Bioorg. Med. Chem. Lett. 2009, 19, 5302-6.

Vilarino et al., "Mechanisms of Jak/STAT signaling in immunity and disease," J. Immunol. 2015, 194, 21-7.

Young et al., "L-743, 726 (DMP-266): a novel, highly potent nonnucleoside inhibitor of the human immunodeficiency virus type 1 reverse transcriptase," Antimicrob. Agents Chemother. 1995, 39, 2602-5.

\* cited by examiner

SUBSTITUTED IMIDAZO[1,2-A]PYRIDIN-2-YLAMINE COMPOUNDS, AND PHARMACEUTICAL COMPOSITIONS AND METHODS OF USE THEREOF

CROSS REFERENCE TO RELATED APPLICATIONS

This application is a continuation of U.S. application Ser. No. 16/425,761, filed May 29, 2019; which is a continuation of U.S. application Ser. No. 15/545,276, filed Jul. 20, 2017; which is a National Stage of International Application No. PCT/CN2016/072341, filed Jan. 27, 2016; which claims the benefit of U.S. Provisional Application No. 62/109,028, filed Jan. 28, 2015; the disclosure of each of which is incorporated herein by reference in its entirety

FIELD

Provided herein are substituted imidazo[1,2-a]pyridin-2-ylamine compounds, and pharmaceutical compositions thereof; and methods of their use for treating, preventing, or ameliorating one or more symptoms of a Janus kinase-mediated disease.

BACKGROUND

Janus kinase (JAK) signaling pathway, discovered in interferon-induced receptor mediated gene expression, has been shown to be a common signaling pathway used by many cytokines and growth factors. See, e.g., Darnell et al., *Science* 1994, 264, 1415-1421; Ihle, *Nature* 1995, 377, 591-594; Leonard et al., *Annu. Rev. Immunol.* 1998, 16, 293-322. The mammalian JAK family of intracellular tyrosine kinases has four members: Janus kinase 1 (JAK1), Janus kinase 2 (JAK2), Janus kinase 3 (JAK3), and tyrosine kinase 2 (TYK2). JAKs range in size from 120 to 140 kDa and contain seven conserved JAK homology (JH) domains, which define this kinase super family. See, e.g., Gadina et al., *Curr. Opin. Immunol.* 2001, 13, 363-373.

Binding of a cytokine to a cell surface receptor results in receptor dimerization and subsequent activation/phosphorylation of JAK tyrosine kinases that are constitutively associated with the receptor. Specific tyrosine residues on the receptor are then phosphorylated by activated JAKs and serve as docking sites for a family of latent cytoplasmic transcription factors known as Signal Transducers and Activators of Transcription (STATS). STATS are phosphorylated by JAKs, dimerize, and then translocate to the nucleus where they bind specific DNA elements and activate gene transcription. See, e.g., Villarino et al., *J. Immunol.* 2015, 194, 21-27.

The JAKs are activated by a wide range of cytokines that play essential roles in immune function, inflammation, and hematopoiesis. See, e.g., Hofmann et al., *Curr. Opin. Allergy Clin. Immunol.* 2002, 2, 495-506; O'Shea et al., *Annu. Rev. Med.* 2015, 66, 311-328. JAK and JAK3 can be activated by a member of the γ common (γc) subfamily, namely, interleukins IL-2, IL-4, IL-7, IL-9, IL-15, and IL-21; however, these cytokines never activate JAK2 or TYK2. The importance of these cytokines to the immune system is highlighted by observation of severe combined immunodeficiency when loss-of-function mutations occur in these cytokines or in JAK3. Another large subfamily of cytokines that shares the glycoprotein 130 (gp130) signal transducing subunit includes IL-6, IL-11, IL-27, and several other cytokines. The signaling of these cytokines always involves JAK activation, and JAK2 and TYK2 are also consistently engaged. IL-6 has been implicated in immune response, and excessive stimulation of this pathway is linked to various autoimmune and chronic inflammatory conditions. Numerous homodimeric receptors for erythropoietin (EPO), prolactin, thrombopoietin, and growth hormone are known to activate JAKs. The EPO pathway activates JAK2 exclusively and is essential to red blood cell formation or erythropoiesis.

Each JAK isoform can be employed by multiple cytokine pathways and by extension, the biological activities of many cytokines can be modulated by inhibition of a single or multiple JAKs. See, e.g., O'Shea et al., *Annu. Rev. Med.* 2015, 66, 311-328. Inhibition of JAK can be useful for preventing, inhibiting, or treating the progression or onset of various diseases and disorders, including hyper-proliferative disorders and cancer such as leukemia and lymphomas, immunological and inflammatory disorders such as transplant rejection, asthma, chronic obstructive pulmonary disease, allergies, rheumatoid arthritis, amyotrophic lateral sclerosis, and multiple sclerosis. See, e.g., Quintás-Cardama et al., *Nat. Rev. Drug Discov.* 2011, 10, 127-140; O'Shea et al., *Nat. Rev. Rheumatol.* 2013, 9, 173-182; O'Shea et al., *Annu. Rev. Med.* 2015, 66, 311-328.

SUMMARY OF THE DISCLOSURE

Provided herein is a compound of formula (A):

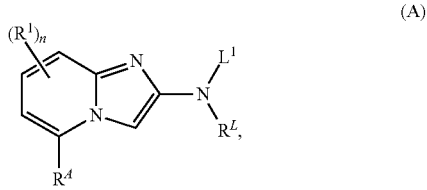

(A)

or a single enantiomer, a racemic mixture, a mixture of diastereomers, or an isotopic variant thereof; or a pharmaceutically acceptable salt, solvate, or prodrug thereof; wherein:

$L^1$ is hydrogen or —C(O)$R^2$.

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^2$ is $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;

$R^A$ is $C_3$-$C_{10}$ cycloalkyl, $C_6$-$C_{10}$ aryl, heteroaryl, or heterocyclyl;

$R^L$ is hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;

each $R^{1a}$, $R^{1b}$, $R^{1c}$, and $R^{1d}$ is independently hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl; and n is an integer of 0, 1, 2, 3, or 4;

wherein each alkyl, alkenyl, alkynyl, cycloalkyl, aryl, heteroaryl, and heterocyclyl is optionally substituted with one or more, in one embodiment, one, two, three, or four, substituents Q, where each Q is independently selected from (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OP(O)(O$R^a$)$_2$, —OS(O)$R^a$, —OS(O)$_2 R^a$, —OS(O)N$R^b R^c$, —S(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; and (c) —C(O)$R^f$, —C(O)O$R^f$, —C(O)N$R^g R^h$, —C(N$R^f$)N$R^g R^h$, —O$R^f$, —OC(O)$R^f$, —OC(O)O$R^f$, —OC(O)N$R^g R^h$, —OC(=N$R^f$)N$R^g R^h$, —OS(O)$R^f$, —OS(O)$_2 R^f$, —OS(O)N$R^g R^h$, —OS(O)$_2$N$R^g R^h$, —N$R^g R^h$, —N$R^f$C(O)$R^k$, —N$R^f$C(O)O$R^k$, —N$R^f$C(O)N$R^g R^h$, —N$R^f$C(=N$R^k$)N$R^g R^h$, —N$R^f$S(O)$R^k$, —N$R^f$S(O)$_2 R^k$, —N$R^f$S(O)N$R^g R^h$, —N$R^f$S(O)$_2$N$R^g R^h$, —S$R^f$, —S(O)$R^f$, —S(O)$_2 R^f$, —S(O)N$R^g R^h$, and —S(O)$_2$N$R^g R^h$; wherein each $R^f$, $R^g$, $R^h$, and $R^k$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; or (iii) $R^g$ and $R^h$ together with the N atom to which they are attached form heterocyclyl.

Also provided herein are imidazo[1,2-a]pyridin-2-ylamine compounds with a structure represented by formula (I):

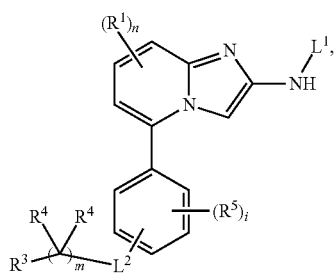

(I)

and pharmaceutically acceptable solvates, salts, or prodrugs thereof, wherein $L^1$, $L^2$, m, n, i, $R^1$, $R^3$, $R^4$, and $R^5$ are as defined below.

Furthermore, provided herein are pharmaceutical compositions comprising any of the compounds provided herein and one or more pharmaceutically acceptable carriers.

The compounds and compositions provided herein are useful for treating diseases, disorders, or conditions associated with JAK activities. Thus, provided herein are methods for treatment and/or prevention of JAK-mediated diseases or disorders, including but not limited to, rheumatoid arthritis, asthma, psoriasis, juvenile idiopathic arthritis, colitis, inflammatory bowel diseases, lupus, alopecia, dry eyes, diseases associated with hypersecretion of IL6, organ transplant rejection, and proliferative diseases.

The compounds provided herein can be used alone or in combination with other compounds disclosed herein, or in combination with one or more other agent(s). Thus, provided herein is a method for preventing, inhibiting, or treating the diseases as described herein, wherein a therapeutically effective amount of a combination of a compound provided herein (e.g., a compound of any one of formulae (A) to (I)) and another compound of provided herein (e.g., a compound of any one of formulae (A) to (I)) and/or at least one other type of therapeutic agents, is administered to a mammalian, i.e., human, patient in need of treatment.

Provided herein is a method for modulating the activity of a tyrosine kinase, in one embodiment, a Janus kinase, comprising contacting the Janus kinase with a compound provided herein.

Provided herein is a method for modulating the activity of a tyrosine kinase, in one embodiment, a Janus kinase, in a subject, comprising administering to the subject a compound provided herein.

Provided herein are methods of synthesizing the compounds disclosed herein.

Embodiment 1

Provided herein is a compound of formula (I):

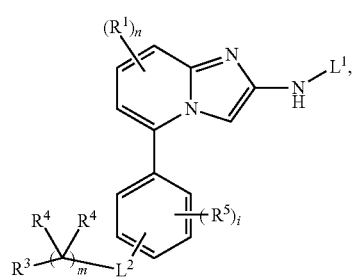

(I)

or a pharmaceutically acceptable salt, solvate, or prodrug thereof, wherein:

$L^1$ is selected from hydrogen and —C(O)$R^2$;

$L^2$ is selected from a single bond, —O—, —N$R^6$—, —C(O)—, —C(O)O—, —OC(O)—, —CON$R^6$—, —N$R^6$CO—, —S(O)$_2$—, —N$R^6$SO$_2$—, and —S(O)$_2$N$R^6$—;

m is 0 or integer selected from 1 to 6;

n is 1, 2, or 3;

i is 1, 2, 3, or 4;

$R^1$ at each occurrence is independently selected from hydrogen, halogen, alkyl, alkenyl, alkynyl, cyano, hydroxy, nitro, acyl, thio, thioalkoxy, thioaryloxy, thio-heteroaryloxy, acylamino, alkoxy, amino, alkylamino, arylamino, heteroarylamino, amido, alkylsulfinyl, alkylsulfonyl, aminosulfonyl, sulfonic acid, sulfonic acid ester, carboxyl, cycloalkyl, cycloalkylalkyl, heterocyclyl, heterocyclylalkyl, aryl, arylalkyl, heteroaryl, and heteroarylalkyl;

R$^2$ is selected from substituted or unsubstituted alkyl, substituted or unsubstituted cycloalkyl, and substituted or unsubstituted heterocyclyl;

R$^3$ is selected from hydrogen, alkyl, alkenyl, alkynyl, aryl, arylalkyl, cycloalkyl, cycloalkylalkyl, heteroaryl, heteroarylalkyl, heterocyclyl, heterocyclylalkyl, alkoxy, aryloxy, heteroaryloxy, alkylthio, arylthio, heteroarylthio, cyano, hydroxy, —OR$^7$, —N(R$^6$)$_2$, —COR$^7$, and —CON(R$^6$)$_2$;

R$^4$ at each occurrence is independently selected from hydrogen, hydroxyl, halogen, alkyl, alkenyl, alkynyl, acyl, acylamino, carboxy, cyano, amido, amino, alkylamino, arylamino, heteroarylamino, alkoxy, aryloxy, heteroaryloxy, cycloalkyl, cycloalkylalkyl, heterocyclyl, aryl, and heteroaryl, where permitted optionally substituted with 1 to 4 R$^8$; or alternatively two R$^4$'s taken together form a 3- to 9-member ring, which may optionally contain 1-4 heteroatoms independently selected from N, O, and S, and may be optionally substituted with 1-5 R$^8$;

R$^5$ at each occurrence is independently selected from hydrogen, halogen, alkyl, alkenyl, alkynyl, cyano, hydroxy, nitro, acyl, thio, thioalkoxy, thioaryloxy, thio-heteroaryloxy, acylamino, alkoxy, amino, alkylamino, arylamino, heteroarylamino, amido, sulfinyl, sulfonyl, aminosulfonyl, sulfonic acid, sulfonic acid ester, carboxy, cycloalkyl, cycloalkylalkyl, heterocyclyl, heterocyclylalkyl, aryl, arylalkyl, heteroaryl, and heteroarylalkyl;

R$^6$ at each occurrence is independently selected from H, alkyl, alkenyl, alkynyl, cycloalkyl, heterocyclyl, aryl, and heteroaryl, or alternatively two R$^6$'s taken together form a 3- to 9-member ring, which may optionally contain 1-4 heteroatoms independently selected from N, O, and S and may be optionally substituted with 1-5 R$^8$;

R$^7$ is selected from cycloalkyl, heterocyclyl, aryl, and heteroaryl;

R$^8$, at each occurrence, is independently selected from alkyl, alkenyl, alkynyl, haloalkyl, acyl, cycloalkyl, cycloalkylalkyl, heterocyclyl, heterocyclylalkyl, aryl, arylalkyl, heteroaryl, heteroarylalkyl, halogen, amino, cyano, nitro, carboxy, —C(=O)OR$^9$, -trifluoromethoxy, hydroxy, thiol, —OR$^9$, —SR$^9$, —C(=O)NR$^a$R$^b$, —NR$^a$R$^b$, —S(O)$_2$NR$^a$R$^b$, —S(O)$_2$R$^9$, —NR$^a$C(=O)R$^9$, and —OC(=O)R$^9$;

R$^9$ at each occurrence is independently hydrogen, C$_1$-C$_6$ alkyl, cycloalkyl, heterocyclyl, aryl, or heteroaryl; and R$^a$ and R$^b$ are each independently hydrogen, C$_1$-C$_6$ alkyl, or C$_3$-C$_6$ cycloalkyl, or alternatively R$^a$ and R$^b$ taken together form an optionally substituted 3-6 member ring, which may optionally comprise one or two heteroatoms independently selected from N, O, and S.

Embodiment 2

In the compound of embodiment 1, L$^2$ is —CH$_2$— or —C(O)—.

Embodiment 3

In the compound of embodiment 1 or 2, R$^3$ is an optionally substituted cycloalkyl or heterocyclyl.

Embodiment 4

In the compound of embodiment 3, R$^3$ is an optionally substituted 5- or 6-membered heterocyclyl.

Embodiment 5

In the compound of embodiment 4, R$^3$ is selected from the group consisting of:

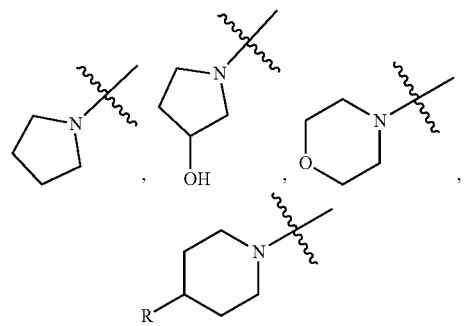

(R=H, lower alkyl, or —CN),

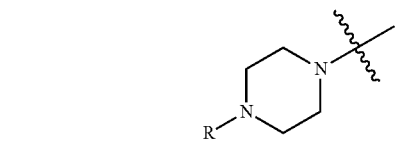

(R=H or lower alkyl),

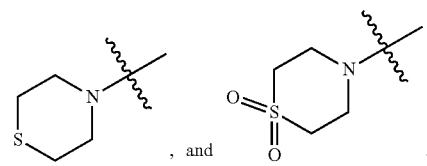

, and .

Embodiment 6

In the compound of embodiment 1, L$^2$ is —O— and R$^3$ is lower alkyl.

Embodiment 7

In the compound of embodiment 1, L$^1$ is H.

Embodiment 8

In the compound of embodiment 1, L$^2$ is —CH$_2$— and R$^3$ is —CN.

Embodiment 9

In the compound of any one of embodiments 1 to 8, R$^2$ is C$_1$-C$_6$ alkyl or C$_3$-C$_6$ cycloalkyl, wherein any said alkyl, cycloalkyl, are each optionally substituted by one to five substituents independently selected from halogen, hydroxyl, amino, $C_1$-$C_4$ alkyl, $C_1$-$C_4$ alkoxy, $C_1$-$C_4$ haloalkyl, and cyano.

Embodiment 10

In the compound of any one of embodiments 1 to 9, $R^1$ is hydrogen, halogen, $C_1$-$C_6$ alkyl, $C_1$-$C_6$ haloalkyl, hydroxyl, amino, $C_1$-$C_6$ alkylamino, di-($C_1$-$C_6$ alkyl)amino, $C_1$-$C_6$ alkoxy, $C_1$-$C_6$ haloalkoxy, nitro, and cyano.

Embodiment 11

In the compound of any one of embodiments 1 to 10, $R^5$ is selected from hydrogen, halogen, $C_1$-$C_6$ alkyl, $C_1$-$C_6$ haloalkyl, hydroxyl, amino, $C_1$-$C_6$ alkylamino, di-($C_1$-$C_6$ alkyl)amino, $C_1$-$C_6$ alkoxy, $C_1$-$C_6$ haloalkoxy, nitro, and cyano.

Embodiment 12

In the compound of any one of embodiments 1 to 11, m=0.

Embodiment 13

In the compound of any one of embodiments 1 to 11, m=1, and $R^4$ at each occurrence is independently selected from hydrogen, hydroxyl, halogen, alkyl, alkenyl, alkynyl, acyl, acyl amino, carboxy, cyano, amido, amino, alkylamino, arylamino, heteroarylamino, alkoxy, aryloxy, heteroaryloxy, cycloalkyl, cycloalkylalkyl, heterocyclyl, aryl, and heteroaryl, or alternatively two $R^4$'s taken together form a 3- to 6-member ring, which may optionally contain 1 to 3 heteroatoms independently selected from N, O, and S, and may be optionally substituted with 1 to 3 $R^8$.

Embodiment 14

Provided herein is a compound selected from the group consisting of:

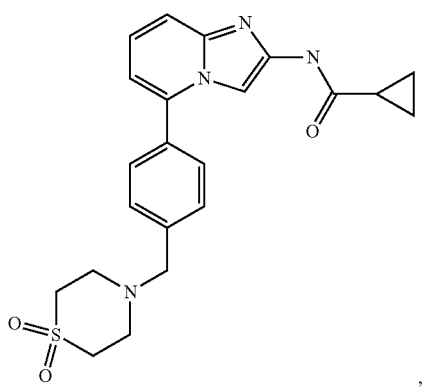

-continued

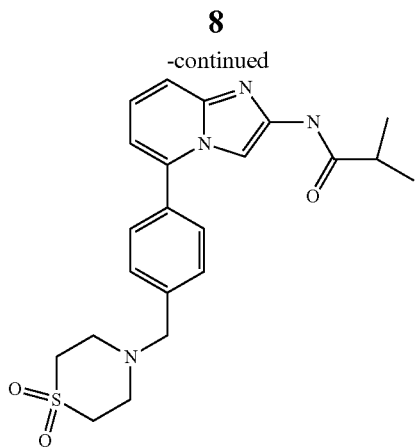

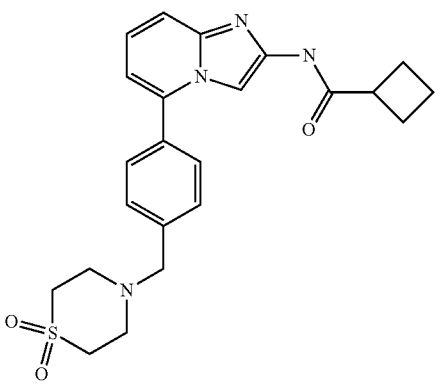

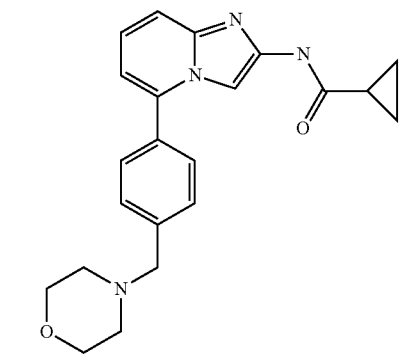

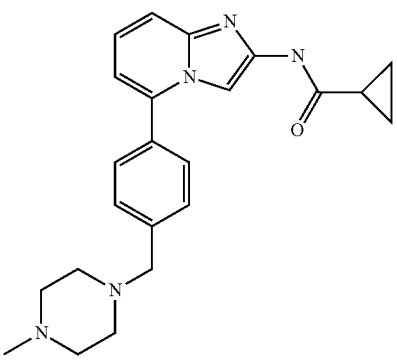

9
-continued
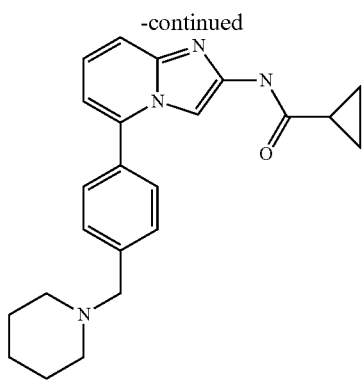
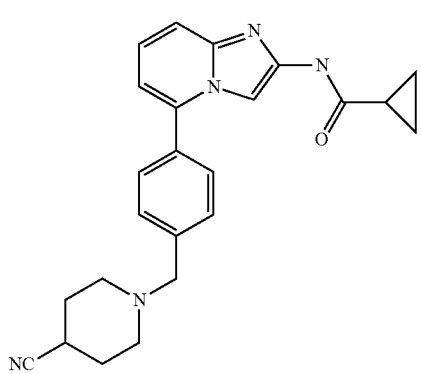
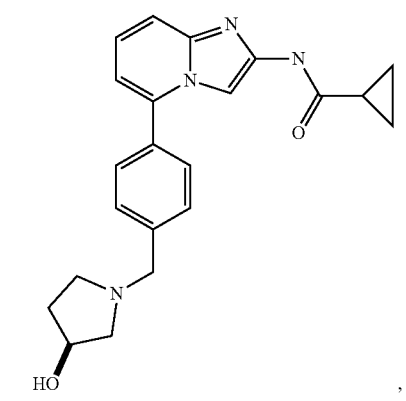
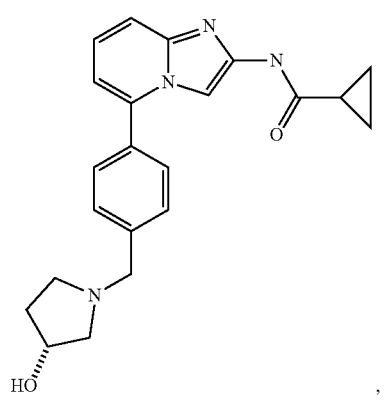
10
-continued
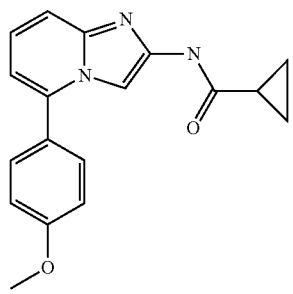
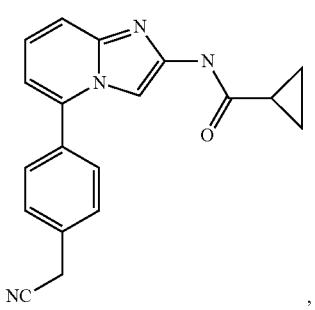
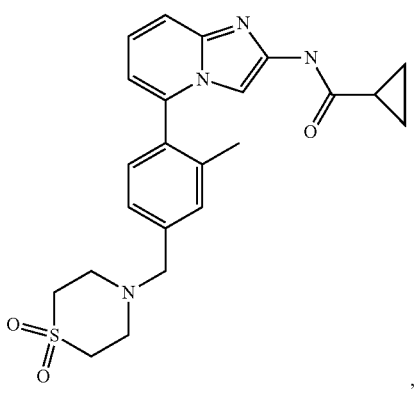
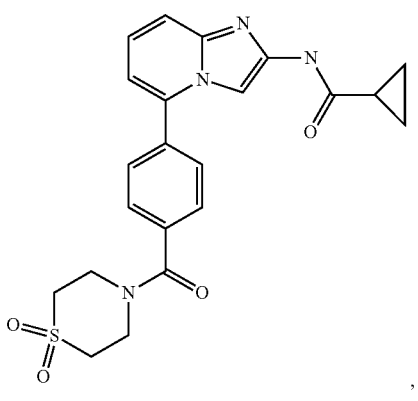

-continued

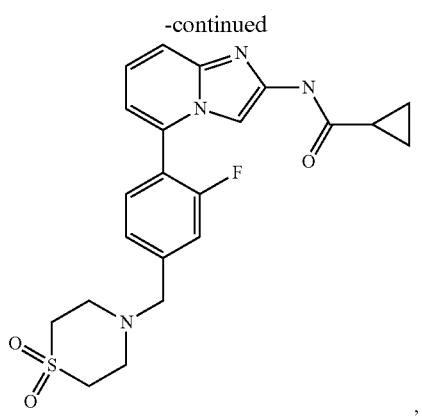

,

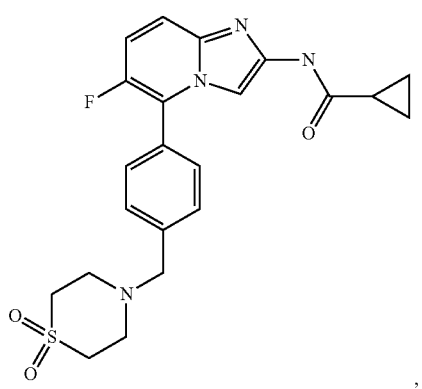

,

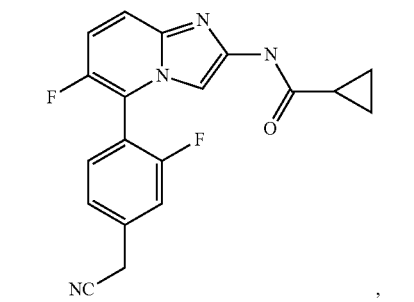

,

-continued

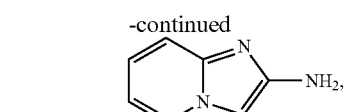

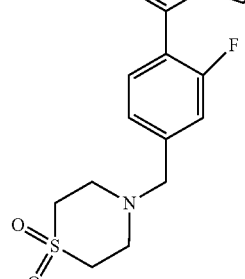

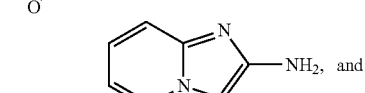

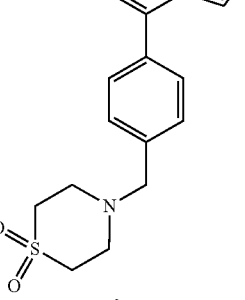

or a pharmaceutically acceptable salt, solvate, or prodrug thereof.

Embodiment 15

Provided herein is a composition comprising a compound according to any one of embodiments 1 to 14, or a pharmaceutically acceptable salt, solvate, or prodrug thereof, and a pharmaceutically acceptable carrier, adjuvant, diluent, or vehicle.

Embodiment 16

The composition of embodiment 15 further comprises a second therapeutic agent.

Embodiment 17

In the composition of embodiment 16, said second therapeutic agent is a different JAK inhibitor.

Embodiment 18

Provided herein is a method of preventing or treating a disease or disorder associated with a Janus kinase (JAK)

activity, comprising administration of a therapeutically effective amount of a compound according to any one of embodiments 1 to 14, or a pharmaceutically acceptable salt, solvate, or prodrug thereof, to a subject in need thereof.

Embodiment 19

In the method of embodiment 18, said disease or disorder is a disease or disorder mediated by Janus kinase (JAK) activity.

Embodiment 20

In the method of embodiment 19, said JAK is selected from the group consisting of JAK1, JAK2, JAK3, and TYK2.

Embodiment 21

In the method of any one of embodiments 18 to 20, said disease or disorder is selected from the group consisting of rheumatoid arthritis, asthma, psoriasis, juvenile idiopathic arthritis, Crohn's diseases, ulcerative colitis, inflammatory bowel diseases, lupus, alopecia, dry eyes, diseases associated with hypersecretion of IL6, organ transplant rejection, and proliferative diseases.

Embodiment 22

Provided herein is a method of inhibiting a JAK activity in a subject, comprising contacting a biological sample of said subject with a compound according to any one of embodiments 1 to 14, and measuring the inhibiting effect.

Embodiment 23

Provided herein is use of a compound according to any one of embodiments 1 to 14, or a pharmaceutically acceptable salt, solvate, or prodrug thereof, or a composition of any one of embodiments 15 to 17, in the manufacture of a medicament for treatment of a disease or disorder associated with a JAK activity.

DETAILED DESCRIPTION

Figure 1:
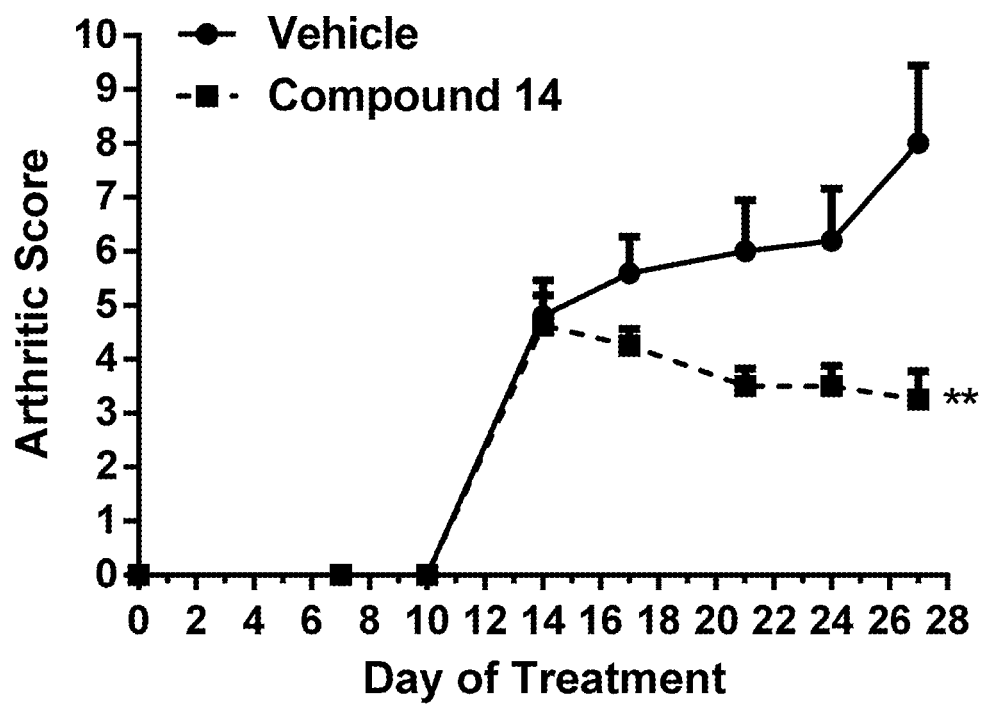
FIG. 1 shows the effect of compound 14 on the arthritic scores of rats in a collagen-induced arthritis model, where the sign "**" indicates p<0.01.

In one embodiment, provided herein is a compound of formula (A):

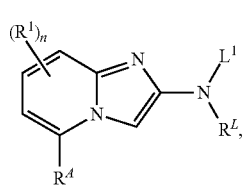

or a single enantiomer, a racemic mixture, a mixture of diastereomers, or an isotopic variant thereof; or a pharmaceutically acceptable salt, solvate, or prodrug thereof;

wherein:

$L^1$ is hydrogen or —C(O)R$^2$;

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^2$ is $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;

$R^A$ is $C_3$-$C_{10}$ cycloalkyl, $C_6$-$C_{10}$ aryl, heteroaryl, or heterocyclyl;

$R^L$ is hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;

each $R^{1a}$, $R^{1b}$, $R^{1c}$, and $R^{1d}$ is independently hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl; and n is an integer of 0, 1, 2, 3, or 4;

wherein each alkyl, alkenyl, alkynyl, cycloalkyl, aryl, heteroaryl, and heterocyclyl is optionally substituted with one or more, in one embodiment, one, two, three, or four, substituents Q, where each Q is independently selected from (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OP(O)(OR$^a$)$_2$, —OS(O)R$^a$, —OS(O)$_2$R$^a$, —OS(O)NR$^b$R$^c$, —S(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from the group consisting of (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; and (c) —C(O)R$^f$, —C(O)OR$^f$, —C(O)NR$^g$R$^h$, —C(NR$^f$)NR$^g$R$^h$, —OR$^f$, —OC(O)R$^f$, —OC(O)OR$^f$, —OC(O)NR$^g$R$^h$, —OC(=NR$^f$)NR$^g$R$^h$, —OS(O)R$^f$, —OS(O)$_2$R$^f$, —OS(O)NR$^g$R$^h$, —OS(O)$_2$NR$^g$R$^h$, —NR$^g$R$^h$, —NR$^f$C(O)R$^k$, —NR$^f$C(O)OR$^k$, —NR$^f$C(O)NR$^g$R$^h$, —NR$^f$C(=NR$^k$)NR$^g$R$^h$, —NR$^f$S(O)R$^k$, —NR$^f$S(O)$_2$R$^k$, —NR$^f$S(O)NR$^g$R$^h$, —NR$^f$S(O)$_2$NR$^g$R$^h$, —SR$^f$, —S(O)R$^f$, —S(O)$_2$R$^f$, —S(O)NR$^g$R$^h$, and —S(O)$_2$NR$^g$R$^h$; wherein each R$^f$, R$^g$, R$^h$, and R$^k$ is independently (i) hydrogen; (ii) C$_1$-C$_8$ alkyl, C$_2$-C$_8$ alkenyl, C$_2$-C$_8$ alkynyl, C$_3$-C$_{10}$ cycloalkyl, C$_6$-C$_{10}$ aryl, heteroaryl, and heterocyclyl; or (iii) R$^g$ and R$^h$ together with the N atom to which they are attached form heterocyclyl.

In another embodiment, provided herein is a compound of formula (I):

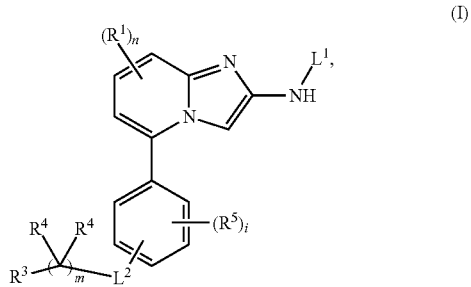

or a pharmaceutically acceptable salt, solvate, or prodrug thereof, wherein:

L$^1$ is selected from hydrogen and —C(O)R$^2$;

L$^2$ is selected from a single bond, —O—, —NR$^6$—, —C(O)—, —C(O)O—, —OC(O)—, —CONR$^6$—, —NR$^6$CO—, —S(O)$_2$—, —NR$^6$SO$_2$—, and —S(O)$_2$NR$^6$—;

m is 0 or an integer selected from 1 to 6;

n is an integer of 0, 1, 2, or 3;

i is an integer of 0, 1, 2, 3, or 4;

R$^1$ at each occurrence is independently selected from halogen, alkyl, alkenyl, alkynyl, cyano, hydroxyl, nitro, acyl, thio, thioalkoxy, thioaryloxy, thioheteroaryloxy, acylamino, alkoxy, amino, alkylamino, arylamino, heteroarylamino, amido, alkylsulfinyl, alkylsulfonyl, aminosulfonyl, sulfonyl, carboxy, cycloalkyl, cycloalkylalkyl, heterocyclyl, heterocyclylalkyl, aryl, arylalkyl, heteroaryl, and heteroarylalkyl;

R$^2$ is selected from substituted or unsubstituted alkyl, substituted or unsubstituted cycloalkyl, and substituted or unsubstituted heterocyclyl;

R$^3$ is selected from hydrogen, alkyl, alkenyl, alkynyl, aryl, arylalkyl, cycloalkyl, cycloalkylalkyl, heteroaryl, heteroarylalkyl, heterocyclyl, heterocyclylalkyl, alkoxy, aryloxy, heteroaryloxy, alkylthio, arylthio, heteroarylthio, cyano, hydroxy, —OR$^7$, —N(R$^6$)$_2$, —COR$^7$, and —CON(R$^6$)$_2$;

R$^4$ at each occurrence is independently selected from hydrogen, hydroxyl, halogen, alkyl, alkenyl, alkynyl, acyl, acyl amino, carboxy, cyano, amido, amino, alkylamino, arylamino, heteroarylamino, alkoxy, aryloxy, heteroaryloxy, cycloalkyl, cycloalkylalkyl, heterocyclyl, aryl, and heteroaryl, where permitted optionally substituted with 1 to 4 R$^8$; or alternatively two R$^4$'s taken together form a 3- to 9-member ring, which optionally contains 1-4 heteroatoms independently selected from N, O, and S, and is optionally substituted with 1-5 R$^8$;

R$^5$ at each occurrence is independently selected from halogen, alkyl, alkenyl, alkynyl, cyano, hydroxyl, nitro, acyl, thio, thioalkoxy, thioaryloxy, thioheteroaryloxy, acylamino, alkoxy, amino, alkylamino, arylamino, heteroarylamino, amido, sulfinyl, sulfonyl, aminosulfonyl, sulfonyl, carboxy, cycloalkyl, cycloalkylalkyl, heterocyclyl, heterocyclylalkyl, aryl, arylalkyl, heteroaryl, and heteroarylalkyl;

R$^6$ at each occurrence is independently selected from hydrogen, alkyl, alkenyl, alkynyl, cycloalkyl, heterocyclyl, aryl, and heteroaryl; or alternatively two R$^6$'s taken together form a 3- to 9-member ring, which optionally contains 1-4 heteroatoms independently selected from N, O, and S and is optionally substituted with 1-5 R$^8$;

R$^7$ is selected from cycloalkyl, heterocyclyl, aryl, and heteroaryl;

R$^8$ at each occurrence is independently selected from alkyl, alkenyl, alkynyl, haloalkyl, acyl, cycloalkyl, cycloalkylalkyl, heterocyclyl, heterocyclylalkyl, aryl, arylalkyl, heteroaryl, heteroarylalkyl, halogen, amino, cyano, nitro, carboxy, —C(=O)OR$^9$, trifluoromethoxy, hydroxyl, thiol, —OR$^9$, —SR$^9$, —C(=O)NR$^a$R$^b$, —NR$^a$R$^b$, —S(O)$_2$NR$^a$R$^b$, —S(O)$_2$R$^9$, —NR$^a$C(=O)R$^9$, and —OC(=O)R$^9$;

R$^9$ at each occurrence is independently hydrogen, C$_1$-C$_6$ alkyl, cycloalkyl, heterocyclyl, aryl, or heteroaryl; and R$^a$ and R$^b$ are each independently hydrogen, C$_1$-C$_6$ alkyl, or C$_3$-C$_6$ cycloalkyl; or alternatively R$^a$ and R$^b$ taken together form an optionally substituted 3-6 member ring, which optionally comprises one or two heteroatoms independently selected from N, O, and S.

In yet another embodiment, provided herein are pharmaceutical compositions comprising a therapeutically effective amount of a compound provided herein, alone or, optionally, in combination with a pharmaceutically acceptable carrier and/or one or more other agent(s).

In yet another embodiment, provided herein are methods of inhibiting the activity of the enzyme Janus kinase in a subject, comprising administering to the subject a compound provided herein, alone or optionally, in combination with one or more other compound(s) provided herein and/or at least one other type of therapeutic agents. In one embodiment, the subject is a mammalian animal; in another embodiment, the subject is a human; and in yet another embodiment, the subject is a human patient having a disease or disorder related to activity of JAK in need of treatment.

Examples of diseases or disorders associated with the activity of the enzyme Janus kinase that can be prevented, inhibited, or treated according to the present disclosure include, but are not limited to, diseases involving in cartilage degradation, bone and/or joint degradation, for example, osteoarthritis; and/or condition involving inflammation or immune response, such as Crohn's diseases, rheumatoid arthritis, asthma rhinitis, psoriasis, juvenile idiopathic arthritis, ulcerative colitis, inflammatory bowel diseases, lupus, diseases or conditions associated with hypersecretion of IL6, and transplantation rejection, such as organ transplant rejection. Inhibitors of JAK can also be used for treatment of proliferative diseases, especially leukemia and a solid tumor.

In one embodiment, provided herein is a method for preventing, inhibiting, or treating the progression or onset of osteoarthritis, Crohn's disease, rheumatoid arthritis, psoriatic arthritis, asthma, psoriasis, juvenile idiopathic arthritis, colitis, an inflammatory bowel disease, lupus, alopecia, dry eyes, a disease or condition associated with hypersecretion of IL6, organ transplant rejection, or a proliferative disease, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In another embodiment, provided herein is a method for preventing, inhibiting, or treating the progression or onset of osteoarthritis, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of Crohn's disease, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein a method for preventing, inhibiting, or treating the progression or onset of rheumatoid arthritis, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of psoriatic arthritis, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of asthma, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of psoriasis, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of juvenile idiopathic arthritis, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of ulcerative colitis, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of an inflammatory bowel disease, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of lupus, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of organ transplant rejection, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of alopecia, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In yet another embodiment, provided herein is a method for preventing, inhibiting, or treating the progression or onset of dry eyes, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

In still another embodiment, provided herein is a method for preventing, inhibiting, or treating the progression or onset of a proliferative disease, comprising administering to a mammalian patient, for example, a human patient, in need of prevention, inhibition, or treatment a therapeutically effective amount of a compound provided herein, alone or, optionally, in combination with one or more other compound(s) provided herein and/or at least one other type of therapeutic agents.

Definitions

To facilitate understanding of the disclosure set forth herein, a number of terms are defined below.

Generally, the nomenclature used herein and the laboratory procedures in biology, biochemistry, medicinal chemistry, organic chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, and mouse. The terms "subject" and "patient" are used interchangeably herein in reference, for example, to a mammalian subject, such as a human subject, in one embodiment, a human.

The term "$IC_{50}$" or "$EC_{50}$" refers an amount, concentration, or dosage of a compound that is required for 50% inhibition of a maximal response in an assay that measures such a response.

The term "$CC_{50}$" refers an amount, concentration, or dosage of a compound that results in 50% reduction of the viability of a host. In certain embodiments, the $CC_{50}$ of a compound is the amount, concentration, or dosage of the compound that is required to reduce the viability of cells treated with the compound by 50%, in comparison with cells untreated with the compound.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

As used herein, the term "alkyl" is intended to include both branched and straight chain saturated aliphatic hydrocarbon groups containing from 1 to 12 carbons, from 1 to 8 carbons, or from 1 to 4 carbons. Examples of alkyl groups include, but are not limited to, methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, and various branched chain isomers thereof, any of which is optionally substituted with 1 to 4 substituents, such as halo (e.g., F, Br, Cl, or I), $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, carboxamido, aminoacyl, aminocarboxy, carboxyamino, hydroxyl, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, and/or trihaloalkyl. In certain embodiments, the alkyl group is optionally substituted with 1 to 4 substituents, such as halo (e.g., F, Br, Cl, or I), $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, carboxamido, aminoacyl, aminocarboxy, carboxyamino, hydroxyl, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, and/or trihaloalkyl. In certain embodiments, the alkyl is optionally substituted with one or more substituents Q as described herein.

Unless otherwise indicated, the term "alkenyl" as used herein by itself or as part of another group refers to straight or branched chain hydrocarbon radicals of 2 to 12 carbons, of 2 to 8 carbons, or of 2 to 6 carbons, which include one to six carbon-carbon double bonds. Examples of alkenyl groups include, but are not limited to, vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and 4,8,12-tetradecatrienyl, any of which is optionally substituted with 1 to 4 substituents, namely, halogen, haloalkyl, alkyl, alkoxy, alkenyl, alkynyl, aryl, arylalkyl, cycloalkyl, amino, hydroxyl, heteroaryl, heterocyclyl, alkanoylamino, alkylamido, arylcarbonyl-amino, nitro, cyano, thiol, alkylthio, and/or any of the alkyl substituents set out herein. In certain embodiments, the alkenyl group is optionally substituted with 1 to 4 substituents, such as halogen, haloalkyl, alkyl, alkoxy, alkenyl, alkynyl, aryl, arylalkyl, cycloalkyl, amino, hydroxyl, heteroaryl, heterocyclyl, alkanoylamino, alkylamido, arylcarbonyl-amino, nitro, cyano, thiol, alkylthio, and/or any of the alkyl substituents set out herein. In certain embodiments, the alkenyl is optionally substituted with one or more substituents Q as described herein.

Unless otherwise indicated, the term "alkynyl" as used herein by itself or as part of another group refers to straight or branched chain hydrocarbon radicals of 2 to 12 carbons, of 2 to 8 carbons, or of 2 to 6 carbons, which include one carbon-carbon triple bond. Examples of alkynyl groups include, but are not limited to, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, and 4-dodecynyl, any of which is optionally substituted with 1 to 4 substituents, namely, halogen, haloalkyl, alkyl, alkoxy, alkenyl, alkynyl, aryl, arylalkyl, cycloalkyl, amino, heteroaryl, heterocyclyl, hydroxyl, alkanoylamino, alkylamido, arylcarbonylamino, nitro, cyano, thiol, and/or alkylthio, and/or any of the alkyl substituents set out herein. In certain embodiments, the alkynyl group is optionally substituted with 1 to 4 substituents, such as halogen, haloalkyl, alkyl, alkoxy, alkenyl, alkynyl, aryl, arylalkyl, cycloalkyl, amino, heteroaryl, heterocyclyl, hydroxyl, alkanoylamino, alkylamido, arylcarbonylamino, nitro, cyano, thiol, and/or alkylthio, and/or any of the alkyl substituents set out herein. In certain embodiments, the alkynyl is optionally substituted with one or more substituents Q as described herein.

Unless otherwise indicated, the term "cycloalkyl" as employed herein alone or as part of another group includes saturated or partially unsaturated (containing 1 or 2 double bonds) but non-aromatic cyclic hydrocarbon groups containing 1 to 4 rings, or 1 or 2 rings, including monocyclic alkyl, bicyclic alkyl (or bicycloalkyl), tricyclic alkyl, and spirocyclic alkyl, containing a total of 3 to 20 carbons forming the ring, of 3 to 15 carbons forming the ring, or of 3 to 10 carbons forming the ring. Examples of cycloalkyl groups include, but are not limited to, cyclopropyl, cyclobutyl, cyclopentyl, cyclohexyl, cycloheptyl, cyclooctyl, cyclodecyl, cyclododecyl, cyclohexenyl, adamantinyl, (Z)-bicyclo[3.3.3]undec-2-enyl, bicyclo[3.3.3]-undecanyl, decahydronaphthalenyl, bicyclo[2.2.1]heptyl, bicyclo[2.2.2]octyl, and 7,7-dimethylbicyclo[2.2.1]heptyl, any of which groups is optionally substituted with 1 to 4 substituents, such as halogen, alkyl, alkoxy, hydroxyl, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents as defined above for "alkyl." In certain embodiments, the cycloalkyl group is optionally substituted with 1 to 4 substituents, such as halogen, alkyl, alkoxy, hydroxyl, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents as defined above for "alkyl." In certain embodiments, the cycloalkyl is optionally substituted with one or more substituents Q as described herein.

Where alkyl groups as defined above have single bonds for attachment to other groups at two different carbon atoms, they are termed "alkylene" groups and optionally substituted as defined above for "alkyl."

Where alkenyl groups as defined above and alkynyl groups as defined above, respectively, have single bonds for attachment at two different carbon atoms, they are termed "alkenylene groups" and "alkynylene groups," respectively, and optionally substituted as defined above for "alkenyl" and "alkynyl."

The term "halo" or "halogen" as used herein refers to fluoro, chloro, bromo, and iodo.

The term "haloalkyl" as used herein refers to an alkyl substituted with one or more halogens.

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl), which optionally include 1 to 3 additional rings fused to a carbocyclic ring (such as aryl or cycloalkyl). In certain embodiments, the aryl group is optionally substituted through available carbon atoms with 1, 2, or 3 substituents, for example, halo, haloalkyl, alkyl, haloalkyl, alkoxy, haloalkoxy, alkenyl, trifluoromethyl, trifluoromethoxy, alkynyl, cycloalkyl-alkyl, heterocyclyl, heterocyclylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxyl, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonylaminocarbonyl, and/or any of the alkyl substituents set out herein. In certain embodiments, the aryl is optionally substituted with one or more substituents Q as described herein.

Unless otherwise indicated, the term "alkoxy," "aryloxy," or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that is optionally substituted with one or two substituents, which can be the same or different, such as alkyl, aryl, arylalkyl, heteroaryl, heteroarylalkyl, heterocyclyl, heterocyclylalkyl, cycloalkyl, cycloalkylalkyl, haloalkyl, hydroxyalkyl, alkoxyalkyl, or thioalkyl. These substituents may be further substituted with a carboxyl and/or any of the substituents defined for "alkyl." In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, each of which is optionally substituted with alkyl, alkoxy, alkylthio, halo, trifluoromethyl, or hydroxyl.

Unless otherwise indicated, the term "alkylthio," "arylthio," or "aralkylthio" as employed herein alone or as part of another group includes any of the above alkyl, aralkyl, or aryl groups linked to a sulfur atom.

Unless otherwise indicated, the term "alkylamino," "arylamino," or "arylalkylamino" as employed herein alone or as part of another group includes any of the above alkyl, aryl, or arylalkyl groups linked to a nitrogen atom.

Unless otherwise indicated, the term "heterocyclyl", "heterocyclic system" or "heterocyclic ring" is intended to mean a stable non-aromatic 3- to 14-membered monocyclic, bicyclic, tricyclic, or spirocyclic ring, which is saturated, partially unsaturated, or unsaturated, and which consists of carbon atoms and 1, 2, 3, or 4 heteroatoms independently selected from the group consisting of N, NH, O and S. The nitrogen and sulfur heteroatoms are optionally be oxidized. The heterocyclic ring can be attached to its pendant group at any heteroatom or carbon atom, which results in a stable structure. The heterocyclic rings described herein are optionally substituted on carbon or on a nitrogen atom if the resulting compound is stable with any of the substituents as defined above for "alkyl." If specifically noted, a nitrogen (N) in the heterocycle is optionally quarternized and sulfur in the heterocycle is optionally substituted with 1 or 2 oxygens. It is preferred that when the total number of S and O atoms in the heterocycle exceeds 1, then these heteroatoms are not adjacent to one another. In certain embodiments, the heterocyclyl is optionally substituted with one or more substituents Q as described herein.

Examples of heterocycles include, but are not limited to, 2-pyrrolidonyl, 2H,6H-1,5,2-dithiazinyl, 4-piperidonyl, 6H-1,2,5-thiadiazinyl, azocinyl, chromanyl, chromenyl, decahydroquinolinyl, dihydrofuran[2,3-b]tetrahydrofuranyl, imidazolidinyl, imidazolinyl, indolenyl, indolinyl, isochromanyl, isoindolinyl, morpholinyl, octahydroisoquinolinyl, oxazolidinyl, piperazinyl, piperidinyl, piperidonyl, 4-piperidonyl, pteridinyl, pyranyl, pyrazolidinyl, pyrazolinyl, pyrrolidinyl, pyrrolinyl, 4H-quinolizinyl, quinuclidinyl, tetrahydrofuranyl, tetrahydroisoquinolinyl, and tetrahydroquinolinyl. In certain embodiments, the heterocycles include, but are not limited to, piperidinyl, piperidonyl, 4-piperidonyl, and piperonyl. The heterocyclyl rings described herein are optionally substituted with any substituents defined for "alkyl."

As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatams independently selected from the group consisting of N, O and S and is aromatic in nature. The heteroaryl rings described herein are optionally substituted with any substituents defined for "alkyl." In certain embodiments, the heteroaryl is optionally substituted with one or more substituents Q as described herein.

Examples of heteroaryls include, but are not limited to, 1H-indazolyl, indolyl, 4H-quinolizinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, decahydroquinolinyl, furanyl, furazanyl, imidazolyl, indazolyl, indolizinyl, indolyl, isobenzofuranyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyrazinyl, pyrazolyl, pyrazolotriazinyl, pyridazinyl, pyridooxazolyl, pyridoimidazolyl, pyridothiazolyl, pyridinyl, pyridyl, pyrimidinyl, pyrrolyl, quinazolinyl, quinolinyl, quinoxalinyl, carbolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In certain embodiments, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl. Examples of heteroaryls include, but are not limited to, pyridin-2(1H)-on-yl, pyrimidin-2(1H)-on-yl, pyrimidin-4(3H)-on-yl, and pyridazin-3(2H)-on-yl. In certain embodiments, examples of heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, examples of monocyclic heteroaryl groups include, but are not limited to, furanyl, imidazolyl, isothiazolyl, isoxazolyl, oxadiazolyl, oxadazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In certain embodiments, examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl.

The term "cycloalkylalkyl" as used herein alone or as part of another group refers to a cycloalkyl group as defined above linked through a C atom to an alkyl.

The term "heterocyclylalkyl" or "heterocyclylalkenyl" as used herein alone or as part of another group refers to a heterocyclyl group as defined above linked through a C atom or heteroatom to an alkyl and alkenyl, respectively.

The term "arylalkyl" as used herein alone or as part of another group refers to an aryl group as defined above linked through a C atom to an alkyl.

The term "heteroarylalkyl" or "heteroarylalkenyl" as used herein alone or as part of another group refers to a heteroaryl group as defined above linked through a C atom or heteroatom to an alkyl and alkenyl, respectively.

Unless otherwise indicated, the term "acyl" as employed herein by itself or part of another group refers to an organic radical linked to a carbonyl (C=O) group; examples of acyl groups include any of the groups defined above attached to a carbonyl, such as alkanoyl, alkenoyl, aroyl, aralkanoyl, heteroaroyl, cycloalkanoyl, and cycloheteroalkanoyl.

The term "cyano," as used herein, refers to a —CN group.

The term "nitro," as used herein, refers to an —NO$_2$ group.

The term "hydroxy" or "hydroxyl," as used herein, refers to an OH group.

The phrase "pharmaceutically acceptable" is employed herein to refer to those compounds, materials, compositions, and/or dosage forms, which are, within the scope of sound medical judgment, suitable for use in contact with the tissues of human beings and animals without excessive toxicity, irritation, allergic response, or other problem or complication, commensurate with a reasonable benefit/risk ratio. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 22nd ed.; The Pharmaceutical Press: 2012; *Handbook of Pharmaceutical Excipients,* 6th ed.; Rowe et al., Eds.; The Pharmaceutical Press: 2009; *Handbook of Pharmaceutical Additives,* 3rd ed.; Ash and Ash Eds.; Synapse Information Resources, Inc.: 2007; *Pharmaceutical Preformulation and Formulation,* 2nd ed.; Gibson Ed.; CRC Press: 2009.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of a compounds disclosed herein can be synthesized from the parent compound which contains a basic or acidic moiety by conventional chemical methods. Generally, such salts can be prepared by reacting the free acid or base forms of the compound with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, PA, 1985, p. 1418, the disclosure of which is hereby incorporated by reference in its entirety.

Any compound that can be converted in vivo to provide a bioactive agent (i.e., a compound disclosed herein) is a prodrug within the scope and spirit of the disclosure.

The term "prodrugs" as employed herein includes esters and carbonates formed by reacting one or more hydroxyls of compounds disclosed herein with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) *The Practice of Medicinal Chemistry*, Wermuth et al., Ch. 31, (Academic Press, 1996);
b) *Design of Prodrugs*, edited by Bundgaard, (Elsevier, 1985);
c) *A Textbook of Drug Design and Development*, Krogsgaard-Larson and Bundgaard, eds. Ch. 5, pgs 113-191, (Harwood Academic Publishers, 1991); and
d) *Hydrolysis in Drug and Prodrug Metabolism*, Testa and Mayer, (Wiley-VCH, 2003).

In addition, a compound disclosed herein is, subsequent to their preparation, isolated and purified to obtain a composition containing an amount by weight equal to or greater than 99% of the compound ("substantially pure"), which is then used or formulated as described herein. Such a "substantially pure" compound is also contemplated herein.

The compounds disclosed herein may have asymmetric centers. The compounds disclosed herein containing an asymmetrically substituted atom can be isolated in optically active or racemic forms. Many geometric isomers of olefins, C=N double bonds, and the like can also be present in the compounds disclosed herein, and all such stable isomers are contemplated herein. Cis and trans geometric isomers of the compounds disclosed herein can be isolated as a mixture of isomers or as separated isomeric forms. All chiral, diastereomeric, racemic forms and all geometric isomeric forms of the compound disclosed herein are contemplated herein, unless the specific stereochemistry or isomeric form is specifically indicated.

When required, separation of a racemic mixture of a compound disclosed herein can be achieved by HPLC using a chiral column or by a resolution using a resolving agent such as camphonic chloride as described in Young et al., *Antimicrob. Agents Chemother.* 1995, 39, 2602-2605.

To the extent that compounds disclosed herein or salts thereof may exist in their tautomeric forms, all such tautomeric forms are contemplated herein.

All stereoisomers of the compounds disclosed herein are contemplated herein, either in admixture or in pure or substantially pure form. The compounds disclosed herein can have one or more asymmetric centers. Consequently, the compounds disclosed herein can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods, for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound disclosed herein alone or an amount of the combination of compounds disclosed herein or an amount of a compound disclosed herein in combination with other active ingredients effective to inhibit a Janus kinase or effective to treat, prevent, or ameliorate one or more symptoms of a Janus kinase-mediated disease, e.g., an inflammatory disorder.

As used herein, the term "treating" or "treatment" covers the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The term "optionally substituted" is intended to mean that a group or substituent, such as an alkyl, alkenyl, alkynyl, cycloalkyl, aryl, heteroaryl, or heterocyclyl group, may be substituted with one or more, in one embodiment, one, two, three, or four, substituents Q, each of which is independently selected from, e.g., (a) oxo (=O), cyano (—CN), halogen, and nitro (—NO$_2$); (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl, each of which is further optionally substituted with one or more, in one embodiment, one, two, three, or four, substituents $Q^a$; and —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —S(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; and (c) —C(O)R$^f$, —C(O)OR$^f$, —C(O)NR$^g$R$^h$, —C(NR$^f$)NR$^g$R$^h$, —OR$^f$, —OC(O)R$^f$, —OC(O)OR$^f$, —OC(O)NR$^g$R$^h$, —OC(=NR$^f$)NR$^g$R$^h$, —OS(O)R$^f$, —OS(O)$_2$R$^f$, —OS(O)NR$^g$R$^h$, —OS(O)$_2$NR$^g$R$^h$, —NR$^g$R$^h$, —NR$^f$C(O)R$^k$, —NR$^f$C(O)OR$^k$, —NR$^f$C(O)NR$^g$R$^h$, —NR$^f$C(=NR$^k$)NR$^g$R$^h$, —NR$^f$S(O)R$^k$, —NR$^f$S(O)$_2$R$^k$, —NR$^f$S(O)NR$^g$R$^h$, —NR$^f$S(O)$_2$NR$^g$R$^h$, —SR$^f$, —S(O)R$^f$, —S(O)$_2$R$^f$, —S(O)NR$^g$R$^h$, and —S(O)$_2$NR$^g$R$^h$; wherein each R$^f$, R$^g$, R$^h$, and R$^k$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; or (iii) R$^g$ and R$^h$ together with the N atom to which they are attached form heterocyclyl.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1$H), deuterium ($^2$H), tritium (3H), carbon-11 (C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^1$Br), iodine-123 ($^{123}$I), iodine-125 ($^{125}$I), iodine-127 ($^{127}$), iodine-129 ($^{129}$I), and iodine-131 ($^{11}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium (3H), carbon-11 ($^{11}$C), carbon-14 ($^{14}$C), nitrogen-13 ($^{13}$N), oxygen-14 ($^{14}$O), oxygen-15 ($^5$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, as example, or any nitrogen can be $^{15}$N, as example, and any oxygen can be $^{18}$O, where feasible according to the judgment of one of skill. In certain embodiments, an "isotopic variant" of a compound contains unnatural proportions of deuterium.

The term "solvate" refers to a complex or aggregate formed by one or more molecules of a solute, e.g., a compound disclosed herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

As used herein, the abbreviations for any protective groups, amino acids and other compounds, are, unless indicated otherwise, in accord with their common usage or recognized abbreviations including abbreviations found in *J. Org. Chem.* 2007, 72, 23A-24A or abbreviations established by the IUPAC-IUB Commission on Biochemical Nomenclature (Biochem. 1972, 11, 942-944).

Compounds

In one embodiment, provided herein is a compound of formula (A):

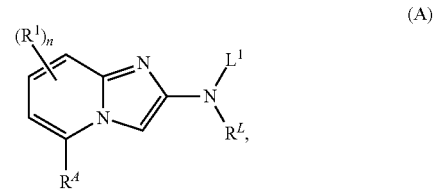

or a single enantiomer, a racemic mixture, a mixture of diastereomers, or an isotopic variant thereof; or a pharmaceutically acceptable salt, solvate, or prodrug thereof; wherein:

$L^1$ is hydrogen or —C(O)$R^2$;

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$ N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^2$ is $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;

$R^A$ is $C_3$-$C_{10}$ cycloalkyl, $C_6$-$C_{10}$ aryl, heteroaryl, or heterocyclyl;

$R^L$ is hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;

each $R^{1a}$, $R^{1b}$, $R^{1c}$, and $R^{1d}$ is independently hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl; and n is an integer of 0, 1, 2, 3, or 4;

wherein each alkyl, alkenyl, alkynyl, cycloalkyl, aryl, heteroaryl, and heterocyclyl is optionally substituted with one or more, in one embodiment, one, two, three, or four, substituents Q, where each Q is independently selected from (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OP(O)(O$R^a$)$_2$, —OS(O)$R^a$, —OS(O)$_2R^a$, —OS(O)N$R^bR^c$, —S(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; and (c) —C(O)$R^f$, —C(O)O$R^f$, —C(O)N$R^g R^h$, —C(N$R^j$)N$R^g R^h$, —O$R^f$, —OC(O)$R^f$, —OC(O)O$R^f$, —OC(O)N$R^g R^h$, —OC(=N$R^j$)N$R^g R^h$, —OS(O)$R^f$, —OS(O)$_2 R^f$, —OS(O)N$R^g R^h$, —OS(O)$_2$N$R^g R^h$, —N$R^g R^h$, —N$R^f$C(O)$R^k$, —N$R^f$C(O)O$R^k$, —N$R^f$C(O)N$R^g R^h$, —N$R^f$C(=N$R^k$)N$R^g R^h$, —N$R^f$S(O)$R^k$, —N$R^f$S(O)$_2 R^k$, —N$R^f$S(O)N$R^g R^h$, —N$R^f$S(O)$_2$N$R^g R^h$, —S$R^f$, —S(O)$R^f$, —S(O)$_2 R^f$, —S(O)N$R^g R^h$, and —S(O)$_2$N$R^g R^h$; wherein each $R^f$, $R^g$, $R^h$, and $R^k$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; or (iii) $R^g$ and $R^h$ together with the N atom to which they are attached form heterocyclyl.

In one embodiment, in formula (A), $L^1$ is hydrogen or —C(O)$R^2$;

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2 R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2 R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2 R^{1a}$, —S(O)N$R^{1b}R^{1c}$, or —S(O)$_2$N$R^{1b}R^{1c}$;

$R^2$ is $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more substituents Q;

$R^A$ is $C_6$-$C_{10}$ aryl or heteroaryl, each of which is optionally substituted with one or more substituents Q;

$R^L$ is hydrogen;

n is an integer of 0, 1, 2, 3, or 4; and each $R^{1a}$, $R^{1b}$, $R^{1c}$, $R^{1d}$, and Q is as defined herein.

In another embodiment, in formula (A), $L^1$ is hydrogen or —C(O)$R^2$;

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2 R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2 R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2 R^{1a}$, —S(O)N$R^{1b}R^{1c}$, or —S(O)$_2$N$R^{1b}R^{1c}$; $R^2$ is $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more substituents Q;

$R^A$ is $C_6$-$C_{10}$ aryl, which is optionally substituted with one or more substituents Q;

$R^L$ is hydrogen;

n is an integer of 0, 1, 2, 3, or 4; and each $R^{1a}$, $R^{1b}$, $R^{1c}$, $R^{1d}$, and Q is as defined herein.

In yet another embodiment, in formula (A), $L^1$ is hydrogen or —C(O)$R^2$;

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2 R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2 R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2 R^{1a}$, —S(O)N$R^{1b}R^{1c}$ or —S(O)$_2$N$R^{1b}R^{1c}$;

$R^2$ is $C_1$-$C_8$ alkyl or $C_3$-$C_{10}$ cycloalkyl, each of which is optionally substituted with one or more substituents Q;

$R^A$ is $C_6$-$C_{10}$ aryl, which is optionally substituted with one or more substituents Q;

$R^L$ is hydrogen;

n is an integer of 0, 1, 2, 3, or 4; and each $R^{1a}$, $R^{1b}$, $R^{1c}$, $R^{1d}$, and Q is as defined herein.

In yet another embodiment, in formula (A), $L^1$ is —C(O)$R^2$, where $R^2$ is $C_3$-$C_{10}$ cycloalkyl, which is optionally substituted with one or more substituents Q;

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2 R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2 R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2 R^{1a}$, —S(O)N$R^{1b}R^{1c}$, or —S(O)$_2$N$R^{1b}R^{1c}$;

$R^A$ is $C_6$-$C_{10}$ aryl or heteroaryl, each of which is optionally substituted with one or more substituents Q;

$R^L$ is hydrogen;

n is an integer of 0, 1, 2, 3, or 4; and each $R^{1a}$, $R^{1b}$, $R^{1c}$, $R^{1d}$, and Q is as defined herein.

In yet another embodiment, in formula (A), $L^1$ is —C(O)$R^2$, where $R^2$ is cyclopropyl or cyclobutyl;

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2 R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2 R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2 R^{1a}$, —S(O)N$R^{1b}R^{1c}$ or —S(O)$_2$N$R^{1b}R^{1c}$;

$R^A$ is $C_6$-$C_{10}$ aryl or heteroaryl, each of which is optionally substituted with one or more substituents Q;
$R^L$ is hydrogen;
n is an integer of 0, 1, 2, 3, or 4; and
each $R^{1a}$, $R^{1b}$, $R^{1c}$, $R^{1d}$, and Q is as defined herein.

In yet another embodiment, in formula (A),
$L^1$ is hydrogen or —C(O)$R^2$, wherein $R^2$ is $C_1$-$C_8$ alkyl, $C_3$-$C_1$ cycloalkyl, $C_6$-$C_{10}$ aryl, heteroaryl, or heterocyclyl, each of which is optionally substituted with one or more substituents Q;
$R^1$ at each occurrence is independently halogen or $C_1$-$C_8$ alkyl, where the alkyl is optionally substituted with one or more substituents Q;
$R^A$ is $C_6$-$C_{10}$ aryl or heteroaryl, each of which is optionally substituted with one or more substituents Q;
$R^L$ is hydrogen;
n is an integer of 0, 1, or 2; and
each Q is as defined herein.

In yet another embodiment, in formula (A),
$L^1$ is hydrogen or —C(O)$R^2$, wherein $R^2$ is $C_1$-$C_8$ alkyl, $C_3$-$C_1$ cycloalkyl, or heterocyclyl, each of which is optionally substituted with one or more substituents Q;
$R^1$ is halogen or $C_1$-$C_8$ alkyl, where the alkyl is optionally substituted with one or more substituents Q;
$R^A$ is $C_6$-$C_{10}$ aryl, which is substituted with one or more substituents Q;
$R^L$ is hydrogen;
n is an integer of 0 or 1; and
each Q is as defined herein.

In yet another embodiment, in formula (A),
$L^1$ is hydrogen or —C(O)$R^2$, wherein $R^2$ is $C_1$-$C_8$ alkyl or $C_3$-$C_1$ cycloalkyl, each of which is optionally substituted with one or more substituents Q;
$R^1$ is halogen or $C_1$-$C_8$ alkyl, which is optionally substituted with one or more substituents Q;
$R^A$ is phenyl substituted with one or two substituents Q, where each Q is independently halogen, $C_1$-$C_8$ alkyl, $C_3$-$C_{10}$ cycloalkyl, —C(O)$R^a$, —O$R^a$, or —N$R^a$S(O)$R^d$; and where the alkyl and cycloalkyl are further optionally substituted with one or two substituents $Q^a$;
$R^L$ is hydrogen;
n is an integer of 0 or 1; and
each $R^a$, $R^d$, Q, and $Q^a$ is as defined herein.

In yet another embodiment, in formula (A),
$L^1$ is hydrogen or —C(O)$R^2$, wherein $R^2$ is $C_1$-$C_8$ alkyl or $C_3$-$C_{10}$ cycloalkyl, each of which is optionally substituted with one or more substituents Q;
$R^1$ is halogen or $C_1$-$C_8$ alkyl, where the alkyl is optionally substituted with one or more substituents Q;
$R^A$ is phenyl substituted with one or two substituents Q, where each Q is independently halogen, $C_1$-$C_8$ alkyl, $C_3$-$C_{10}$ cycloalkyl, —C(O)$R^a$, —O$R^a$, or —N$R^a$S(O)$R^d$; where $R^a$ is hydrogen, methyl, or dimethylazetidinyl; and $R^d$ is cyclopropyl; and the alkyl and cycloalkyl are further optionally substituted with one or two substituents $Q^a$; where each $Q^a$ is independently cyano, 3,3,3-trifluoropropanamido, dimethylazetidinyl, hydroxypyrrolidinyl, piperidinyl, cyanopiperidinyl, morpholino, methylpiperazinyl, 1,1-dioxidothiomorpholino, or cyanomethylphenylamino;
$R^L$ is hydrogen;
n is an integer of 0 or 1; and
each Q is as defined herein.

In yet another embodiment, in formula (A),
$L^1$ is hydrogen or —C(O)$R^2$, wherein $R^2$ is $C_1$-$C_8$ alkyl or $C_3$-$C_{10}$ cycloalkyl, each of which is optionally substituted with one or more substituents Q;
$R^1$ is halogen or $C_1$-$C_8$ alkyl, where the alkyl is optionally substituted with one or more substituents Q;
$R^A$ is phenyl substituted with one or two substituents Q, where each Q is independently fluoro, methyl, cyanomethyl, cyanoethyl, (3,3,3-trifluoropropanamido)methyl, dimethylazetidinylmethyl, (hydroxypyrrolidinyl)methyl, piperidinylmethyl, cyanopiperidinyl-methyl, morpholinomethyl, (methylpiperazinyl)methyl, (1,1-dioxidothiomorpholino)methyl, (cyanomethylphenylamino)methyl, cyanocyclopropyl, methoxy, dimethylazetidinecarbonyl, or cyclopropanesulfonamido;
$R^L$ is hydrogen;
n is an integer of 0 or 1; and
each Q is as defined herein.

In yet another embodiment, in formula (A),
$L^1$ is hydrogen or —C(O)$R^2$, wherein $R^2$ is $C_1$-$C_8$ alkyl or $C_3$-$C_{10}$ cycloalkyl;
$R^1$ is halogen or $C_1$-$C_8$ alkyl;
$R^A$ is phenyl substituted with one or two substituents Q, where each Q is independently fluoro, methyl, cyanomethyl, cyanoethyl, (3,3,3-trifluoropropanamido)methyl, dimethylazetidinylmethyl, (hydroxypyrrolidinyl)methyl, piperidinylmethyl, cyanopiperidinyl-methyl, morpholinomethyl, (methylpiperazinyl)methyl, (1,1-dioxidothiomorpholino)methyl, (cyanomethylphenylamino)methyl, cyanocyclopropyl, methoxy, dimethylazetidinecarbonyl, or cyclopropanesulfonamido;
$R^L$ is hydrogen; and
n is an integer of 0 or 1.

In yet another embodiment, in formula (A),
$L^1$ is hydrogen or —C(O)$R^2$, wherein $R^2$ is isopropyl, cyclopropyl, or cyclobutyl;
$R^1$ is fluoro, chloro, or methyl;
$R^A$ is cyanomethyl-phenyl, cyanomethyl-fluorophenyl, (cyanoethyl)phenyl, (cyanocyclopropyl)phenyl, ((3,3,3-trifluoropropanamido)methyl)phenyl, (dimethylazetidinyl-methyl)phenyl, ((hydroxypyrrolidinyl)methyl)phenyl, (piperidinylmethyl)phenyl, ((cyanopiperidinyl)methyl)phenyl, (morpholinomethyl)phenyl, ((methylpiperazinyl)methyl)phenyl, ((1,1-dioxidothiomorpholino)methyl)phenyl, fluoro-((1,1-dioxidothiomorpholino)methyl)-phenyl, methyl-((1,1-dioxidothiomorpholino)methyl)phenyl, methoxyphenyl, ((cyanomethyl-phenylamino)methyl)phenyl, (dimethylazetidinecarbonyl)-phenyl, fluoro-(dimethylazetidine-carbonyl)phenyl, or (cyclopropanesulfonamido)phenyl;
$R^L$ is hydrogen; and
n is an integer of 0 or 1.

In yet another embodiment, in formula (A),
$L^1$ is hydrogen or —C(O)$R^2$, wherein $R^2$ is isopropyl, cyclopropyl, or cyclobutyl;
$R^1$ is fluoro, chloro, or methyl;
$R^A$ is 4-cyanomethylphenyl, 2-fluoro-4-cyanomethylphenyl, 3-fluoro-4-cyano-methylphenyl, 4-(1-cyanoethyl)phenyl, 4-(1-cyanocyclopropyl)phenyl, 4-((3,3,3-trifluoro-propanamido)-methyl)phenyl, 4-(3,3-dimethylazetidin-1-ylmethyl)phenyl, 4-(3-hydroxypyrrolidin-1-yl)methyl)phenyl, (R)-4-((3-hydroxypyrrolidin-1-yl)methyl)phenyl, (S)-4-((3-hydroxypyrrolidin-1-yl)methyl)phenyl, 4-(piperidin-1-ylmethyl)phenyl, 4-((4-cyanopiperidin-1-yl)methyl)phenyl, 4-(morpholinomethyl)phenyl, 4-((4-methylpiperazin-1-yl)methyl)-phenyl, 3-((1,1-dioxidothiomorpholino)methyl)phenyl, 4-((1,1-dioxidothiomorpholino)-methyl)phenyl, 2-fluoro-4-((1,1-dioxidothiomorpholino)-methyl)phenyl, 3-fluoro-4-((1,1-dioxidothiomorpholino)-methyl)phenyl, 2-methyl-4-((1,1-dioxidothiomorpholino)methyl)-phenyl, 4-methoxyphenyl, 4-((2-cyanomethylphenylamino)-methyl)phenyl, 4-(3,3-dimethyl-azetidine-1-carbonyl)phenyl, 2-fluoro-4-(3,3-dimethylazetidine-1-carbonyl)phenyl, 3-fluoro-4-(3,3-dimethylazetidine-1-carbonyl)phenyl, or 4-(cyclopropanesulfonamido)phenyl;

$R^L$ is hydrogen; and n is an integer of 0 or 1.

In still another embodiment, in formula (A), $L^1$ is —C(O)R$^2$, wherein R$^2$ is isopropyl, cyclopropyl, or cyclobutyl;

$R^1$ is fluoro, chloro, or methyl;

$R^A$ is 4-cyanomethylphenyl, 2-fluoro-4-cyanomethylphenyl, 3-fluoro-4-cyano-methylphenyl, 4-(1-cyanoethyl)phenyl, 4-(1-cyanocyclopropyl)phenyl, 4-((3,3,3-trifluoro-propanamido)-methyl)phenyl, 4-(3,3-dimethylazetidin-1-ylmethyl)phenyl, 4-((3-hydroxypyrrolidin-1-yl)methyl)phenyl, (R)-4-((3-hydroxypyrrolidin-1-yl)methyl)phenyl, (S)-4-((3-hydroxypyrrolidin-1-yl)methyl)phenyl, 4-(piperidin-1-ylmethyl)-phenyl, 4-((4-cyano-piperidin-1-yl)methyl)phenyl, 4-(morpholinomethyl)phenyl, 4-((4-methyl-piperazin-1-yl)-methyl)phenyl, 3-((1,1-dioxidothiomorpholino)methyl)phenyl, 4-((1,1-dioxido-thiomorpholino)methyl)phenyl, 2-fluoro-4-((1,1-dioxidothiomorpholino)methyl)phenyl, 3-fluoro-4-((1,1-dioxidothiomorpholino)-methyl)phenyl, 2-methyl-4-((1,1-dioxido-thiomorpholino)methyl)phenyl, 4-methoxyphenyl, 4-((2-cyanomethylphenylamino)-methyl)-phenyl, 4-(3,3-dimethylazetidine-1-carbonyl)phenyl, 2-fluoro-4-(3,3-dimethylazetidine-1-carbonyl)phenyl, 3-fluoro-4-(3,3-dimethylazetidine-1-carbonyl)phenyl, or 4-(cyclopropane-sulfonamido)phenyl;

$R^L$ is hydrogen; and n is an integer of 0 or 1.

In another embodiment, provided herein is a compound of formula (B):

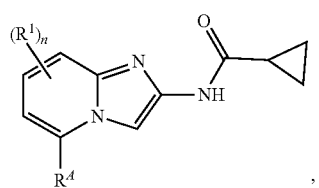

(B)

or a single enantiomer, a racemic mixture, a mixture of diastereomers, or an isotopic variant thereof; or a pharmaceutically acceptable salt, solvate, or prodrug thereof; wherein $R^1$, $R^A$, and n are each as defined herein.

In yet another embodiment, provided herein is a compound of formula (C):

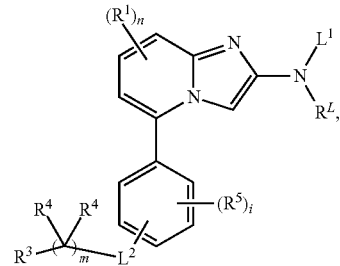

(C)

or a single enantiomer, a racemic mixture, a mixture of diastereomers, or an isotopic variant thereof; or a pharmaceutically acceptable salt, solvate, or prodrug thereof; wherein:

$L^1$ is hydrogen or —C(O)R$^2$;

$L^2$ is a single bond, —O—, —NR$^6$—, —C(O)—, —C(O)O—, —OC(O)—, —CONR$^6$—, —NR$^6$CO—, —S(O)$_2$—, —NR$^6$SO$_2$—, or —SO$_2$NR$^6$—;

m is an integer of 0, 1, 2, 3, 4, 5, or 6;

n is an integer of 0, 1, 2, or 3;

i is an integer of 0, 1, 2, 3, or 4;

$R^L$ is hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;

$R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$ NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^2$ is $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;

$R^3$ is (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^4$ at each occurrence is independently (a) hydrogen, cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$ $R^{1a}$, —S(O)$NR^{1b}R^{1c}$, or —S(O)$_2NR^{1b}R^{1c}$; or two $R^4$ groups together with the C atom to which they are attached form $C_3$-$C_{10}$ cycloalkyl or heterocyclyl;

$R^5$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)$R^{1a}$, —C(O)$OR^{1a}$, —C(O)$NR^{1b}R^{1c}$, —C($NR^{1a}$)$NR^{1b}R^{1c}$, —$OR^{1a}$, —OC(O)$R^{1a}$, —OC(O)$OR^{1a}$, —OC(O)$NR^{1b}R^{1c}$, —OC(=$NR^{1a}$)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)$OR^{1d}$, —$NR^{1a}$C(O)$NR^{1b}R^{1c}$, —$NR^{1a}$C(=$NR^{1d}$)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2$ $NR^{1b}R^{1c}$, —$SR^{1a}$, —S(O)$R^{1a}$, —S(O)$_2R^{1a}$, —S(O)$NR^{1b}R^{1c}$, or —S(O)$_2NR^{1b}R^{1c}$;

$R^6$ at each occurrence is independently hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; and each $R^{1a}$, $R^{1b}$, $R^{1c}$, and $R^{1d}$ is independently hydrogen, $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, heteroaryl, and heterocyclyl is optionally substituted with one or more, in one embodiment, one, two, three, or four, substituents Q, where each Q is independently selected from (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl, each of which is further optionally substituted with one or more, in one embodiment, one, two, three, or four, substituents $Q^a$; and (c) —C(O)$R^a$, —C(O)$OR^a$, —C(O)$NR^bR^c$, —C($NR^a$)$NR^bR^c$, —$OR^a$, —OC(O)$R^a$, —OC(O)$OR^a$, —OC(O)$NR^bR^c$, —OC(=$NR^a$)$NR^bR^c$, —OS(O)$R^a$, —OS(O)$_2R^a$, —OS(O)$NR^bR^c$, —S(O)$_2NR^bR^c$, —$NR^bR^c$, —$NR^a$C(O)$R^d$, —$NR^a$C(O)$OR^d$, —$NR^a$C(O)$NR^bR^c$, —$NR^a$C(=$NR^d$)$NR^bR^c$, —$NR^a$S(O)$R^d$, —$NR^a$S(O)$_2R^d$, —$NR^a$S(O)$NR^bR^c$, —$NR^a$S(O)$_2NR^bR^c$, —$SR^a$, —S(O)$R^a$, —S(O)$_2R^a$, —S(O)$NR^bR^c$, and —S(O)$_2NR^bR^c$, wherein each $R^a$, $R^b$, $R^c$, and $R^d$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) oxo, cyano, halogen, and nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; and (c) —C(O)$R^f$, —C(O)$OR^f$, —C(O)$NR^gR^h$, —C($NR^f$)$NR^gR^h$, —$OR^f$, —OC(O)$R^f$, —OC(O)$OR^f$, —OC(O)$NR^gR^h$, —OC(=$NR^f$)$NR^gR^h$, —OS(O)$R^f$, —OS(O)$_2R^f$, —OS(O)$NR^gR^h$, —OS(O)$_2NR^gR^h$, —$NR^gR^h$, —$NR^f$C(O)R, —$NR^f$C(O)OR, —$NR^f$C(O)$NR^gR^h$, —$NR^f$C(=$NR^k$)$NR^gR^h$, —$NR^f$S(O)R, —$NR^f$S(O)$_2R^k$, —$NR^f$S(O)$NR^gR^h$, —$NR^f$S(O)$_2NR^g$ $R^h$, —$SR^f$, —S(O)$R^f$, —S(O)$_2R^f$, —S(O)$NR^gR^h$, and —S(Q)$_2NR^gR^h$; wherein each $R^f$, $R^g$, $R^h$, and $R^k$ is independently (i) hydrogen; (ii) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, and heterocyclyl; or (iii) $R^g$ and $R^h$ together with the N atom to which they are attached form heterocyclyl.

In yet another embodiment, provided herein is a compound of formula (D):

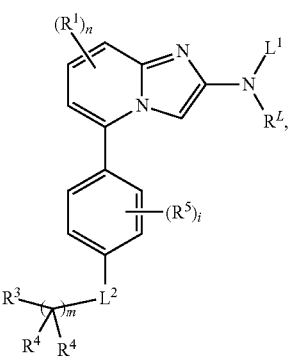

(D)

or a single enantiomer, a racemic mixture, a mixture of diastereomers, or an isotopic variant thereof; or a pharmaceutically acceptable salt, solvate, or prodrug thereof; wherein $R^1$, $R^3$, $R^4$, $R^5$, $R^L$, $L^1$, $L^2$, m, n, and i are each as defined herein; in one embodiment, $R^3$ is heterocyclyl, which is optionally substituted with one or more substituents Q as defined herein; in another embodiment, $R^3$ is 4-, 5-, or 6-membered heterocyclyl, each of which is optionally substituted with one or more substituents Q as defined herein; in yet another embodiment, $R^3$ is azetidinyl, pyrrolidinyl, piperidinyl, piperazinyl, morpholino, or thiomorpholino, each of which is optionally substituted with one or more substituents Q as defined herein; in still another embodiment, $R^3$ is 3,3-dimethylazetidinyl or 1,1-dioxidothiomorpholino.

In yet another embodiment, provided herein is a compound of formula (E):

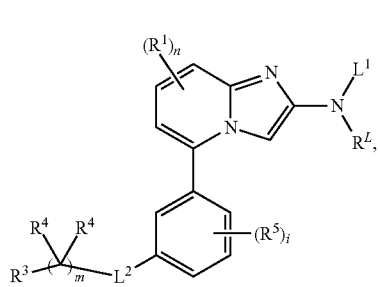

(E)

or a single enantiomer, a racemic mixture, a mixture of diastereomers, or an isotopic variant thereof; or a pharmaceutically acceptable salt, solvate, or prodrug thereof; wherein $R^1$, $R^3$, $R^4$, $R^5$, $R^L$, $L^1$, $L^2$, m, n, and i are each as defined herein; in one embodiment, $R^3$ is heterocyclyl, which is optionally substituted with one or more substituents Q as defined herein; in another embodiment, $R^3$ is 4-, 5-, or 6-membered heterocyclyl, each of which is optionally substituted with one or more substituents Q as defined herein; in yet another embodiment, $R^3$ is azetidinyl, pyrrolidinyl, piperidinyl, piperazinyl, morpholino, or thiomorpholino, each of which is optionally substituted with one or more substituents Q as defined herein; in still another embodiment, $R^3$ is 3,3-dimethylazetidinyl or 1,1-dioxidothiomorpholino.

In one embodiment, in formula (C), (D), or (E),
$L^1$ is hydrogen or —C(O)$R^2$, where $R^2$ is $C_1$-$C_8$ alkyl or $C_3$-$C_{10}$ cycloalkyl, each of which is optionally substituted with one or more substituents Q;
$L^2$ is a single bond or —C(O)—;
$R^1$ is halogen or $C_1$-$C_8$ alkyl, where the alkyl is optionally substituted with one or more substituents Q;
$R^3$ is (a) cyano; (b) heterocyclyl, which is optionally substituted with one or more substituents Q; or (c) —NR$^{1b}$R$^{1c}$, —NR$^{1a}$C(O)R$^{1d}$, —OR$^{1a}$, or —NR$^{1a}$S(O)$_2$R$^{1d}$;
each $R^4$ is independently hydrogen or $C_1$-$C_8$ alkyl, where the alkyl is optionally substituted with one or more substituents Q; or two $R^4$ groups together with the C atom to which they are attached form $C_3$-$C_{10}$ cycloalkyl, which is optionally substituted with one or more substituents Q;
$R^5$ is halogen or $C_1$-$C_8$ alkyl, where the alkyl is optionally substituted with one or more substituents Q;
$R^L$ is hydrogen;
m is an integer of 0 or 1;
n is an integer of 0 or 1;
i is an integer of 0 or 1; and
each $R^{1a}$, $R^{1b}$, $R^{1c}$, $R^{1d}$, and Q is as defined herein.

In another embodiment, in formula (C), (D), or (E),
$L^1$ is hydrogen or —C(O)$R^2$, where $R^2$ is $C_1$-$C_8$ alkyl or $C_3$-$C_{10}$ cycloalkyl, each of which is optionally substituted with one or more substituents Q;
$L^2$ is a single bond or —C(O)—;
$R^1$ is halogen or $C_1$-$C_8$ alkyl, where the alkyl is optionally substituted with one or more substituents Q;
$R^3$ is (a) cyano; (b) 4-, 5-, or 6-membered heterocyclyl, each of which is optionally substituted with one or more substituents Q; or (c) —NR$^{1b}$R$^{1c}$, —NR$^{1a}$C(O)R$^{1c}$R$^{1d}$, —OR$^{1a}$, or —NR$^{1a}$S(O)$_2$R$^{1d}$;
each $R^4$ is independently hydrogen or $C_1$-$C_8$ alkyl, where the alkyl is optionally substituted with one or more substituents Q; or two $R^4$ groups together with the C atom to which they are attached form $C_3$-$C_{10}$ cycloalkyl, which is optionally substituted with one or more substituents Q;
$R^5$ is halogen or $C_1$-$C_8$ alkyl, where the alkyl is optionally substituted with one or more substituents Q;
$R^L$ is hydrogen;
m is an integer of 0 or 1;
n is an integer of 0 or 1;
i is an integer of 0 or 1; and
each $R^{1a}$, $R^{1b}$, $R^{1c}$, $R^{1d}$, and Q is as defined herein.

In yet another embodiment, in formula (C), (D), or (E),
$L^1$ is hydrogen or —C(O)$R^2$, wherein $R^2$ is $C_1$-$C_8$ alkyl or $C_3$-$C_{10}$ cycloalkyl, each of which is optionally substituted with one or more substituents Q;
$L^2$ is a single bond or —C(O)—;
$R^1$ is halogen or $C_1$-$C_8$ alkyl, where the alkyl is optionally substituted with one or more substituents Q;
$R^3$ is (a) cyano; (b) azetidinyl, pyrrolidinyl, piperidinyl, piperazinyl, morpholino, or thiomorpholino, each of which is optionally substituted with one or more substituents Q; or (c) —NR$^{1b}$R$^{1c}$, —NR$^{1a}$C(O)R$^{1d}$, —OR$^{1a}$, or —NR$^{1a}$S(O)$_2$R$^{1d}$;
each $R^4$ is independently hydrogen or $C_1$-$C_8$ alkyl, where the alkyl is optionally substituted with one or more substituents Q; or two $R^4$ groups together with the C atom to which they are attached form $C_3$-$C_{10}$ cycloalkyl, which is optionally substituted with one or more substituents Q;
$R^5$ is halogen or $C_1$-$C_8$ alkyl, where the alkyl is optionally substituted with one or more substituents Q;
$R^L$ is hydrogen;
m is an integer of 0 or 1;
n is an integer of 0 or 1;
i is an integer of 0 or 1; and
each $R^{1a}$, $R^{1b}$, $R^{1c}$, $R^{1d}$, and Q is as defined herein.

In yet another embodiment, in formula (C), (D), or (E),
$L^1$ is hydrogen or —C(O)$R^2$, wherein $R^2$ is $C_1$-$C_8$ alkyl or $C_3$-$C_{10}$ cycloalkyl, each of which is optionally substituted with one or more substituents Q;
$L^2$ is a single bond or —C(O)—;
$R^1$ is halogen or $C_1$-$C_8$ alkyl, where the alkyl is optionally substituted with one or more substituents Q;
$R^3$ is (a) cyano; (b) azetidinyl, pyrrolidinyl, piperidinyl, piperazinyl, morpholino, or thiomorpholino, each of which is optionally substituted with one or more substituents Q; or (c) —NR$^{1b}$R$^{1c}$, —NR$^{1a}$C(O)R$^{1d}$, —OR$^{1a}$, or —NR$^{1a}$S(O)$_2$R$^{1d}$;
each $R^4$ is independently hydrogen or $C_1$-$C_8$ alkyl, where the alkyl is optionally substituted with one or more substituents Q; or two $R^4$ groups together with the C atom to which they are attached form $C_3$-$C_{10}$ cycloalkyl, which is optionally substituted with one or more substituents Q;
$R^5$ is halogen or $C_1$-$C_8$ alkyl, where the alkyl is optionally substituted with one or more substituents Q;
$R^L$ is hydrogen;
m is an integer of 0 or 1;
n is an integer of 0 or 1;
i is an integer of 0 or 1; and
each $R^{1a}$, $R^{1b}$, $R^{1c}$, $R^{1d}$, and Q is as defined herein.

In yet another embodiment, in formula (C), (D), or (E),
$L^1$ is hydrogen or —C(O)$R^2$, wherein $R^2$ is isopropyl, cyclopropyl, or cyclobutyl;
$L^2$ is a single bond or —C(O)—;
$R^1$ is fluoro, chloro, or methyl;
$R^3$ is (a) cyano, cyanomethylphenylamino, 3,3,3-trifluoropropanamido, methoxy, or cyclopropanesulfonamido; or (b) azetidinyl, pyrrolidinyl, piperidinyl, piperazinyl, morpholino, piperazinyl, or thiomorpholino, each of which is optionally substituted with one or two substituents Q, where each Q is independently oxo, cyano, hydroxyl, or $C_1$-$C_8$ alkyl, where the alkyl is optionally substituted with one or more substituents $Q^a$ as defined herein;
each $R^4$ is independently hydrogen or methyl; or two $R^4$ groups together with the C atom to which they are attached form cyclopropyl;
$R^5$ is fluoro or methyl;
$R^L$ is hydrogen;
m is an integer of 0 or 1;
n is an integer of 0 or 1; and
i is an integer of 0 or 1.

In yet another embodiment, in formula (C), (D), or (E),
$L^1$ is hydrogen or —C(O)$R^2$, wherein $R^2$ is isopropyl, cyclopropyl, or cyclobutyl;
$L^2$ is a single bond or —C(O)—;
$R^1$ is chloro or methyl;
$R^3$ is (a) cyano, cyanomethylphenylamino, 3,3,3-trifluoropropanamido, methoxy, or cyclopropanesulfonamido; or (b) azetidinyl, pyrrolidinyl, piperidinyl, piperidinyl, morpholino, piperazinyl, or thiomorpholino, each of which is optionally substituted with one or two substituents Q, where each Q is independently oxo, cyano, hydroxyl, or methyl;
each $R^4$ is independently hydrogen or methyl; or two $R^4$ groups together with the C atom to which they are attached form cyclopropyl;
$R^5$ is fluoro or methyl;
$R^L$ is hydrogen;
m is an integer of 0 or 1;
n is an integer of 0 or 1; and
i is an integer of 0 or 1.

In yet another embodiment, in formula (C), (D), or (E), $L^1$ is hydrogen;
$L^2$ is a single bond or —C(O)—;
$R^1$ is fluoro, chloro, or methyl;
$R^3$ is cyano, 2-cyanomethylphenylamino, 3,3,3-trifluoropropanamido, 3-hydroxylpyrrolidin-1-yl, (R)-3-hydroxypyrrolidin-1-yl, (S)-3-hydroxypyrrolidin-1-yl, piperidin-1-yl, 4-cyanopiperidin-1-yl, morpholin-4-yl, 4-methyl-piperazin-1-yl, 1,1-dioxidothiomorpholin-4-yl, methoxy, 3,3-dimethylazetidin-1-yl, or cyclopropanesulfonamido;
each $R^4$ is independently hydrogen or methyl; or two $R^4$ groups together with the C atom to which they are attached form cyclopropyl;
$R^5$ is fluoro or methyl;
$R^L$ is hydrogen;
m is an integer of 0 or 1;
n is an integer of 0 or 1; and
i is an integer of 0 or 1.

In still another embodiment, in formula (C), (D), or (E), $L^1$ is —C(O)$R^2$, wherein $R^2$ is isopropyl, cyclopropyl, or cyclobutyl;
$L^2$ is a single bond or —C(O)—;
$R^1$ is fluoro, chloro, or methyl;
$R^3$ is cyano, 2-cyanomethylphenylamino, 3,3,3-trifluoropropanamido, 3-hydroxylpyrrolidin-1-yl, (R)-3-hydroxypyrrolidin-1-yl, (S)-3-hydroxypyrrolidin-1-yl, piperidin-1-yl, 4-cyanopiperidin-1-yl, morpholin-4-yl, 4-methyl-piperazin-1-yl, 1,1-dioxidothiomorpholin-4-yl, methoxy, 3,3-dimethylazetidin-1-yl, or cyclopropanesulfonamido;
each $R^4$ is independently hydrogen or methyl; or two $R^4$ groups together with the C atom to which they are attached form cyclopropyl;
$R^5$ is fluoro or methyl;
$R^L$ is hydrogen;
m is an integer of 0 or 1;
n is an integer of 0 or 1; and
i is an integer of 0 or 1.

In yet another embodiment, provided herein is a compound of formula (F):

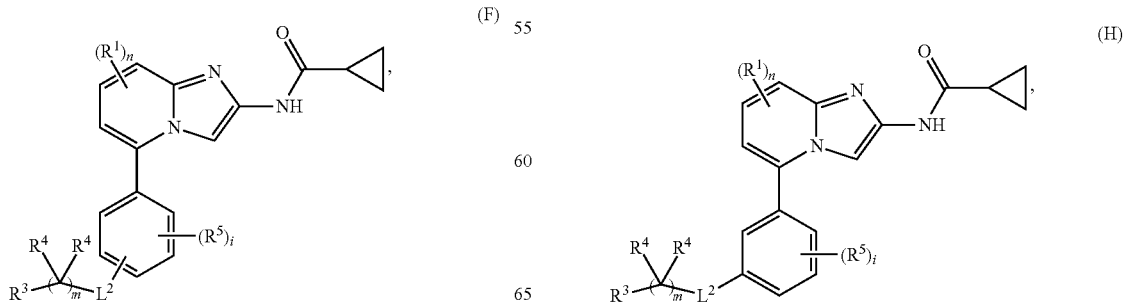

or a single enantiomer, a racemic mixture, a mixture of diastereomers, or an isotopic variant thereof; or a pharmaceutically acceptable salt, solvate, or prodrug thereof; wherein R, $R^3$, $R^4$, $R^5$, $L^2$, m, n, and i are each as defined herein; in one embodiment, $R^3$ is heterocyclyl, which is optionally substituted with one or more substituents Q as defined herein; in another embodiment, $R^3$ is 4-, 5-, or 6-membered heterocyclyl, each of which is optionally substituted with one or more substituents Q as defined herein; in yet another embodiment, $R^3$ is azetidinyl, pyrrolidinyl, piperidinyl, piperazinyl, morpholino, or thiomorpholino, each of which is optionally substituted with one or more substituents Q as defined herein; in still another embodiment, $R^3$ is 3,3-dimethylazetidinyl or 1,1-dioxidothiomorpholino.

In yet another embodiment, provided herein is a compound of formula (G):

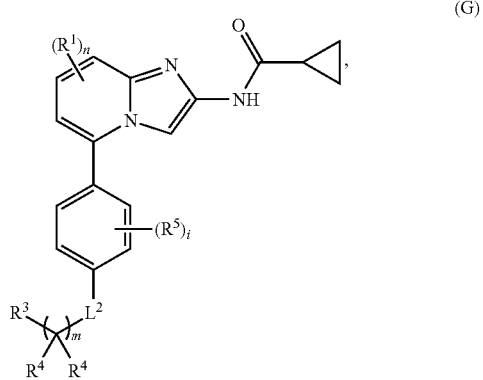

or a single enantiomer, a racemic mixture, a mixture of diastereomers, or an isotopic variant thereof; or a pharmaceutically acceptable salt, solvate, or prodrug thereof; wherein $R^1$, $R^3$, $R^4$, $R^5$, $L^2$, m, n, and i are each as defined herein; in one embodiment, $R^3$ is heterocyclyl, which is optionally substituted with one or more substituents Q as defined herein; in another embodiment, $R^3$ is 4-, 5-, or 6-membered heterocyclyl, each of which is optionally substituted with one or more substituents Q as defined herein; in yet another embodiment, $R^3$ is azetidinyl, pyrrolidinyl, piperidinyl, piperazinyl, morpholino, or thiomorpholino, each of which is optionally substituted with one or more substituents Q as defined herein; in still another embodiment, $R^3$ is 3,3-dimethylazetidinyl or 1,1-dioxidothiomorpholino.

In yet another embodiment, provided herein is a compound of formula (H):

or a single enantiomer, a racemic mixture, a mixture of diastereomers, or an isotopic variant thereof; or a pharmaceutically acceptable salt, solvate, or prodrug thereof; wherein $R^1$, $R^3$, $R^4$, $R^5$, $L^2$, m, n, and i are each as defined herein; in one embodiment, $R^3$ is heterocyclyl, which is optionally substituted with one or more substituents Q as defined herein; in another embodiment, $R^3$ is 4-, 5-, or 6-membered heterocyclyl, each of which is optionally substituted with one or more substituents Q as defined herein; in yet another embodiment, $R^3$ is azetidinyl, pyrrolidinyl, piperidinyl, piperazinyl, morpholino, or thiomorpholino, each of which is optionally substituted with one or more substituents Q as defined herein; in still another embodiment, $R^3$ is 3,3-dimethylazetidinyl or 1,1-dioxidothiomorpholino.

In still another embodiment, provided herein is a compound of formula (I):

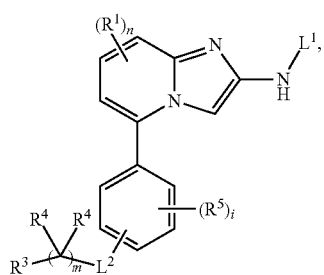

(I)

or a pharmaceutically acceptable salt, solvate, or prodrug thereof, wherein:

$L^1$ is selected from hydrogen and —C(O)$R^2$;

$L^2$ is selected from a single bond, —O—, —NR$^6$—, —C(O)—, —C(O)O—, —OC(O)—, —CONR$^6$—, —NR$^6$CO—, —S(O)$_2$—, —NR$^6$SO$_2$—, and —S(O)$_2$NR$^6$—;

m is an integer selected from 0 to 6;

n is an integer selected of 0, 1, 2, or 3;

i is an integer selected of 0, 1, 2, 3, or 4;

$R^1$ at each occurrence is independently selected from halogen, alkyl, alkenyl, alkynyl, cyano, hydroxyl, nitro, acyl, thio, thioalkoxy, thioaryloxy, thioheteroaryloxy, acylamino, alkoxy, amino, alkylamino, arylamino, heteroarylamino, amido, alkylsulfinyl, alkylsulfonyl, aminosulfonyl, sulfonyl, carboxy, cycloalkyl, cycloalkylalkyl, heterocyclyl, heterocyclylalkyl, aryl, arylalkyl, heteroaryl, and heteroarylalkyl;

$R^2$ is selected from substituted or unsubstituted alkyl, substituted or unsubstituted cycloalkyl, and substituted or unsubstituted heterocyclyl;

$R^3$ is selected from hydrogen, alkyl, alkenyl, alkynyl, aryl, arylalkyl, cycloalkyl, cycloalkylalkyl, heteroaryl, heteroarylalkyl, heterocyclyl, heterocyclylalkyl, alkoxy, aryloxy, heteroaryloxy, alkylthio, arylthio, heteroarylthio, cyano, hydroxy, —OR$^7$, —N(R$^6$)$_2$, —COR$^7$, and —CON(R$^6$)$_2$;

$R^4$ at each occurrence is independently selected from hydrogen, hydroxyl, halogen, alkyl, alkenyl, alkynyl, acyl, acyl amino, carboxy, cyano, amido, amino, alkylamino, arylamino, heteroarylamino, alkoxy, aryloxy, heteroaryloxy, cycloalkyl, cycloalkylalkyl, heterocyclyl, aryl, and heteroaryl, where permitted optionally substituted with 1 to 4 $R^8$'s; or alternatively two $R^4$'s taken together form a 3- to 9-member ring, which optionally contains 1-4 heteroatoms independently selected from N, O, and S, and is optionally substituted with 1-5 $R^8$;

$R^5$ at each occurrence is independently selected from hydrogen, halogen, alkyl, alkenyl, alkynyl, cyano, hydroxyl, nitro, acyl, thio, thioalkoxy, thioaryloxy, thioheteroaryloxy, acylamino, alkoxy, amino, alkylamino, arylamino, heteroarylamino, amido, sulfinyl, sulfonyl, aminosulfonyl, sulfonyl, carboxy, cycloalkyl, cycloalkylalkyl, heterocyclyl, heterocyclylalkyl, aryl, arylalkyl, heteroaryl, and heteroarylalkyl;

$R^6$ at each occurrence is independently selected from hydrogen, alkyl, alkenyl, alkynyl, cycloalkyl, heterocyclyl, aryl, and heteroaryl, or alternatively two $R^6$'s taken together form a 3- to 9-member ring, which optionally contains 1-4 heteroatoms independently selected from N, O, and S and is optionally substituted with 1-5 $R^8$;

$R^7$ is selected from cycloalkyl, heterocyclyl, aryl, and heteroaryl;

$R^8$ at each occurrence is independently selected from alkyl, alkenyl, alkynyl, haloalkyl, acyl, cycloalkyl, cycloalkylalkyl, heterocyclyl, heterocyclylalkyl, aryl, arylalkyl, heteroaryl, heteroarylalkyl, halogen, amino, cyano, nitro, carboxy, —C(=O)OR$^9$, trifluoromethoxy, hydroxyl, thiol, —OR$^9$, —SR$^9$, —C(=O)NR$^a$R$^b$, —NR$^a$R$^b$, —S(O)$_2$NR$^a$R$^b$, —S(O)$_2$R$^9$, —NR$^a$C(=O)R$^9$, and —OC(=O)R$^9$;

$R^9$ at each occurrence is independently hydrogen, $C_1$-$C_6$ alkyl, cycloalkyl, heterocyclyl, aryl, or heteroaryl; and $R^a$ and $R^b$ are each independently hydrogen, $C_1$-$C_6$ alkyl, or $C_3$-$C_6$ cycloalkyl, or alternatively $R^a$ and $R^b$ taken together form an optionally substituted 3-6 member ring, which optionally comprises one or two heteroatoms independently selected from N, O, and S.

In one embodiment, in formula (I), $L^1$ is selected from hydrogen and —C(O)$R^2$;

$L^2$ is selected from a single bond, —O—, —NR$^6$—, —C(O)—, —C(O)O—, —OC(O)—, —CONR$^6$—, —NR$^6$CO—, —S(O)$_2$—, —NR$^6$SO$_2$—, and —S(O)$_2$NR$^6$—;

m is an integer selected from 0 to 6;

n is an integer selected of 0, 1, 2, or 3;

i is an integer selected of 0, 1, 2, 3, or 4;

$R^1$ at each occurrence is independently selected from halogen, $C_1$-$C_8$ alkyl, $C_2$-$C_8$ alkenyl, $C_2$-$C_8$ alkynyl, cyano, hydroxyl, nitro, acyl, thio, $C_1$-$C_8$ thioalkoxy, $C_6$-$C_{10}$ thioaryloxy, thioheteroaryloxy, acylamino, $C_1$-$C_8$ alkoxy, amino, $C_1$-$C_8$ alkylamino, $C_6$-$C_{10}$ arylamino, heteroarylamino, amido, $C_1$-$C_8$ alkylsulfinyl, $C_1$-$C_8$ alkylsulfonyl, aminosulfonyl, sulfonyl, carboxy, $C_3$-$C_{10}$ cycloalkyl, $C_3$-$C_{10}$ cycloalkyl-$C_1$-$C_8$ alkyl, heterocyclyl, heterocyclyl-$C_1$-$C_8$ alkyl, $C_6$-$C_{10}$ aryl, $C_6$-$C_{10}$ aryl-$C_1$-$C_8$ alkyl, heteroaryl, and heteroaryl-$C_1$-$C_8$ alkyl;

$R^2$ is selected from substituted or unsubstituted $C_1$-$C_8$ alkyl, substituted or unsubstituted $C_3$-$C_{10}$ cycloalkyl, and substituted or unsubstituted heterocyclyl;

$R^3$ is selected from hydrogen, $C_1$-$C_8$ alkyl, $C_2$-$C_8$ alkenyl, $C_2$-$C_8$ alkynyl, $C_6$-$C_{10}$ aryl, $C_6$-$C_{10}$ aryl-$C_1$-$C_8$ alkyl, $C_3$-$C_{10}$ cycloalkyl, $C_3$-$C_{10}$ cycloalkyl-$C_1$-$C_8$ alkyl, heteroaryl, heteroaryl-$C_1$-$C_8$ alkyl, heterocyclyl, heterocyclyl-$C_1$-$C_8$ alkyl, $C_1$-$C_8$ alkoxy, $C_6$-$C_{10}$ aryloxy, heteroaryloxy, $C_1$-$C_8$ alkylthio, $C_6$-$C_{10}$ arylthio, heteroarylthio, cyano, hydroxyl, —$OR^7$, —$N(R^6)_2$, —$COR^7$, and —$CON(R^6)_2$;

$R^4$ at each occurrence is independently selected from hydrogen, hydroxyl, halogen, $C_1$-$C_8$ alkyl, $C_2$-$C_8$ alkenyl, $C_2$-$C_8$ alkynyl, acyl, acylamino, carboxy, cyano, amido, amino, $C_1$-$C_8$ alkylamino, $C_6$-$C_{10}$ arylamino, heteroarylamino, $C_1$-$C_8$ alkoxy, $C_6$-$C_{10}$ aryloxy, heteroaryloxy, $C_3$-$C_{10}$ cycloalkyl, $C_3$-$C_{10}$ cycloalkyl-$C_1$-$C_8$ alkyl, heterocyclyl, $C_6$-$C_{10}$ aryl, and heteroaryl, where permitted optionally substituted with 1 to 4 $R^8$; or alternatively two $R^4$'s taken together form a 3- to 9-member ring, which optionally contains 1-4 heteroatoms independently selected from N, O, and S, and is optionally substituted with 1-5 $R^8$;

$R^5$ at each occurrence is independently selected from hydrogen, halogen, $C_1$-$C_8$ alkyl, $C_2$-$C_8$ alkenyl, $C_2$-$C_8$ alkynyl, cyano, hydroxyl, nitro, acyl, thio, $C_1$-$C_8$ thioalkoxy, $C_6$-$C_{10}$ thioaryloxy, thioheteroaryloxy, acylamino, $C_1$-$C_8$ alkoxy, amino, $C_1$-$C_8$ alkylamino, $C_6$-$C_{10}$ arylamino, heteroarylamino, amido, sulfinyl, sulfonyl, aminosulfonyl, sulfonyl, carboxy, $C_3$-$C_{10}$ cycloalkyl, $C_3$-$C_{10}$ cycloalkyl-$C_1$-$C_8$ alkyl, heterocyclyl, heterocyclyl-$C_1$-$C_8$ alkyl, $C_6$-$C_{10}$ aryl, $C_6$-$C_{10}$ aryl-$C_1$-$C_8$ alkyl, heteroaryl, and heteroaryl-$C_1$-$C_8$ alkyl;

$R^6$ at each occurrence is independently selected from hydrogen, $C_1$-$C_8$ alkyl, $C_2$-$C_8$ alkenyl, $C_2$-$C_8$ alkynyl, $C_3$-$C_{10}$ cycloalkyl, heterocyclyl, $C_6$-$C_{10}$ aryl, and heteroaryl, or alternatively two $R^6$'s taken together form a 3- to 9-member ring, which optionally contains 1-4 heteroatoms independently selected from N, O, and S and is optionally substituted with 1-5 $R^8$;

$R^7$ is selected from $C_3$-$C_{10}$ cycloalkyl, heterocyclyl, $C_6$-$C_{10}$ aryl, and heteroaryl;

$R^8$, at each occurrence, is independently selected from $C_1$-$C_8$ alkyl, $C_2$-$C_8$ alkenyl, $C_2$-$C_8$ alkynyl, $C_1$-$C_8$ haloalkyl, acyl, $C_3$-$C_{10}$ cycloalkyl, $C_3$-$C_{10}$ cycloalkylalkyl, heterocyclyl, heterocyclyl-$C_1$-$C_8$ alkyl, $C_6$-$C_{10}$ aryl, $C_6$-$C_{10}$ aryl-$C_1$-$C_8$ alkyl, heteroaryl, heteroaryl-$C_1$-$C_5$ alkyl, halogen, amino, cyano, nitro, carboxy, —C(=O)$OR^9$, trifluoromethoxy, hydroxyl, thiol, —$OR^9$, —$SR^9$, —C(=O)$NR^aR^b$, —$NR^aR^b$, —$S(O)_2NR^aR^b$, —$S(O)_2R^9$, —$NR^aC(=O)R^9$, and —OC(=O)$R^9$;

$R^9$ at each occurrence is independently hydrogen, $C_1$-$C_6$ alkyl, $C_3$-$C_{10}$ cycloalkyl, heterocyclyl, $C_6$-$C_{10}$ aryl, or heteroaryl; and $R^a$ and $R^b$ are each independently hydrogen, $C_1$-$C_6$ alkyl, or $C_3$-$C_6$ cycloalkyl, or alternatively $R^a$ and $R^b$ taken together form an optionally substituted 3-6 member ring, which optionally comprises one or two heteroatoms independently selected from N, O, and S.

In one embodiment, provided herein is a compound selected from:

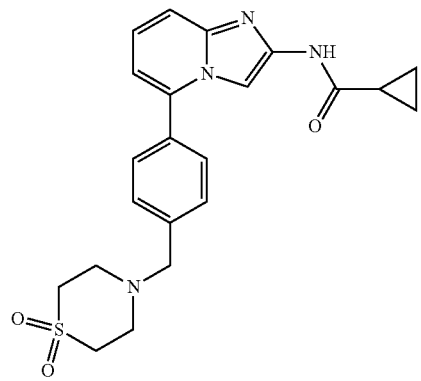
1
,

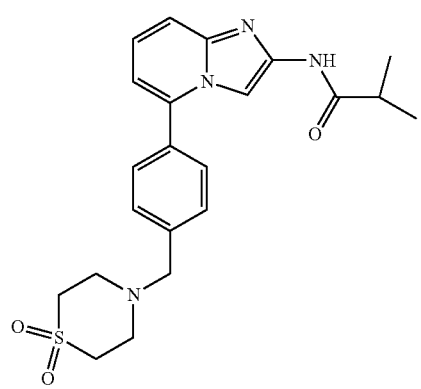
2
,

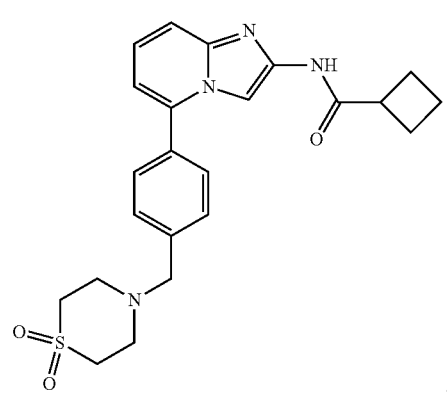
3
,

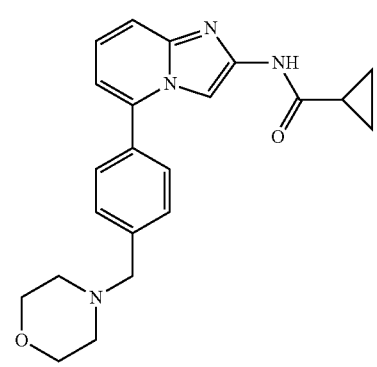
4
,

-continued
5
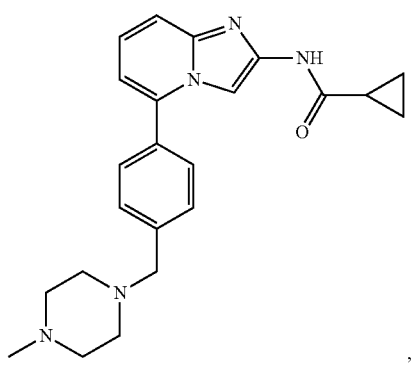
6
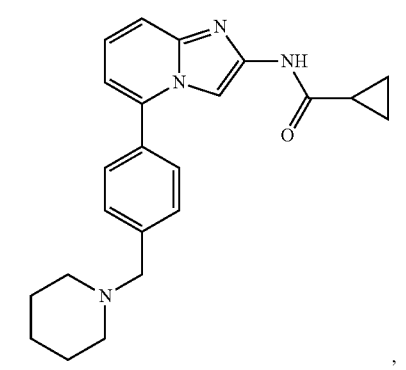
7
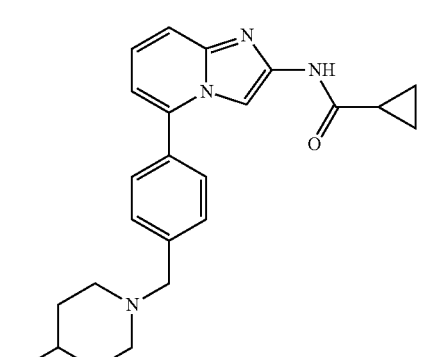
8
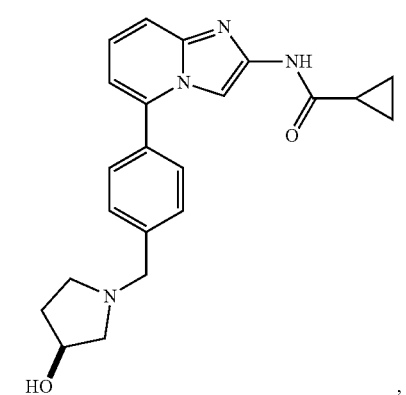
-continued
9
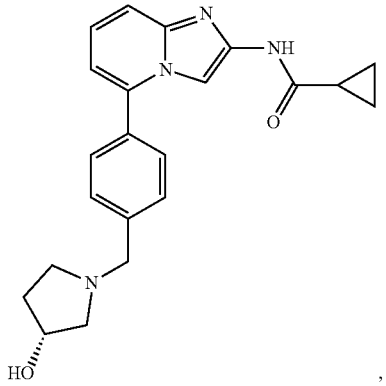
10
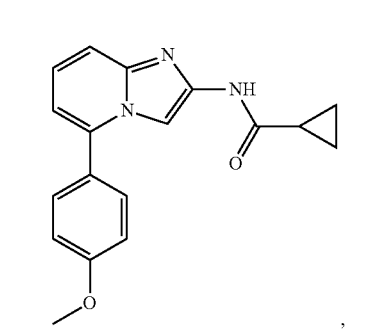
11
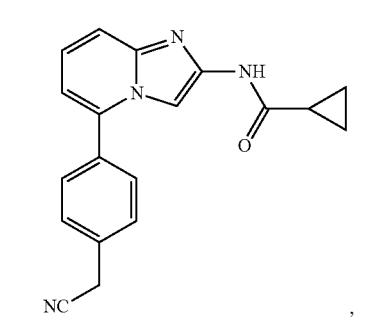
12
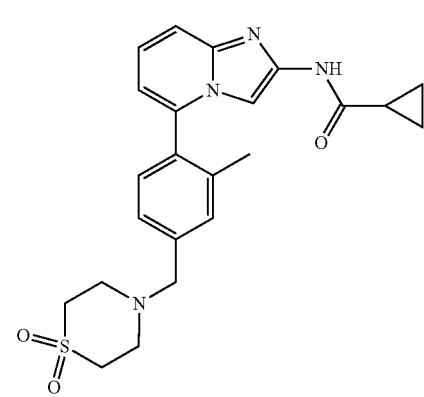

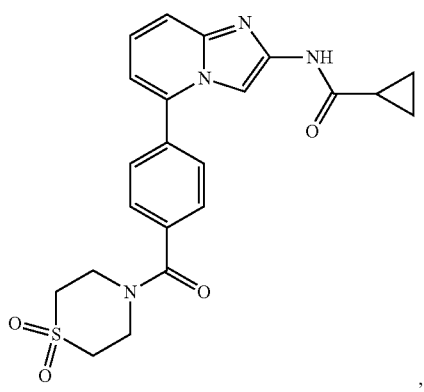
13
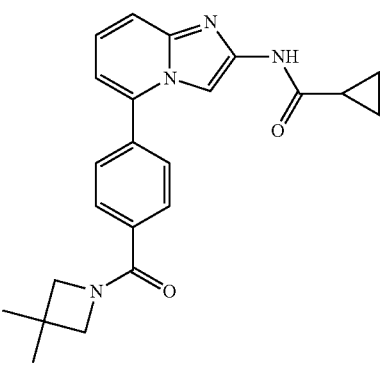
17
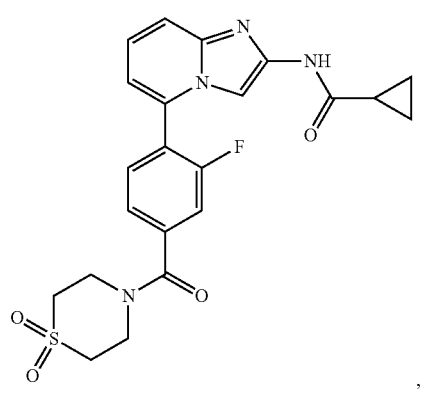
14
,
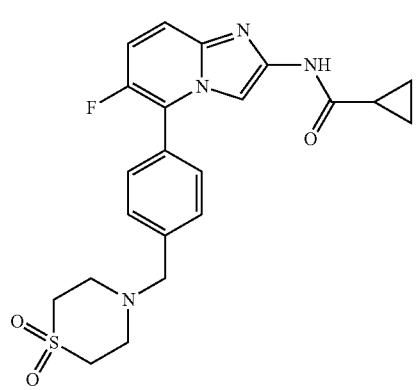
15
,
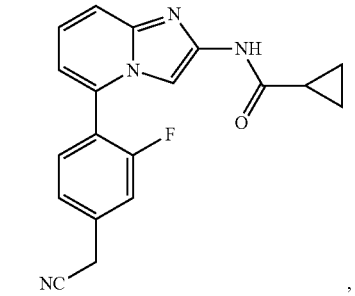
16
, and
and isotopic variants thereof; and pharmaceutically acceptable salts, solvates, and prodrugs thereof.
In another embodiment, provided herein is a compound selected from:
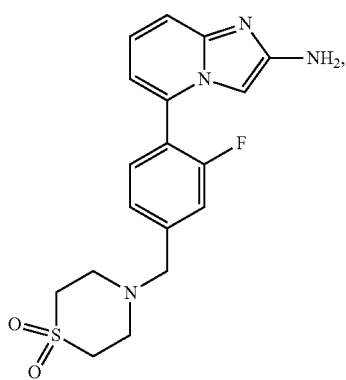
18
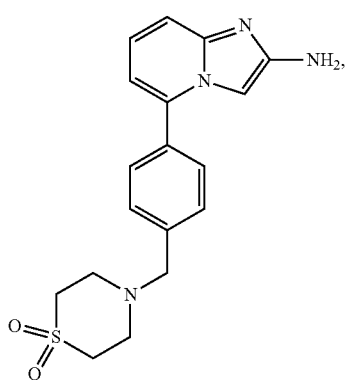
19
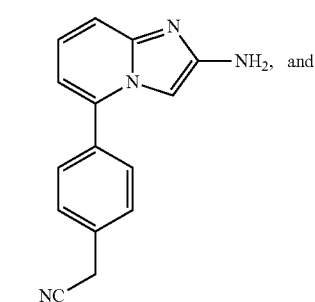
20

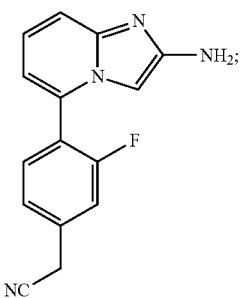
21
and isotopic variants thereof; and pharmaceutically acceptable salts, solvates, and prodrugs thereof.
In yet another embodiment, provided herein is a compound selected from:
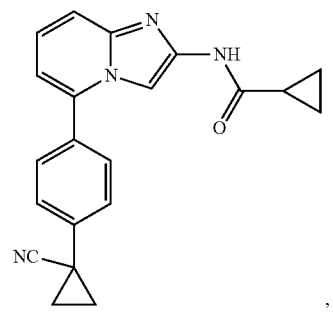
22
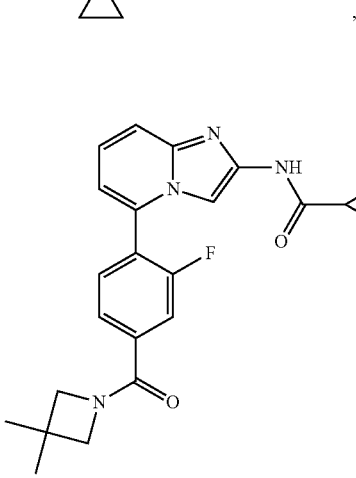
23
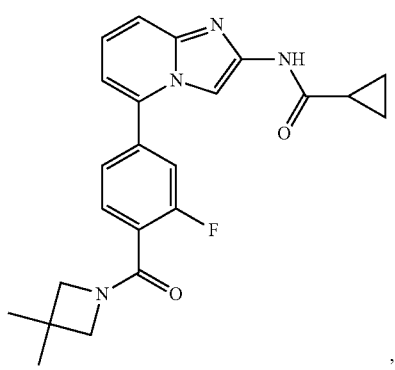
24
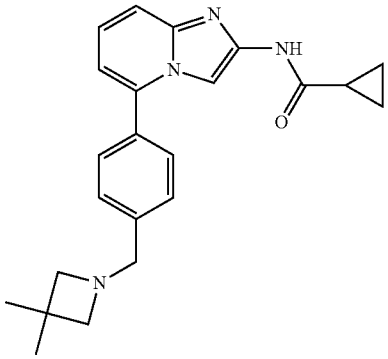
25
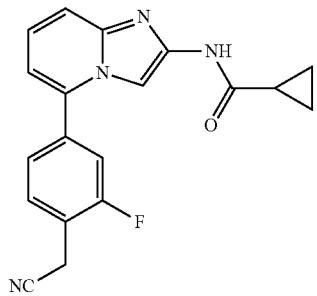
26
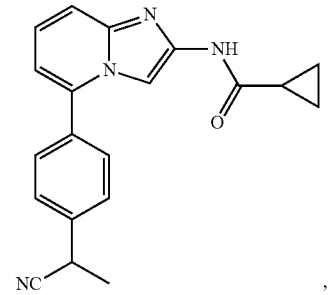
27
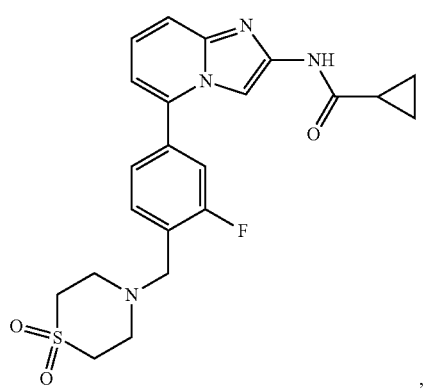
28

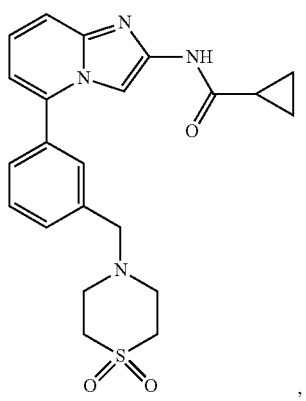

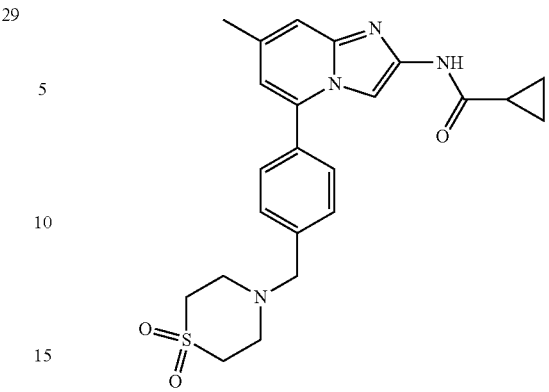

and isotopic variants thereof; and pharmaceutically acceptable salts, solvates, and prodrugs thereof.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt. See, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid. In certain embodiments, a pharmaceutically acceptable salt of a compound provided herein is a camphorsulfonic acid, hydrobromic acid, hydrochloric acid, methanesulfonic acid, phosphoric acid, or sulfuric acid salt of the compound.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, Progress in Drug Research 1962, 4, 221-294; Morozowich et al. in *Design of Biopharmaceutical Properties through Prodrugs and Analogs*; Roche Ed., APHA Acad. Pharm. Sci.: 1977; Gangwar et al., *Des. Biopharm. Prop. Prodrugs Analogs*, 1977, 409-421; Bundgaard, *Arch. Pharm. Chem.* 1979, 86, 1-39; Farquhar et al., *J. Pharm. Sci.* 1983, 72, 324-325; Wernuth in *Drug Design: Fact or Fantasy;* Jolles et al. Eds.; Academic Press: London, 1984; pp 47-72; *Design of Prodrugs*; Bundgaard et al. Eds.; Elsevier: 1985; Fleisher et al., *Methods Enzymol.* 1985, 112, 360-381; Stella et al., *Drugs* 1985, 29, 455-473; *Bioreversible Carriers in Drug in Drug Design, Theory and Application*; Roche Ed.; APHA Acad. Pharm. Sci.: 1987; Bundgaard, *Controlled Drug Delivery* 1987, 17, 179-96; Waller et al., *Br. J. Clin. Pharmac.* 1989, 28, 497-507; Balant et al., *Eur. J. Drug Metab. Pharmacokinet.* 1990, 15, 143-53; Freeman et al., *J. Chem. Soc., Chem. Commun.* 1991, 875-877; Bundgaard, *Adv. Drug Delivery Rev.* 1992, 8, 1-38; Nathwani and Wood, *Drugs* 1993, 45, 866-94; Friis and Bundgaard, *Eur. J. Pharm. Sci.* 1996, 4, 49-59; Fleisher et al., *Adv. Drug Delivery Rev.* 1996, 19, 115-130; Sinhababu and Thakker, *Adv. Drug Delivery Rev.* 1996, 19, 241-273; Taylor, *Adv. Drug Delivery Rev.* 1996, 19, 131-148; Gaignault et al., *Pract. Med. Chem.* 1996, 671-696; Browne, *Clin. Neuropharmacol.* 1997, 20, 1-12; Valentino and Borchardt, *Drug Discovery Today* 1997, 2, 148-155; Pauletti et al., *Adv. Drug. Delivery Rev.* 1997, 27, 235-256; Mizen et al., *Pharm. Biotech.* 1998, 11, 345-365; Wiebe and Knaus, *Adv. Drug Delivery Rev.* 1999, 39, 63-80; Tan et al., *Adv. Drug Delivery Rev.* 1999, 39, 117-151; Balimane and Sinko, *Adv. Drug Delivery Rev.* 1999, 39, 183-209; Wang et al., *Curr. Pharm. Design* 1999, 5, 265-287; Han et al., *AAPS Pharmsci.* 2000, 2, 1-11; Asgharnejad in *Transport Processes in Pharmaceutical Systems*; Amidon et al., Eds.; Marcell Dekker: 2000; pp 185-218; Sinha et al., *Pharm. Res.* 2001, 18, 557-564; Anand et al., *Expert Opin. Biol. Ther.* 2002, 2, 607-620; Rao, *Resonace* 2003, 19-27; Sloan et al., *Med. Res. Rev.* 2003, 23, 763-793; Patterson et al., *Curr. Pharm. Des.* 2003, 9, 2131-2154; Hu, *IDrugs* 2004, 7, 736-742; Robinson et al., *Proc. Natl. Acad. Sci. U.S.A.* 2004, 101, 14527-14532; Erion et al., *J. Pharmacol. Exp. Ther.* 2005, 312, 554-560; Fang et al., *Curr. Drug Discov. Technol.* 2006, 3, 211-224; Stanczak et al., *Pharmacol. Rep.* 2006, 58, 599-613; Sloan et al., *Pharm. Res.* 2006, 23, 2729-2747; Stella et al., *Adv. Drug Deliv. Rev.* 2007, 59, 677-694; Gomes et al., *Molecules* 2007, 12, 2484-2506; Krafz et al., *ChemMedChem* 2008, 3, 20-53; Rautio et al., *AAPS J.* 2008, 10, 92-102; Rautio et al., *Nat. Rev. Drug. Discov.* 2008, 7, 255-270; Pavan et al., *Molecules,* 2008, 13, 1035-1065; Sandros et al., *Molecules* 2008, 13, 1156-1178; Singh et al., *Curr. Med. Chem.* 2008, 15, 1802-1826; Onishi et al., *Molecules,* 2008, 13, 2136-2155; Huttunen et al., *Curr. Med. Chem.* 2008, 15, 2346-2365; and Serafin et al., *Mini Rev. Med. Chem.* 2009, 9, 481-497.

Synthetic Methods

The compounds provided herein can be prepared, isolated, or obtained by any method known to one of skill in the art.

For an example, the compounds provided herein can be prepared as shown in Scheme I, wherein $R^1$, $R^2$, $R^3$, $R^4$, $R^5$, $L^2$, m, n, and i are each as defined herein. Transformation of the carboxylic acid in compound I-1 to a Boc protected amine in compound I-2 is effected with DPPA in the present of a base (e.g., triethylamine). Deprotection of the Boc group of compound I-2 using trifluoroacetic acid, followed by acylation to form compound I-3. Suzuki coupling of pinacol borate I-4 with bromide I-3 in the presence of a catalyst (e.g., $Pd(dppf)_2C_2$) yields compound I-6.

The compounds provided herein can also be prepared as shown in Scheme II, wherein $R^1$, $R^2$, $R^3$, $R^4$, $R^5$, $L^2$, m, n, and i are each as defined herein. Treatment of the bromides I-3 and I-5 in the present of $B_2(pin)_2$ and $Pd(dppf)_2C_2$ as catalysts affords compound I-6.

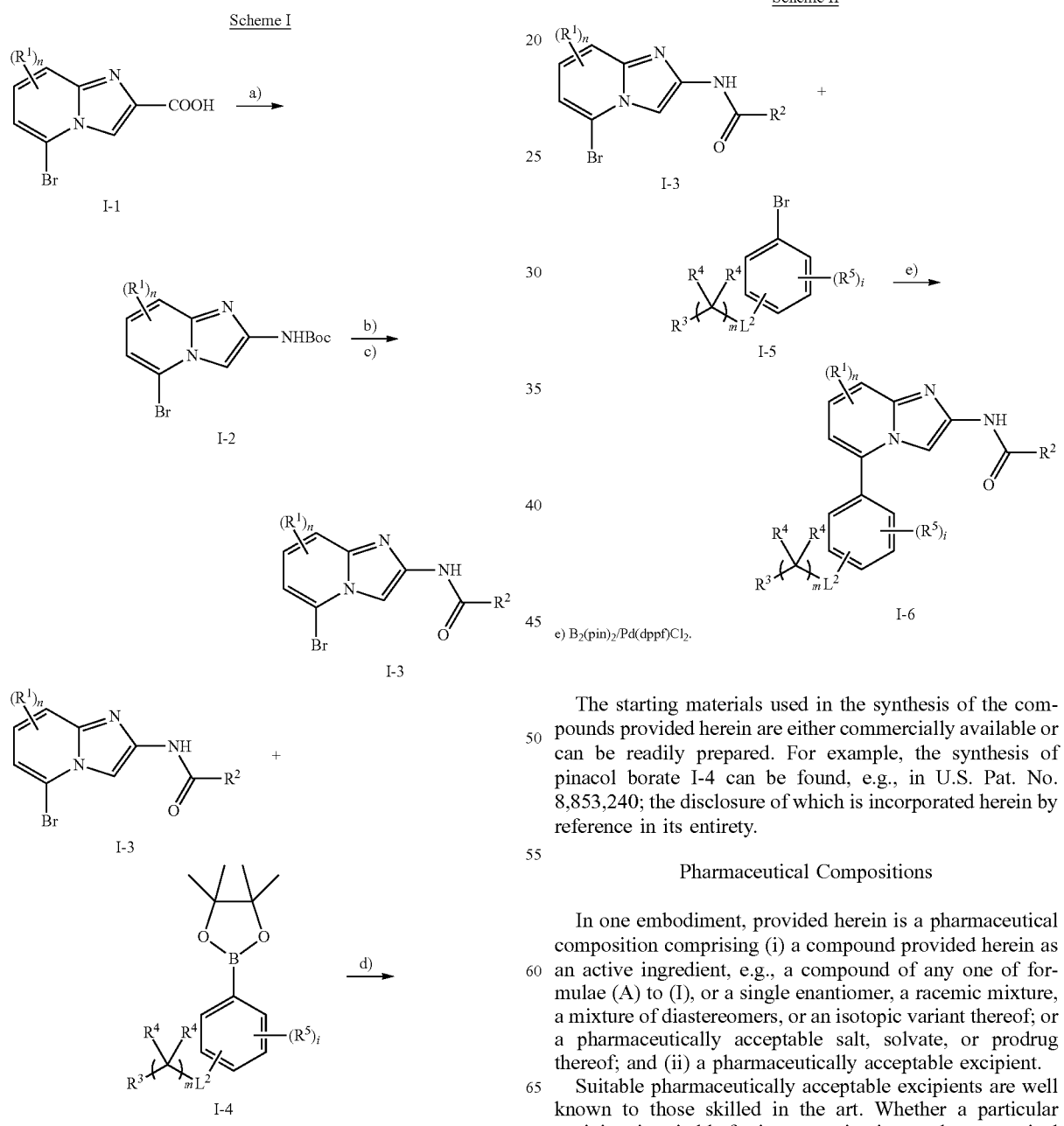

The starting materials used in the synthesis of the compounds provided herein are either commercially available or can be readily prepared. For example, the synthesis of pinacol borate I-4 can be found, e.g., in U.S. Pat. No. 8,853,240; the disclosure of which is incorporated herein by reference in its entirety.

Pharmaceutical Compositions

In one embodiment, provided herein is a pharmaceutical composition comprising (i) a compound provided herein as an active ingredient, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof; and (ii) a pharmaceutically acceptable excipient.

Suitable pharmaceutically acceptable excipients are well known to those skilled in the art. Whether a particular excipient is suitable for incorporation into a pharmaceutical composition provided herein depends on a variety of factors well known in the art, including, but not limited to, method of administration. For example, a pharmaceutical composition in an oral dosage form such as a tablet may contain an excipient not suited for use in a parenteral dosage form. The suitability of a particular excipient may also depend on the specific active ingredient in the pharmaceutical composition. For example, the decomposition of an active ingredient may be accelerated by an excipient such as lactose. Active ingredients that comprise a primary or secondary amine are particularly susceptible to such accelerated decomposition. Consequently, provided herein is a pharmaceutical composition that contains little, if any, lactose, or other mono- or di-saccharides. As used herein, the term "lactose-free" means that the amount of lactose present, if any, is insufficient to substantially increase the degradation rate of the active ingredient in the pharmaceutical composition provided herein.

The compound provided herein may be administered alone, or in combination with one or more other compounds provided herein. The pharmaceutical composition that comprises a compound provided herein, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof, can be formulated in various dosage forms for oral, parenteral, and topical administration. The pharmaceutical composition can also be formulated as a modified release dosage form, including a delayed-, extended-, prolonged-, sustained-, pulsatile-, controlled-, accelerated-, fast-, targeted-, programmed-release, and gastric retention dosage form. These dosage forms can be prepared according to conventional methods and techniques known to those skilled in the art. See, e.g., *Remington: The Science and Practice of Pharmacy, supra; Modified-Release Drug Delivery Technology,* 2nd ed.; Rathbone et al., Eds.; CRC Press: 2008.

In one embodiment, the pharmaceutical composition is provided in a dosage form for oral administration, which comprises (i) a compound provided herein, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof; and a pharmaceutically acceptable salt, solvate, or prodrug thereof; and (ii) a pharmaceutically acceptable excipient.

In another embodiment, the pharmaceutical composition is provided in a dosage form for parenteral administration, which (i) a compound provided herein, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof; and a pharmaceutically acceptable salt, solvate, or prodrug thereof; and (ii) a pharmaceutically acceptable excipient.

In yet another embodiment, the pharmaceutical composition is provided in a dosage form for topical administration, which comprises (i) a compound provided herein, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof; and a pharmaceutically acceptable salt, solvate, or prodrug thereof; and (ii) a pharmaceutically acceptable excipient.

The pharmaceutical composition provided herein can be provided in a unit-dosage or multiple-dosage form. A unit-dosage form, as used herein, refers to a physically discrete unit suitable for administration to a subject and packaged individually as is known in the art. Each unit-dose contains a predetermined quantity of an active ingredient sufficient to produce the desired therapeutic effect, in association with the required pharmaceutical excipient(s). Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include a vial, bottle of tablets or capsules, or bottle of pints or gallons.

The pharmaceutical composition provided herein can be administered at once or multiple times at intervals of time. It is understood that the precise dosage and duration of treatment may vary with the age, weight, and conditions of the subject being treated, and may be determined empirically using a known testing protocol or by extrapolation from in vivo or in vitro test or diagnostic data. It is further understood that for any particular individual, a specific dosage regimen should be adjusted over time according to the individual need and the professional judgment of the person administering or supervising the administration of the pharmaceutical composition.

A. Oral Administration

The pharmaceutical composition provided herein for oral administration can be provided in a solid, semisolid, or liquid dosage form for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gums, bulk powders, effervescent or non-effervescent powders or granules, oral mists, solutions, emulsions, suspensions, wafers, sprinkles, elixirs, and syrups. In addition to the active ingredient(s), the pharmaceutical composition can contain one or more pharmaceutically acceptable excipients, including, but not limited to, a binder, filler, diluent, disintegrant, wetting agent, lubricant, glidant, coloring agent, dye-migration inhibitor, sweetening agent, flavoring agent, emulsifying agent, suspending and dispersing agent, preservative, solvent, non-aqueous liquid, organic acid, and source of carbon dioxide.

A binder or granulator imparts cohesiveness to a tablet to ensure the tablet remaining intact after compression. Suitable binders or granulators include, but are not limited to, starches, such as corn starch, potato starch, and pre-gelatinized starch (e.g., STARCH 1500®); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), and hydroxypropyl methyl cellulose (HPMC); microcrystalline celluloses, such as AVICEL® CL-611, AVICEL® PH-101, AVICEL® PH-102, AVICEL® PH-103, AVICEL® PH-105, AVICEL® PH-112, AVICEL® PH-113, AVICEL® PH-200, AVICEL® PH-301, AVICEL® PH-302, AVICEL® RC-501, AVICEL® RC-581, and AVICEL® RC-591; and mixtures thereof. Suitable fillers include, but are not limited to, talc, calcium carbonate, microcrystalline celluloses, powdered celluloses, dextrates, kaolin, mannitol, silicic acid, sorbitol, starches, pre-gelatinized starches, and mixtures thereof. The amount of a binder or filler in the pharmaceutical composition provided herein varies upon the type of formulation, and is readily discernible to those of ordinary skill in the art. The pharmaceutical composition provided herein may contain from about 50 to about 99% by weight of a binder or filler.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical composition provided herein varies upon the type of formulation, and is readily discernible to those of ordinary skill in the art. The pharmaceutical composition provided herein may contain from about 10 to about 99% by weight of a diluent.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline celluloses, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical composition provided herein varies upon the type of formulation, and is readily discernible to those of ordinary skill in the art. The pharmaceutical composition provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starches; lycopodium; silica or silica gels, such as AEROSIL® 200 and CAB-O-SIL®; and mixtures thereof. The amount of a lubricant in the pharmaceutical composition provided herein varies upon the type of formulation, and is readily discernible to those of ordinary skill in the art. The pharmaceutical composition provided herein may contain from about 0.1 to about 5% by weight of a lubricant.

Suitable glidants include, but are not limited to, colloidal silicon dioxide, CAB-O-SIL®, and asbestos-free talc. Suitable coloring agents include, but are not limited to, any of the approved, certified, water soluble FD&C dyes, water insoluble FD&C dyes suspended on alumina hydrate, color lakes, and mixtures thereof. A color lake is an insoluble form of a water-soluble dye formed by adsorption of the water-soluble dye to a hydrous oxide of a heavy metal. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many excipients may serve a plurality of functions, even within the same formulation.

The pharmaceutical composition provided herein for oral administration can be provided as a compressed tablet, tablet triturate, chewable lozenge, rapidly dissolving tablet, multiple compressed tablet, enteric-coating tablet, or sugar-coated or film-coated tablet. An enteric-coated tablet is a compressed tablet coated with a substance that resists the action of stomach acid but dissolve or disintegrate in the intestine, thus protecting the active ingredient(s) from the acidic environment of the stomach. Enteric-coatings include, but are not limited to, fatty acids, fats, phenyl salicylate, waxes, shellac, ammoniated shellac, and cellulose acetate phthalates. A sugar-coated tablet is a compressed tablet surrounded by a sugar coating, which may be beneficial in covering up an objectionable taste or odor and in protecting the active ingredient(s) or the excipient(s) in the tablet from oxidation. A film-coated tablet is a compressed tablet that is covered with a thin layer or film of a water-soluble material. Film coatings include, but are not limited to, hydroxyethylcellulose, sodium carboxymethylcellulose, polyethylene glycol 4000, and cellulose acetate phthalate. A film coating imparts the same general characteristics as sugar coating. A multiple compressed tablet is a compressed tablet made by more than one compression cycle, including a layered tablet, and a press-coated or dry-coated tablet.

The tablet dosage forms can be prepared from the active ingredient(s) in a powdered, crystalline, or granular form, alone or in combination with one or more excipients described herein, including a binder, disintegrant, controlled-release polymer, lubricant, diluent, and/or colorant. A flavoring or sweetening agent is especially useful in the formation of a chewable tablet or lozenge.

The pharmaceutical composition provided herein for oral administration can be provided as a soft or hard capsule, which can be made from gelatin, methylcellulose, starch, or calcium alginate. The hard gelatin capsule, also known as a dry-filled capsule (DFC), consists of two sections, one slipping over the other, thus completely enclosing the active ingredient(s). The soft elastic capsule (SEC) is a soft, globular shell, such as a gelatin shell, which is plasticized by the addition of glycerin, sorbitol, or a similar polyol. The soft gelatin shell may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such a solution can be prepared as described in U.S. Pat. Nos. 4,328,245; 4,409,239; and 4,410,545. The capsules may also be coated as known by those of skill in the art in order to modify or sustain dissolution of the active ingredient(s).

The pharmaceutical composition provided herein for oral administration can be provided in a liquid or semisolid dosage form, including an emulsion, solution, suspension, elixir, and syrup. An emulsion is a two-phase system, in which one liquid is dispersed in the form of small globules throughout another liquid, which can be oil-in-water or water-in-oil. The emulsion may include a pharmaceutically acceptable non-aqueous liquid or solvent, emulsifying agent, and preservative. A suspension may include a pharmaceutically acceptable suspending agent and preservative. An aqueous alcoholic solution may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. An elixir is a clear, sweetened, and hydroalcoholic solution. A syrup is a concentrated aqueous solution of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing an active ingredient provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein the numbers "350," "550," and "750" refer to the approximate number average molecular weights ($M_n$) of the polyethylene glycols, respectively. These dosage forms can further comprise one or more antioxidants, such as butylated hydroxytoluene (BHT), butylated hydroxyanisole (BHA), propyl gallate, vitamin E, hydroquinone, a hydroxycoumarin, ethanolamine, lecithin, cephalin, ascorbic acid, malic acid, sorbitol, phosphoric acid, bisulfite, sodium metabisulfite, thiodipropionic acid and an ester thereof, and a dithiocarbamate.

The pharmaceutical composition provided herein for oral administration can be also provided in the form of a liposome, micelle, microsphere, or nanosystem. A micellar dosage form can be prepared as described in U.S. Pat. No. 6,350,458.

The pharmaceutical composition provided herein for oral administration can be provided as a non-effervescent or effervescent, granule or powder, to be reconstituted into a liquid dosage form. Pharmaceutically acceptable excipients used in the non-effervescent granule or powder may include a diluent, sweetener, and/or wetting agent. Pharmaceutically acceptable excipients used in the effervescent granule or powder include organic acids and a source of carbon dioxide.

Coloring and flavoring agents can be used in all of the dosage forms described herein.

The pharmaceutical composition provided herein for oral administration can be formulated as an immediate or modified release dosage form, including a delayed-, sustained-, pulsed-, controlled-, targeted-, and programmed-release forms.

B. Parenteral Administration

The pharmaceutical composition provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical composition provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical composition for parenteral administration can include one or more pharmaceutically acceptable excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, and dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®).

When the pharmaceutical composition provided herein is formulated for multiple dosage administration, the multiple dosage parenteral formulations must contain an antimicrobial agent at a bacteriostatic or fungistatic concentration. All parenteral formulations must be sterile as known and practiced in the art.

In one embodiment, the pharmaceutical composition for parenteral administration is provided as a ready-to-use sterile solution. In another embodiment, the pharmaceutical composition is provided as a sterile dry soluble product, including a lyophilized powder or hypodermic tablet, to be reconstituted with a vehicle prior to use. In yet another embodiment, the pharmaceutical composition is provided as a ready-to-use sterile suspension. In yet another embodiment, the pharmaceutical composition is provided as a sterile dry insoluble product to be reconstituted with a vehicle prior to use. In still another embodiment, the pharmaceutical composition is provided as a ready-to-use sterile emulsion.

The pharmaceutical composition provided herein for parenteral administration can be formulated as an immediate or modified release dosage form, including a delayed-, sustained-, pulsed-, controlled-, targeted-, and programmed-release form.

The pharmaceutical composition provided herein for parenteral administration can be formulated as a suspension, solid, semi-solid, or thixotropic liquid, for administration as an implanted depot. In one embodiment, the pharmaceutical composition provided herein is dispersed in a solid inner matrix, which is surrounded by an outer polymeric membrane that is insoluble in body fluids but allows the active ingredient(s) in the pharmaceutical composition diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical composition provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical composition provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical composition provided herein can also comprise a liposome, micelle, microsphere, nanosystem, and a mixture thereof.

Pharmaceutically acceptable carriers and excipients suitable for use in the topical formulation provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical composition can also be administered topically by electroporation, iontophoresis, phonophoresis, sonophoresis, or microneedle or needle-free injection, such as POWDERJECT™ and BIOJECT™.

The pharmaceutical composition provided herein can be provided in the form of an ointment, cream, and gel. Suitable ointment vehicles include oleaginous or hydrocarbon vehicles, including lard, benzoinated lard, olive oil, cottonseed oil, and white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout a liquid carrier. Suitable gelling agents include, but are not limited to, crosslinked acrylic acid polymers, such as carbomers, carboxypolyalkylenes, and CARBOPOL; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical composition provided herein can be administered rectally, urethrally, vaginally, or perivaginally in the form of a suppositorie, pessary, bougy, poultice or cataplasm, paste, powders, dressing, cream, plaster, contraceptive, ointment, solution, emulsion, suspension, tampon, gel, foam, spray, or enema. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid; Combinations of the various vehicles can also be used. Rectal and vaginal suppositories may be prepared by compressing or molding. The typical weight of a rectal and vaginal suppository is from about 2 to about 3 g.

The pharmaceutical composition provided herein can be administered ophthalmically in the form of a solution, suspension, ointment, emulsion, gel-forming solution, powders for a solution, gel, ocular insert, and implant.

The pharmaceutical composition provided herein can be administered intranasally or by inhalation to the respiratory tract. The pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical composition can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient(s); a propellant as solvent; and/or a surfactant, such as sorbitan trioleate, oleic acid, or an oligolactic acid.

The pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of a pharmaceutical composition provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical composition provided herein for inhaled/intranasal administration can further comprise a suitable flavor, such as menthol and levomenthol; and/or sweeteners, such as saccharin and saccharin sodium.

The pharmaceutical composition provided herein for topical administration can be formulated to be immediate release or modified release, including delayed-, sustained-, pulsed-, controlled-, targeted-, and programmed-release.

D. Modified Release

The pharmaceutical composition provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical composition in a modified release dosage form can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, supra; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press: 2006; Badawy et al., *J. Pharm. Sci.* 2007, 9, 948-959; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS PharmSciTech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical composition provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol 2.

In certain embodiments, the pharmaceutical composition provided herein in a modified release dosage form is formulated using an erodible matrix device, which is a water-swellable, erodible, or soluble polymer, including, but not limited to, a synthetic polymer, and a naturally occurring polymer and derivative, such as a polysaccharide and protein.

Materials useful in forming an erodible matrix include, but are not limited to, chitin, chitosan, dextran, pullulan, gum agar, gum arabic, gum karaya, locust bean gum, gum tragacanth, carrageenans, gum ghatti, guar gum, xanthan gum, scleroglucan, starches (such as dextrin and maltodextrin), hydrophilic colloids (such as pectin), phosphatides (such as lecithin), alginates, propylene glycol alginate, gelatin, collagen, cellulosics (such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC)), polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®), poly(2-hydroxyethylmethacrylate), polylactides, copolymers of L-glutamic acid and ethyl-L-glutamate, degradable lactic acid-glycolic acid copolymers, poly-D-(−)-3-hydroxybutyric acid, and acrylic acid derivatives (such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride).

In certain embodiments, the pharmaceutical composition provided herein is formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the composition.

The pharmaceutical composition provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical composition provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ, can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical composition in an osmotic controlled-release dosage form can further comprise additional conventional excipients as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the pharmaceutical composition provided herein is formulated as an AMT controlled-release dosage form, which comprises an asymmetric osmotic membrane that coats a core comprising the active ingredient(s) and other pharmaceutically acceptable excipients. See, U.S. Pat. No. 5,612,059 and International Pat. Appl. Publ. No. WO 2002/17918. The AMT controlled-release dosage form can be prepared according to conventional methods and techniques known to those skilled in the art, including direct compression, dry granulation, wet granulation, and a dip-coating method.

In certain embodiments, the pharmaceutical composition provided herein is formulated as an ESC controlled-release dosage form, which comprises an osmotic membrane that coats a core comprising the active ingredient(s), a hydroxylethyl cellulose, and other pharmaceutically acceptable excipients.

3. Multiparticulate Controlled Release Devices

The pharmaceutical composition provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery;* Ghebre-Selassie Ed.; CRC Press: 2010 and *Pharmaceutical Pelletization Technology;* Ghebre-Selassie Ed.; CRC Press: 1989.

Other excipients as described herein can be blended with the active ingredient(s) to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical composition provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Methods of Use

The compounds provided herein possess activity as inhibitors of a Janus kinase, and therefore are useful in the treatment of a disease associated with Janus kinase activity. Via the inhibition of a Janus kinase, the compounds provided herein are useful in inhibiting or modulating phosphorylation of a Signal Transducer and Activator of Transcription (STAT) protein, thereby interrupting or modulating gene transcription that leads to change in a cellular function.

Accordingly, in one embodiment, the compounds provided are administered to a mammal (e.g., a human) for the treatment of a variety of conditions and disorders, including, but not limited to, treating, preventing, or slowing the progression of degenerative and related condition involving in cartilage degradation, bone and/or joint degradation, for example, osteoarthritis; and/or condition involving inflammation or immune response, such as Crohn's diseases, rheumatoid arthritis, asthma, rhinitis, psoriasis, juvenile idiopathic arthritis, colitis, inflammatory bowel diseases, lupus, endotoxin-driven disease states (e.g., complications after bypass surgery or chronic endotoxin states contributing to e.g., chronic cardiac failure); disease involving impairment of cartilage turnover, such as congenital cartilage malformations; diseases associated with hypersecretion of IL6, and transplantation rejection, such as organ transplant rejection. Inhibitors of a Janus kinase are also useful in the treatment of proliferative diseases, such as leukemia and a solid tumor.

In another embodiment, provided herein is a method for treating, preventing, or ameliorating one or more symptoms of a Janus kinase-mediated condition, disorder, or disease in a subject, comprising administering to the subject a compound provided herein, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof.

In certain embodiments, the Janus kinase-mediated condition, disorder, or disease is a proliferative disease. In certain embodiments, the Janus kinase-mediated condition, disorder, or disease is an inflammatory disease. In certain embodiments, the Janus kinase-mediated condition, disorder, or disease is a cardiovascular disease. In certain embodiments, the Janus kinase-mediated condition, disorder, or disease is an immunological disorder. In certain embodiments, the Janus kinase-mediated condition, disorder, or disease is cancer. In certain embodiments, the Janus kinase-mediated condition, disorder, or disease is osteoarthritis, Crohn's disease, rheumatoid arthritis, asthma, rhinitis, psoriasis, juvenile idiopathic arthritis, ulcerative colitis, an inflammatory bowel disease, lupus, chronic cardiac failure, congenital cartilage malformation, alopecia, dry eyes, transplantation rejection, leukemia, or a solid tumor.

In certain embodiments, the Janus kinase-mediated condition, disorder, or disease is a JAK-mediated condition, disorder, or disease. In certain embodiments, the JAK1-mediated condition, disorder, or disease is a proliferative disease. In certain embodiments, the JAK1-mediated condition, disorder, or disease is an inflammatory disease. In certain embodiments, the JAK1-mediated condition, disorder, or disease is a cardiovascular disease. In certain embodiments, the JAK1-mediated condition, disorder, or disease is an immunological disorder. In certain embodiments, the JAK1-mediated condition, disorder, or disease is cancer.

In certain embodiments, the Janus kinase-mediated condition, disorder, or disease is a JAK2-mediated condition, disorder, or disease. In certain embodiments, the JAK2-mediated condition, disorder, or disease is a proliferative disease. In certain embodiments, the JAK2-mediated condition, disorder, or disease is an inflammatory disease. In certain embodiments, the JAK2-mediated condition, disorder, or disease is a cardiovascular disease. In certain embodiments, the JAK2-mediated condition, disorder, or disease is an immunological disorder. In certain embodiments, the JAK2-mediated condition, disorder, or disease is cancer.

In certain embodiments, the Janus kinase-mediated condition, disorder, or disease is a JAK3-mediated condition, disorder, or disease. In certain embodiments, the JAK3-mediated condition, disorder, or disease is a proliferative disease. In certain embodiments, the JAK3-mediated condition, disorder, or disease is an inflammatory disease. In certain embodiments, the JAK3-mediated condition, disorder, or disease is a cardiovascular disease. In certain embodiments, the JAK3-mediated condition, disorder, or disease is an immunological disorder. In certain embodiments, the JAK3-mediated condition, disorder, or disease is cancer.

In certain embodiments, the Janus kinase-mediated condition, disorder, or disease is a TYK2-mediated condition, disorder, or disease. In certain embodiments, the TYK2-mediated condition, disorder, or disease is a proliferative disease. In certain embodiments, the TYK2-mediated condition, disorder, or disease is an inflammatory disease. In certain embodiments, the TYK2-mediated condition, disorder, or disease is a cardiovascular disease. In certain embodiments, the TYK2-mediated condition, disorder, or disease is an immunological disorder. In certain embodiments, the TYK2-mediated condition, disorder, or disease is cancer.

In yet another embodiment, provided herein is a method for treating, preventing, or ameliorating one or more symptoms of a proliferative disease in a subject, comprising administering to the subject a compound provided herein, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof.

In certain embodiments, the proliferative disease is an inflammatory disease. In certain embodiments, the proliferative disease is an immunological disorder.

In certain embodiments, the proliferative disease is allergy, alopecia, amyotrophic lateral sclerosis, ankylosing spondylitis, arthritis, rheumatoid arthritis, juvenile idiopathic arthritis, asthma, atopic dermatitis, Behcet's disease, colitis, chronic obstructive pulmonary disease, Crohn's disease, dry eyes, an inflammatory bowel disease, leukemia, lymphoma, myelofibrosis, multiple sclerosis, osteoarthritis, polycythemia, psoriasis, rhinitis, sicca syndrome, a solid tumor, systemic lupus erythematosus, transplant rejection, or ulcerative colitis. In certain embodiments, the proliferative disease is an inflammatory bowel disease, psoriasis, rheumatoid arthritis, organ transplant rejection. In certain embodiments, the proliferative disease is ankylosing spondylitis, asthma, Behcet's disease, celiac disease, an inflammatory bowel disease, psoriasis, primary biliary cirrhosis, rheumatoid arthritis, Sjögren's syndrome, or systemic lupus erythematosus. In certain embodiments, the proliferative disease is alopecia areata, atopic dermatitis, an inflammatory bowel disease, organ transplant rejection, psoriasis, rheumatoid arthritis, ulcerative colitis, or vitiligo. In certain embodiments, the proliferative disease is a myeloproliferative disorder. In certain embodiments, the proliferative disease is lymphomas, myelofibrosis, pancreatic cancer, or polycythemia vera.

In certain embodiments, the proliferative disease is cancer. In certain embodiments, the cancer is relapsed cancer. In certain embodiments, the cancer is drug-resistant cancer. In certain embodiments, the cancer is relapsed drug-resistant cancer. In certain embodiments, the cancer is multidrug-resistant cancer. In certain embodiments, the cancer is relapsed multidrug-resistant cancer.

In certain embodiments, the subject is a mammal. In certain embodiments, the subject is a human. In certain embodiments, the subject is a primate other than a human, a farm animal such as cattle, a sport animal, or a pet such as a horse, dog, or cat.

In certain embodiments, the conditions, disorders, or diseases treatable with a compound provided herein include, but are not limited to, (1) inflammatory or allergic diseases, including systemic anaphylaxis and hypersensitivity disorders, atopic dermatitis, urticaria, drug allergies, insect sting allergies, food allergies (e.g., celiac disease), and mastocytosis; (2) inflammatory bowel diseases, including Crohn's disease, ulcerative colitis, ileitis, and enteritis; (3) vasculitis and Behcet's syndrome; (4) psoriasis and inflammatory dermatoses, including dermatitis, eczema, atopic dermatitis, allergic contact dermatitis, urticaria, viral cutaneous pathologies such as those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease;

(6) autoimmune diseases, including arthritis (e.g., rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the proliferative diseases treatable with a compound provided herein include, but are not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenström's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and (42) other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas. See, e.g., Fishman et al., *Medicine,* 2d ed., J. B. Lippincott Co., Philadelphia: 1985; and Murphy et al., *Informed Decisions:*

*The Complete Book of Cancer Diagnosis, Treatment, and Recovery,* Viking Penguin: 1997.

Depending on the disorder, disease, or condition to be treated, and the subject's conditions, a compound or pharmaceutical composition provided herein can be administered by an oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) route of administration and can be formulated, alone or together, in a suitable dosage unit with pharmaceutically acceptable excipients appropriate for each route of administration. Also provided herein is administration of a compound or pharmaceutical composition provided herein in a depot formulation, in which the active ingredient is released over a predefined time period.

In the treatment, prevention, or amelioration of one or more symptoms of a disorder, disease, or condition described herein, an appropriate dosage level generally is ranging from about 0.001 to about 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

For oral administration, a pharmaceutical composition provided herein can be formulated in the form of tablets each containing from about 1.0 to about 1,000 mg of an active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the subject to be treated. A pharmaceutical composition provided herein can be administered on a regimen of 1 to 4 times per day, including once, twice, three times, and four times per day.

It will be understood, however, that the specific dose level and frequency of dosage for any particular subject can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

In one embodiment, provided herein is a method for modulating the activity of a tyrosine kinase, in one embodiment, a Janus kinase, comprising contacting the kinase with a compound provided herein, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof.

In another embodiment, provided herein is a method for modulating the activity of a tyrosine kinase, in one embodiment, a Janus kinase, in a subject, comprising administering to the subject a compound disclosed herein, e.g., a compound of any one of formulae (A) to (I), or a single enantiomer, a racemic mixture, a mixture of diastereomers, or an isotopic variant thereof; or a pharmaceutically acceptable salt, solvate, or prodrug thereof.

In certain embodiments, the Janus kinase is JAK1. In certain embodiments, the Janus kinase is JAK2. In certain embodiments, the Janus kinase is JAK3. In certain embodiments, the Janus kinase is TYK2.

In certain embodiments, a compound provided herein is a selective inhibitor of JAK1. In certain embodiments, a compound provided herein has a selectivity against JAK1 over JAK2 ranging from about 2 fold, about 4 fold, about 8 fold, about 20 fold, about 50 fold, about 100 fold, about 200 fold, about 500 fold, or about 1000 fold. In certain embodiments, a compound provided herein has a selectivity against JAK over JAK3 ranging from about 2 fold, about 4 fold, about 8 fold, about 20 fold, about 50 fold, about 100 fold, about 200 fold, about 500 fold, or about 1000 fold. In certain embodiments, a compound provided herein has a selectivity against JAK over TYK2 ranging from about 2 fold, about 4 fold, about 8 fold, about 20 fold, about 50 fold, about 100 fold, about 200 fold, about 500 fold, or about 1000 fold.

In certain embodiments, a compound provided herein is a selective inhibitor of JAK2. In certain embodiments, a compound provided herein has a selectivity against JAK2 over JAK ranging from about 2 fold, about 4 fold, about 8 fold, about 20 fold, about 50 fold, about 100 fold, about 200 fold, about 500 fold, or about 1000 fold. In certain embodiments, a compound provided herein has a selectivity against JAK2 over JAK3 ranging from about 2 fold, about 4 fold, about 8 fold, about 20 fold, about 50 fold, about 100 fold, about 200 fold, about 500 fold, or about 1000 fold. In certain embodiments, a compound provided herein has a selectivity against JAK2 over TYK2 ranging from about 2 fold, about 4 fold, about 8 fold, about 20 fold, about 50 fold, about 100 fold, about 200 fold, about 500 fold, or about 1000 fold.

In certain embodiments, a compound provided herein is a selective inhibitor of JAK3. In certain embodiments, a compound provided herein has a selectivity against JAK3 over JAK ranging from about 2 fold, about 4 fold, about 8 fold, about 20 fold, about 50 fold, about 100 fold, about 200 fold, about 500 fold, or about 1000 fold. In certain embodiments, a compound provided herein has a selectivity against JAK3 over JAK2 ranging from about 2 fold, about 4 fold, about 8 fold, about 20 fold, about 50 fold, about 100 fold, about 200 fold, about 500 fold, or about 1000 fold. In certain embodiments, a compound provided herein has a selectivity against JAK3 over TYK2 ranging from about 2 fold, about 4 fold, about 8 fold, about 20 fold, about 50 fold, about 100 fold, about 200 fold, about 500 fold, or about 1000 fold.

In certain embodiments, a compound provided herein is a selective inhibitor of TYK2. In certain embodiments, a compound provided herein has a selectivity against TYK2 over JAK ranging from about 2 fold, about 4 fold, about 8 fold, about 20 fold, about 50 fold, about 100 fold, about 200 fold, about 500 fold, or about 1000 fold. In certain embodiments, a compound provided herein has a selectivity against TYK2 over JAK3 ranging from about 2 fold, about 4 fold, about 8 fold, about 20 fold, about 50 fold, about 100 fold, about 200 fold, about 500 fold, or about 1000 fold. In certain embodiments, a compound provided herein has a selectivity against TYK2 over JAK3 ranging from about 2 fold, about 4 fold, about 8 fold, about 20 fold, about 50 fold, about 100 fold, about 200 fold, about 500 fold, or about 1000 fold.

In certain embodiments, the selectivity of a compound provided herein against a first kinase over a second kinase is determined by the ratio of the $IC_{50}$ value of the compound against the first kinase over the $IC_{50}$ value against the second kinase.

The present disclosure includes within its scope pharmaceutical compositions comprising, as an active ingredient, a therapeutically effective amount of at least one of the compounds provided herein, alone or in combination with a pharmaceutical carrier or diluent. Optionally, the compounds provided herein can be used alone, in combination with other compounds provided herein, or in combination with one or more other therapeutic agent(s) with similar therapeutic activity, or other pharmaceutically active material, e.g., an anti-inflammatory agent or other pharmaceutically active material.

Thus, the compound provided herein, e.g., a compound of any one of formulae (A) to (I), or an enantiomer, a mixture of enantiomers, a mixture of two or more diastereomers, or an isotopic variant thereof; or a pharmaceutically acceptable salt, solvate, hydrate, or prodrug thereof; can also be combined or used in combination with other agents or therapies useful in the treatment, prevention, or amelioration of one or more symptoms of the conditions, disorders, or diseases for which the compounds provided herein are useful.

Suitable other therapeutic agents can also include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

In certain embodiments, the other therapies that may be used in combination with the compounds provided herein include, but are not limited to, surgery, endocrine therapy, biologic response modifiers (e.g., interferons, interleukins, and tumor necrosis factor (TNF)), hyperthermia and cryotherapy, and agents to attenuate any adverse effects (e.g., antiemetics).

The compounds provided herein can be employed in combination with other Janus kinase inhibitors or one or more other suitable therapeutic agents useful in the treatment of the aforementioned disorders, including: anti-inflammatory agents, anti-arthritis agents, anti-autoimmune agents, anti-transplantation rejection agents, anti-asthma agents, anti-rhinitis agents, anti-chronic obstruction pulmonary (COPD) agents, anti-inflammatory bowl agents, anti-systemic lupus erythematosus agents, anti-psoriasis agents, and/or anti-proliferative agents.

Examples of suitable anti-inflammatory agents for use in combination with the compounds provided herein include, but are not limited to, azathioprine, corticosteroids (e.g., prednisolone and dexamethasone), cyclophosphamide, cyclosporine A, tacrolimus, mycophenolate mofetil, muromonab-CD3, ATG, aspirin, acetaminophen, ibuprofen, naproxen, Celebrex, and piroxicam.

Examples of suitable anti-arthritis agents for use in combination with the compounds provided herein include, but are not limited to, non-steroidal anti-inflammatory drugs (NSAIDS), steroids, synthetic DMWARDS (methotrexate, leflunomide, sulfasalazine, auranofin, sodium aurothiomalate, penicillamine, chloroquine, hydroxychloroquine, azathioprine and cyclosporine), and biological DMWARDS (infliximab, etanercept, adalimumab, rituximab, and abatacept).

Examples of suitable anti-autoimmune agents for use in combination with the compounds provided herein include, but are not limited to, glucocorticoids, cytostatic agents (purine analog), alkylating agents (cyclophosphamide, nitrosoureas, and platinum compounds), anti-metabolites (methotrexate, azathioprine, and mercaptopurine), cytotoxic antibiotics (dactiomycin anthracyclines, mitomycine C, blemocyin, and mithramycin), antibodies (anti-CD20, anti CD-25, anti-CD3 (OTK3), monoclonal antibodies, ATGAM® and thymoglobulin), cyclosporin, tacrolimus, rapamycine (siolimus), interferons (e.g., IFN-β), TNF binding proteins (infiximab, etanercept, and adalimumab), mycophenolate, fingolimod, or myriocin (thermozymocidin).

Examples of suitable anti-transplantation rejection agents for use in combination with the compounds provided herein include, but are not limited to, calcineurin inhibitors (e.g., cyclosporin and tacrolimus (FK506)), mTOR inhibitors (e.g., sirolimus and everolimus), anti-proliferatives (e.g., azathioprine and mycophenolic acid), corticosteroids (e.g., prednisolone and hydrocortisone), antibodies (e.g., monoclonal anti-IL-2R$^a$ receptor antibodies, basiliximab, and daclizumab), polyclonal anti-T-cell antibodies (e.g., antithymocyte globulin (ATG) and anti-lymphocyte globulin (ALG)).

Examples of suitable anti-asthma and/or anti-rhinitis and/or anti-COPD agents for use in combination with the compounds provided herein include, but are not limited to, beta2-adrenoceptor agonists (e.g., salbutamol, levalbuterol, terbutaline, and bitolterol), epinephrine (inhaled or tablets), anticholinergics (e.g., ipratropium bromide), glucocorticoids (oral or inhaled), Long-acting 02-agonists (e.g., salmeterol, formoterol, bambuterol, and sustained-release oral albuterol), combinations of inhaled steroids and long-acting bronchodilators (e.g., fluticasone/salmeterol, and budesonide/formoterol), leukotriene antagonists and synthesis inhibitors (e.g., montelukast, zafirlukast, and zileuton), inhibitors of mediator release (e.g., cromoglycate and ketotifen), biological regulators of IgE response (e.g., omalizumab), antihistamines (e.g., ceterizine, cinnarizine, and fexofenadine), vasoconstrictors (e.g., oxymethazoline, xylomethazoline, nafazoline, and tramazoline). In addition, a compound provided herein can be administered in combination with emergency therapies for asthma and/or COPD, and such therapies include oxygen or heliox administration, nebulized salbutamol or terbutaline (optionally combined with an anticholinergic (e.g., ipratropium)), systemic steroids (oral or intravenous, e.g., prednisone, prednisolone, methylprednisolone, dexamethasone, and hydrocortisone), intravenous salbutamol, nonspecific beta-agonists, injected or inhaled (e.g., epinephrine, isoetharine, isoproterenol, and metaproterenol), anticholinergics (IV or nebulized, e.g., glycopyrrolate, atropine, and ipratropium), methylxanthines (e.g., theophylline, aminophylline, and bamiphylline), inhalation anesthetics that have a bronchodilatory effect (e.g., isoflurane, halothane, and enflurane), ketamine, or intravenous magnesium sulfate.

Examples of suitable anti-inflammatory bowl agents for use in combination with the compounds provided herein include, but are not limited to: glucocorticoids (e.g., prednisone and budesonide), synthetic disease modifying immunomodulatory agents (e.g., methotrexate, leflunomide, sulfasalazine, mesalazine, azathioprine, 6-mercaptopurine, and cyclosporin), and biological disease modifying immunomodulatory agents (e.g., infliximab, adalimumab, rituximab, and abatacept).

Examples of suitable anti-systemic lupus erythematosus agents for use in combination with the compounds provided herein include, but are not limited to, disease-modifying antirheumatic drugs (DMARDs) such as antimalarials (e.g., plaquenil and hydroxychloroquine), immunosuppressants (e.g., methotrexate and azathioprine), cyclophosphamide, mycophenolic acid, immunosuppressive drugs and analgesics such as nonsteroidal anti-inflammatory drugs, opiates (e.g., dextropropoxyphene and co-codamol), opioids (e.g., hydrocodone, oxycodone, MS Contin, and methadone), and the fentanyl duragesic transdermal patch.

Examples of suitable anti-psoriasis agents for use in combination with the compounds provided herein include, but are not limited to, topical treatments such as bath solutions, moisturizers, medicated creams, and ointments containing coal tar, dithranol (anthralin), corticosteroids like desoximetasone (e.g., TOPICORT®), fluocinonide, vitamin D3 analogues (e.g., calcipotriol), argan oil and retinoids (e.g., etretinate, acitretin, and tazarotene), systemic treatments such as methotrexate, cyclosporine, retinoids, tioguanine, hydroxyurea, sulfasalazine, mycophenolate mofetil, azathioprine, tacrolimus, fumaric acid esters, or biologies such as alefacept, etanercept, adalimumab, infliximab, efalizumab, and ustekinumab (a IL-12 and IL-23 blocker). In addition, a compound provided herein can be administered in combination with other therapies including, but not limited to phototherapy, or photochemotherapy (e.g., psoralen and ultraviolet A phototherapy (PUVA)).

Examples of suitable anti-proliferative agents for use in combination with the compounds provided herein include, but are not limited to, methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibodies (e.g., trastuzumab), capecitabine, raloxifene hydrochloride, EGFR inhibitors (e.g., gefitinib, erlotinib, cetuximab), VEGF inhibitors (e.g., bevacizumab), proteasome inhibitors (e.g., bortezomib), imatinib, or Hsp90 inhibitors (e.g., 17-AAG). In addition, a compound provided herein can be administered in combination with other therapies including, but not limited to, radiotherapy or surgery. In a specific embodiment the proliferative disorder is cancer, myeloproliferative disease, or leukaemia.

Such other agents, or drugs, can be administered, by a route and in an amount commonly used therefor, simultaneously or sequentially with the compound provided herein, e.g., a compound of any one of formulae (A) to (I), or an enantiomer, a mixture of enantiomers, a mixture of two or more diastereomers, or an isotopic variant thereof; or a pharmaceutically acceptable salt, solvate, hydrate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein are kits which, when used by the medical practitioner, can simplify the administration of appropriate amounts of active ingredients to a subject. In certain embodiments, the kit provided herein includes a container and a dosage form of a compound provided herein, e.g., a compound of any one of formula (A) to (I), or an enantiomer, a mixture of enantiomers, a mixture of two or more diastereomers, or an isotopic variant thereof; or a pharmaceutically acceptable salt, solvate, hydrate, or prodrug thereof.

In certain embodiments, the kit includes a container comprising a dosage form of the compound provided herein, e.g., a compound of any one of formula (A) to (I), or an enantiomer, a mixture of enantiomers, a mixture of two or more diastereomers, or an isotopic variant thereof; or a pharmaceutically acceptable salt, solvate, hydrate, or prodrug thereof; in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); L (microliters); L (liter); mM (millimolar); M (micromolar); Hz (Hertz); MHz (megahertz); J (coupling constant); mmol (millimoles); eq. (equivalent); ppm (parts per million); h, hr, or hrs (hours); min (minute); RT or rt (room temperature); sat. or sat'd (saturated); aq. (aqueous); MS (mass spectrometry); NMR (nuclear magnetic resonance); HPLC (high performance liquid chromatography or high pressure liquid chromatography); LC/MS (high performance liquid chromatography/mass spectrometry); TLC (thin layer chromatography); ACN or MeCN (acetonitrile); AcOH or HOAc (acetic acid); CDCl$_3$ (deuterated chloroform); DCM (dichloromethane); DMF (N,N-dimethylformamide); DMSO (dimethylsulfoxide); DMSO-d$_6$ (deuterated dimethylsulfoxide); EtOAc or EA (ethyl acetate); Et$_2$O (diethyl ether); EtOH (ethanol); MeOH (methanol); t-BuOH (tert-butanol); PE (petroleum ether); THF (tetrahydrofuran); DIPEA (N,N-diisopropylethylamine); TEA or Et$_3$N (triethylamine); TFA (trifluoroacetic acid); Pd(dppf)Cl$_2$ ([1,1'-bis(diphenylphosphino)ferrocene] dichloro-palladium); B$_2$(pin)$_2$ (bis(pinacolato)diboron); DPPA (diphenylphosphoryl azide); Me (methyl); Et (ethyl); iPr, (isopropyl); tBu (tert-butyl); Boc (tert-butoxylcarbony); Bn (benzyl); Ph (phenyl); and AcO (acetate).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies herein are intended to exemplify the applicable chemistry through the use of specific examples and are not indicative of the scope of the disclosure.

Example A

In Vitro Assays for Determining the Inhibition of Janus Kinases

The in vitro inhibition of recombinant human JAKs was determined as follow.

Compounds were tested in LANTHASCREEN™ time-resolved fluorescence energy transfer (TR-FRET) enzymatic assays from Invitrogen. The human Janus kinase 1 (JAK1) used in the assay is the recombinant JAK catalytic domain (amino acids 866-1154) expressed and purified from insect cells (Invitrogen, Cat. No. PV4774). The human Janus kinase 2 (JAK2) used in the assay is the recombinant JAK2 catalytic domain (amino acids 808-1132) expressed and purified from insect cells (Invitrogen, Cat. No. PV4210). The human Janus kinase 3 (JAK3) used in the assay is the recombinant JAK3 catalytic domain (amino acids 781-1124) expressed and purified from insect cells (Invitrogen, Cat. No. PV3855). The human tyrosine kinase 2 (TYK2) used in the assay is the recombinant TYK2 catalytic domain (amino acids 833-1187) expressed and purified from insect cells (Invitrogen, Cat. No. PV4790). The substrate is a recombinant STAT1 expressed as a fusion with GFP (Green Fluorescent Protein) to act as a physiological substrate (Invitrogen, Cat. No. PV5211).

Test compounds were prepared and diluted in DMSO in 3-fold serial dilutions for 10 doses to 100× of the final testing concentrations. The compounds were then further diluted to 4× by the kinase reaction buffer (Invitrogen, Cat. No. PV3189). The enzymatic reaction for compound testing was performed in a white 384-well polypropylene plate (Packard, Cat. No. 6005214) with a total reaction volume of 10 μL containing 440 ng/mL JAK1, 11 ng/mL JAK2, 400 ng/mL JAK3, or 200 ng/mL TYK2, 100 nM substrate, and 1 mM ATP. The assay started with loading 2.5 μL of JAK1, JAK2, JAK3, or TYK2 diluted in the kinase reaction buffer to wells, followed by addition of an equal volume of 4× compounds for 15-min incubation at room temperature for pre-treatment. The enzymatic reaction was initiated by addition of 5 μL of a mixture of the substrate and ATP prepared in the kinase reaction buffer. After one hour reaction, 10 μL mixture of EDTA (final 10 mM) and terbium-labeled anti-pSTAT1 (pTyr701) antibody (final 2 nM) (Invitrogen, Cat. No. PV4844) prepared in TR-FRET antibody dilution buffer (Invitrogen, Cat. No. PV3574) was added to stop the enzymatic reaction and produce TR-FRET signals. After 30 minutes of incubation at room temperature, the plate was read in Tecan Infinite F200 Pro with the following settings: Excitation 340 nm (30)/Emission1 495 nm (10)/Emission2 520 nm (25). The TR-FRET values were dimensionless numbers that were calculated as the ratio of the acceptor (Green Fluorescent Protein) signal to the donor (Terbium) signal. Percent of inhibition was calculated as (100%–percentage of compound-treated/DMSO vehicle-treated). The dose-response curves were generated and the $IC_{50}$s were calculated by nonlinear sigmoid curve fitting using GraphPad Prism.

The results are summarized in Tables 1 and 2. In Table 1, A represents a value no greater than 500 nM, B represents a value greater than 500 nM but no greater than 1 μM, C represents a value greater than 1 μM but no greater than 5 μM, and D represents a value greater than 5 μM. In Table 2, A' represents a ratio of greater than 8, B' represents a ratio of no greater than 8 but no less than 4, C' represents a ratio of no greater than 4 but no less than 2, and D' represents a ratio of no greater than 2. The selectivity is expressed as a ratio of the $IC_{50}$ values of a compound against two kinases to be compared. For example, the selectivity of a compound for JAK over JAK2 is expressed as a ratio of the $IC_{50}$ value of the compound against JAK2 over by the $IC_{50}$ value against JAK1, and thus the higher the ratio, the more selective the compound is for JAK1.

TABLE 1

| | Inhibitory Activity | | | |
|---|---|---|---|---|
| | $IC_{50}$ | | | |
| Cmpd. | JAK1 | JAK2 | JAK3 | TYK2 |
| 1 | A | C | D | C |
| 3 | C | D | D | D |
| 4 | B | D | D | D |
| 5 | D | D | D | D |
| 6 | C | D | D | D |
| 7 | B | D | D | D |

TABLE 1-continued

| | Inhibitory Activity | | | |
|---|---|---|---|---|
| | $IC_{50}$ | | | |
| Cmpd. | JAK1 | JAK2 | JAK3 | TYK2 |
| 8 | B | D | D | D |
| 9 | C | D | D | D |
| 10 | C | D | D | D |
| 11 | A | D | D | D |
| 12 | C | D | D | D |
| 13 | B | D | D | D |
| 14 | A | C | D | C |
| 16 | A | D | D | D |
| 17 | A | C | D | C |
| 19 | D | D | D | D |
| 20 | D | D | D | D |
| 21 | D | D | D | D |
| 22 | D | D | D | D |
| 23 | B | D | D | D |
| 24 | A | C | D | C |
| 25 | D | D | D | D |
| 26 | A | D | D | D |
| 27 | B | D | D | D |
| 28 | A | B | D | B |
| 29 | D | D | D | D |
| 30 | A | B | D | A |
| 31 | B | D | D | D |
| 32 | A | D | D | D |
| 33 | D | D | D | D |
| 34 | D | D | D | D |
| 35 | D | D | D | D |

TABLE 2

| | Selectivity | | |
|---|---|---|---|
| Cmpd. | JAK2/JAK1 | JAK3/JAK1 | TYK2/JAK1 |
| 1 | A' | A' | A' |
| 3 | A' | A' | A' |
| 4 | A' | A' | A' |
| 5 | A' | A' | A' |
| 6 | A' | A' | A' |
| 7 | A' | A' | A' |
| 8 | A' | A' | A' |
| 9 | A' | A' | A' |
| 10 | A' | A' | A' |
| 11 | A' | A' | A' |
| 12 | A' | A' | A' |
| 13 | A' | A' | A' |
| 14 | A' | A' | A' |
| 16 | A' | A' | A' |
| 17 | A' | A' | A' |
| 19 | A' | D' | C' |
| 20 | C' | B' | C' |
| 21 | A' | A' | C' |
| 22 | A' | A' | A' |
| 23 | A' | A' | A' |
| 24 | A' | A' | A' |
| 25 | A' | A' | A' |
| 26 | A' | A' | A' |
| 27 | A' | A' | A' |
| 28 | A' | A' | A' |
| 29 | C' | A' | C' |
| 30 | A' | A' | B' |
| 31 | A' | A' | A' |
| 32 | A' | A' | A' |
| 33 | A' | A' | A' |
| 34 | ND | ND | ND |
| 35 | ND | ND | ND |

Example B

Cellular Assays for Determining the Inhibition of Janus Kinases

The cellular potency of a compound on JAK or JAK2 inhibition is determined by measuring the cytokine-mediated phosphorylation of STAT proteins in TF-1 cells.

Human cytokines of IL-6 (R&D Systems, Cat. No. 206-IL-010/CF) and GM-CSF (R&D Systems, Cat. No. 215-GM-010/CF) are reconstituted at 10 g/mL in D-PBS containing 0.1% BSA (Sigma, Cat. No. A8577) and human EPO (R&D Systems, Cat. No. 287-TC-500) at 500 U/mL in D-PBS containing 0.1% BSA. TF-1 cells (ATCC, CRL-2003) were grown in RPMI1640 (ATCC, Cat. No. 30-2001) supplemented with 2 ng/mL of recombinant human GM-CSF, 10% FBS (Gibco, Cat. No. 10437-028), and 100 U/mL penicillin-streptomycin (Gibco, Cat. No. 15140-122). The cells were maintained and propagated between $1 \times 10^5$ cells/mL to $7.5 \times 10^5$ cells/mL. Aliquots of the cells from early passages were preserved for liquid nitrogen storage. Frozen vials of the cells were thawed at 37° C. water bath. The cells were spun to remove freezing medium. The newly revived frozen cells were adapted in culture for 5-7 days before used for compound testing. The cells used in for compound testing were less than 20 subculture passages or 3 months in culture.

To test compounds, the TF-1 cells were harvested at a density of 3 to $7 \times 10^5$ cells/mL by centrifugation. After removing the culture medium, the resulting cell pellet was suspended and washed once by centrifugation with HBSS buffer (Gibco, Cat. No. 14025-092) containing 0.1% BSA. The cell pellet was resuspended in HBSS buffer at $7.5 \times 10^6$ cells/mL. Four micro-liters of the cells ($3 \times 10^4$ cells in total) were added to each well of a white 384-well plate (Packard, Cat. No. 6005214).

The compounds were first diluted in dimethylsulfoxide (DMSO) (Sigma, Cat. No. D2650) to generate 9 3-fold diluted dosing concentrations in a 96-well polypropylene plate (Corning, Cat. No. 3365), followed by addition of HBSS buffer for another 125-fold dilution. To the cells, 2 µL of the diluted compounds were added and mixed by tapping the plate several times. The cells were incubated for 2 hrs of treatment. DMSO was used as a control and similarly diluted along and added to the cells.

To assay JAK inhibition, 2 µL of IL-6 diluted at 400 ng/mL (4×) in HBSS containing 0.1% BSA was added to the treated cells. The cells were then incubated for 30 min of cytokine treatment and lysed at the end by addition of 2 µL of 5× AlphaLISA SureFire Ultra lysis buffer from Perkin Elmer. The plate was agitated on a plate shaker for 10 min at room temperature. The cellular JAK activity was determined by measuring STAT3 phosphorylation at Tyr705 in lysates using the AlphaLISA SureFire Ultra kit (Perkin Elmer, Cat. No. ALSU-PST3-A500). A volume of 5 µL of acceptor mix and donor mix was added sequentially to lysates following the product protocol. The assay signals were recorded on EnVision plate reader (Pekin Elmer) with AlphaScreen optics setting.

The results are summarized in Table 3, where A represents a value no greater than 500 nM, B represents a value greater than 500 nM but no greater than 1 µM, C represents a value greater than 1 µM but no greater than 5 µM, and D represents a value greater than 5 µM.

TABLE 3

Inhibitory Activity Agains JAK1

| Cmpd. | IC$_{50}$ |
|---|---|
| 1 | A |
| 14 | A |
| 17 | A |
| 24 | A |
| 26 | A |
| 28 | A |
| 30 | A |

To assay JAK2 inhibition, 2 µL of EPO diluted at 100 U (4×) is added to the compound-treated cells to stimulate downstream STAT5 phosphorylation at Tyr694/699. The cellular JAK2 activity is determined by measuring STAT5 phosphorylation using the AlphaLISA SureFire Ultra kit (Perkin Elmer, Cat. No. ALSU-PST5-A500).

Example C

Human Whole Blood Assays for Determining the Inhibition of Janus Kinases

The potency of compounds on JAK and JAK2 inhibition in human whole blood (HWB) are determined according to the procedures as described in Fridman et al., *J. Immunol.* 2010, 184, 5298-5307; Clark et al., *J. Med. Chem.* 2014, 57, 5023-5038; and Rompaey et al., *J. Immunol.* 2013, 191, 3568-3577.

For example, test compounds are prepared as 30 mM stocks in 100% DMSO and then diluted to 5 mM. A 10-point 2.5 dilution series is created in DMSO with a top concentration of 5 mM. Further dilution is done by adding 4 µL of the solutions into 96 µL of PBS with a top concentration of 200 M. To a 96-well polypropylene plate, 90 µL of HWB is added per well, followed by addition of 5 µL compound solutions to give a top concentration of 10 M. The plate is mixed and incubated for 45 min at 37° C. To each well is added 5 µL of IFNα at the final concentration of 5,000 U/mL, IL-6 at the final concentration of 100 ng/mL, IL-15 at the final concentration of 100 ng/mL, IL-12 at the final concentration of 100 ng/mL, IL-23 at the final concentration of 100 ng/mL, or D-PBS as a control; mixed; and incubated for 15 min at 37° C. The reaction is quenched by adding a lyse/fix buffer to all wells at 1,000 µL/well, and the samples are incubated for 20 min at 37° C. After the samples are washed with a FACS buffer containing 0.1% BSA and 0.1% sodium azide, 400 µL of ice cold 90% methanol/water is added to each well and incubated on ice for 30 min. One more wash is done with cold FACS buffer, and all samples are finally resuspended in 250 µL/well of the desired fluorochrome-labeled anti-phospho-STAT antibody (BD) at 1:125 dilution in the FACS buffer. After overnight incubation at 4° C. all the samples are transferred into a 96-well polypropylene U-bottom plate and STATs phosphorylation are analyzed and quantified using a FACS Canto flow cytometer.

Alternatively, after incubation with compounds at 37° C. for 30 min, HWB is triggered with either recombinant human IL-6 (10 ng/mL), recombinant human IL-2 (4 ng/mL), universal IFN-α (1,000 U/mL; PBL), recombinant human GM-CSF (20 pg/mL), or vehicle (PBS plus 0.1% BSA) at 37° C. for 20 min and treated with prewarmed 1× lysis/fix buffer to lyse RBCs and fix leukocytes. Cells were permeabilized with 100% methanol and incubated with anti-pSTAT1 and anti-CD4 (IL-6- and IFN-α-triggered samples), antipSTAT5 and anti-CD4 Abs (IL-2-triggered samples), or anti-pSTAT5 and anti-CD33 Abs (GM-CSF-triggered samples) at 4° C. for 30 min, washed once with PBS, and analyzed on a FACSCanto II flow cytometer.

Alternatively, in stimulation experiments, test compounds at various concentrations are added for 10 min prior to stimulation with human IL-6 (100 ng/mL) for 15 min at 37° C. RBCs are lysed using hypotonic conditions. WBCs are then quickly pelleted and lysed to make total cellular extracts. The extracts are analyzed for phosphorylated STAT3 by using a phospho-STAT3-specific ELISA.

Example D

Collagen-Induced Arthritis Rat Model

Collagen-induced arthritis (CIA) is an experimental autoimmune disease that can be elicited in susceptible strains of rodents (rats and mice) by immunization with type II collagen (CII). Following immunization, the animals develop an autoimmune-mediated polyarthritis that shares several clinical, histological, and immunological features with human rheumatoid arthritis. See, e.g., Cremer et al., *Curr. Protoc. Immunol.* 1996, 15, 1-24; Kawahito et al., *J. Immunol.* 1998, 161, 4411-4419; Kliwinski et al., *J. Autoimmun.* 2005, 25, 165-171.

A total of 15 femal Lewis rats were obtained from Bejing Vital River Laboratory Animal Co. Ltd. The rats were pathogen free and approximately 5-6 weeks old upon arrival. The rats were immunized intradermally with a total of 0.5 mL CII (Sichuan University)/IFA emulsion (Sigma, Cat. No. F5506) (1 mg bovine type-II collagen) upon arrival (Day 0). The emulsion was injected at 3 sites of each rat, one site at the base of the tail (0.1 mL) and the rest of two sites (0.2 mL/site) on the back and near to the base of the tail. An identical booster injection was given at 7 days after the primary immunization.

For administration, compound 14 was formulated as a suspension using 0.5% sodium carboxymethyl cellulose (Sinopharm Chemical Reagent, Cat. No. 30036365). The compound suspension was prepared freshly for each oral administration.

Thirteen rats were then randomized into two groups using BioBook software to achieve similar mean disease score (about 3) and mean body weights. Group 1 was a control (vehicle) group with five rats and Group 2 is a treatment group with eight rats. Each rat in Group 1 was treated with the vehicle (10 mL/kg) orally (p.o.) and each rat in Group 2 was treated with the compound (10 mL/kg, 10 mg/kg) orally (p.o.) once a day (q.d.). Disease regression was monitored by measuring paw volumes of the hind paws and scoring the severity of arthritis in four paws.

The severity of pathological changes of four paws of the rats was scored before the primary immunization on Day 0 and then 2 times per week starting on Day 7 after sensitization. The criteria for arthritic scoring were: (i) score 0: no evidence of erythema and swelling; (ii) score 1: erythema and mild swelling confined to the mid-foot (tarsals) or ankle joint; (iii) score 2: erythema and mild swelling extending from the ankle to the mid-foot; (iv) score 3: erythema and moderate swelling extending from the ankle to the metatarsal joints; and (v) score 4: erythema and severe swelling encompass the ankle, foot, and digits. The arthritic scores determined for the rats are shown in FIG. 1, where $P<0.05$ is considered statistically significant.

Figure 2:
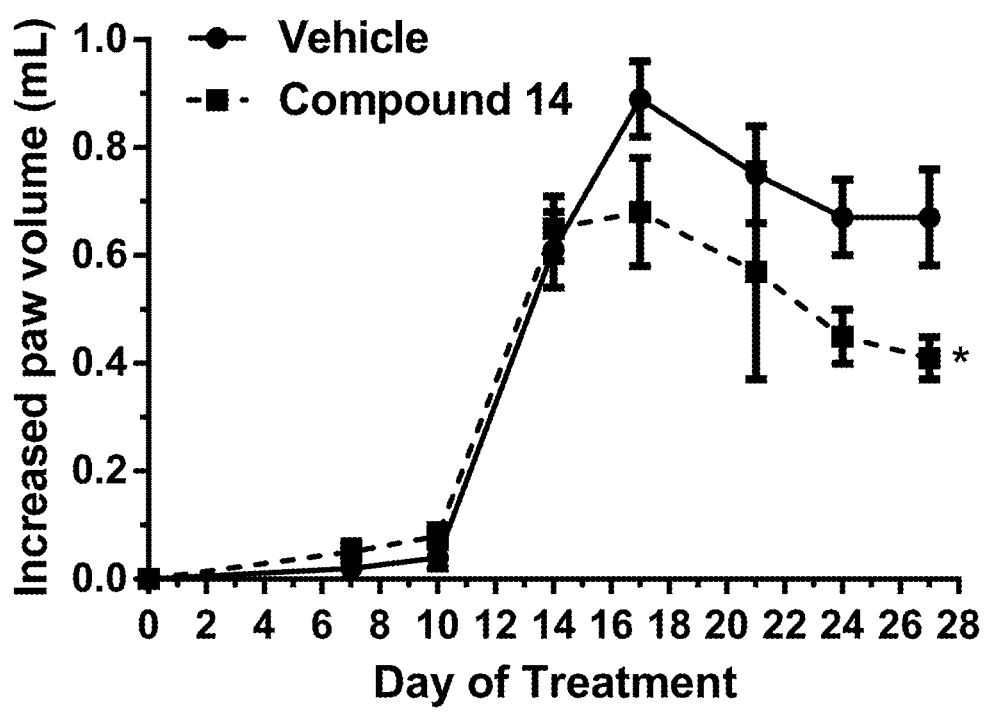
FIG. 2 shows the effect of compound 14 on the increased paw volumes of rats in a collagen-induced arthritis model, where the sign "*" indicates p<0.05.

The volumes of hind paws of the rats were premeasured before the primary immunization on Day 0, and then determined 2 times per week from Day 7 to Day 27 with a Plethysmometer. The changes in volume from baseline measurement (Day 0) were recorded. The increased paw volumes determined for the rats are shown in FIG. 2, where $P<0.05$ is considered statistically significant.

Figure 3:
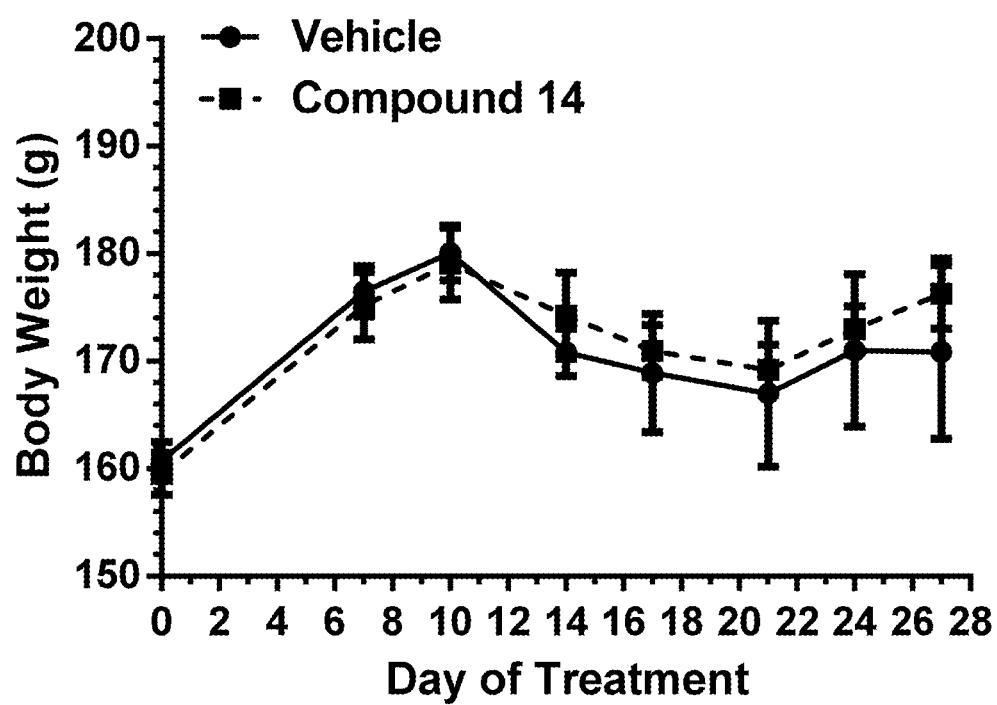
FIG. 3 shows the effect of compound 14 on the body weights of rats in a collagen-induced arthritis rat model.

The body weights of the rats were pre-measured before the primary immunization and then determined 2 times a week from day 7 to day 27. The body weights determined for the rats are shown in FIG. 3.

Example E

Pharmacokinetics

The PK parameters of compound 14 were determined in Sprague-Dawley rats (Hubei Provincial Laboratory Animal Research Center) after a single oral (p.o) and intravenous (i.v.) administration using HPLC-MS/MS (Shimadzu LC-20ACXR HPLC coupled with AB Sciex API 4500 Qtrap).

A sensitive and specific HPLC-MS/MS method was developed for the determination of the compound in rat plasma. Multiple reaction monitoring (MRM) mode was used for the quantification of the compound by monitoring the ion transitions at m/z from 443.1 to 375.1. Compound 2 was used as an internal standard and monitored by the ion transition at m/z from 427.1 to 357.1. Calibration curves were constructed in the range of 1.00-1000 ng/mL in rat plasma extract by a $1/x^2$ weighted quadratic regression. The regression coefficients obtained were greater than 0.99 and back calculated values comprised in the range of ±15% from their nominal concentration. The results are summarized in Table 4 below.

TABLE 4

|    | $t_{1/2}$ (hr) | CL (mL/hr/kg) | $V_z$ (mL/kg) | $AUC_{0-t}$ (hr · ng/mL) | MRT (hr) | $T_{max}$ (hr) | $C_{max}$ (ng/mL) | F (%) |
|----|---|---|---|---|---|---|---|---|
| IV | 1.4 ± 0.3 | 1488 ± 260 | 2984 ± 912 | 677 ± 122 | 1.4 ± 0.2 | | | |
| PO | 1.9 ± 0.3 | | | 1587 ± 253 | 2.3 ± 0.4 | 0.63 ± 0.25 | 571 ± 190 | 46.7 ± 7.3 |

For the intravenous administration, the compound was dissolved in 25% PEG200 in saline and intravenously administrated at a single dose of 1.00 mg/kg. For the oral administration, the compound was suspended in 0.5% sodium carboxymethylcellulose (CMC-Na) solution and intragastrically administrated at a single dose of 5.00 mg/kg. Approximately 0.200 mL of blood sample were collected from orbital venous plexus at 0 (predose), 0.25, 0.5, 1, 2, 4, 8, 12 and 24 hrs post dosing. All samples were placed into EDTA-$K_2$-treated tubes and centrifuged at 3,500 rpm at 4° C. for 10 min to separate the plasma fractions. The plasma samples were stored at −20° C. prior to analysis. The plasma samples were analyzed with the HPLC-MS/MS method.

Example 1

N-(5-(4-((1,1-Dioxo-1-thiomorpholino)methyl)phenyl)imidazo[1,2-a]pyridin-2-yl) cyclopropanecarboxamide 1

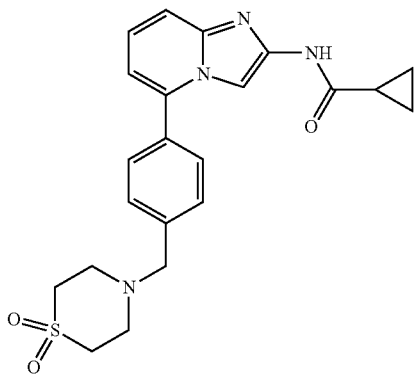

Step 1: tert-Butyl 5-bromoimidazo[1,2-a]pyridin-2-ylcarbamate

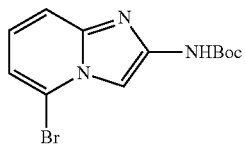 [SMILES: CC(C)(C)OC(=O)Nc1cn2c(Br)cccc2n1]

To a stirred solution of 5-bromoimidazo[1,2-a]pyridine-2-carboxylic acid (1.00 g, 4.15 mmol, 1.0 eq.) in t-BuOH (20 mL) and toluene (20 mL) was added DPPA (1.37 g, 5.00 mmol, 1.2 eq.) at an ice-water bath temperature. Et$_3$N (0.70 mL, 5.00 mmol, 1.2 eq.) was then added dropwise. The resultant mixture was heated to reflux for 14 hrs. TLC indicated the disappearance of 5-bromoimidazo[1,2-a]pyridine-2-carboxylic acid. The crude reaction mixture was concentrated to dryness. The residue was purified by a column chromatography (200-300 mesh silica gel, PE/EA=5/1) to afford tert-butyl 5-bromoimidazo[1,2-a]pyridin-2-ylcarbamate. $^1$H NMR (400 MHz, DMSO-d$_6$) δ (ppm) 10.14 (br, 1H), 7.82 (s, 1H), 7.47 (d, J=8.7 Hz, 1H), 7.24 (d, J=6.8 Hz, 1H), 7.16-7.20 (m, 1H), 1.49 (s, 9H).

Step 2: 5-Bromoimidazo[1,2-a]pyridin-2-amine

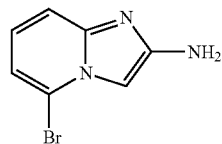 [SMILES: Nc1cn2c(Br)cccc2n1]

To a stirred solution of tert-butyl 5-bromoimidazo[1,2-a]pyridin-2-ylcarbamate (0.70 g, 2.24 mmol, 1.0 eq.) in DCM (30 mL) was added dropwise TFA (10 mL) at an ice-water bath temperature. The resultant mixture was stirred at ambient temperature for 6 hrs. TLC indicated the disappearance of tert-butyl 5-bromoimidazo[1,2-a]pyridin-2-ylcarbamate. The reaction mixture was concentrated to dryness and then treated with water and DCM. The aqueous phase was extracted with DCM twice. The aqueous phase was then treated with 6 N NaOH aqueous solution until pH>9 and extracted with DCM twice. The combined organic phase was dried over Na$_2$SO$_4$ and concentrated to dryness to afford 5-bromoimidazo[1,2-a]pyridin-2-amine. $^1$H NMR (400 MHz, DMSO-d$_6$) δ (ppm) 7.24 (d, J=8.4 Hz, 1H), 7.05 (dd, J=1.1, 6.8 Hz, 1H), 6.97-7.01 (m, 2H), 5.31 (br, 2H).

Step 3: N-(5-Bromoimidazo[1,2-a]pyridin-2-yl)cyclopropanecarboxamide

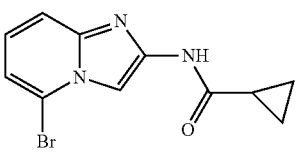 [SMILES: O=C(Nc1cn2c(Br)cccc2n1)C1CC1]

To a stirred solution of 5-bromoimidazo[1,2-a]pyridin-2-amine (0.28 g, 1.32 mmol, 1.0 eq.) in ACN (20 mL) was added dropwise cyclopropanecarboxylic acid chloride (0.48 g, 4.62 mmol, 3.5 eq.), followed by Et$_3$N (0.65 mL, 4.62 mmol, 3.5 eq.) at an ice-water bath temperature. The resultant mixture was stirred at ambient temperature for 24 hrs. TLC indicated the disappearance of 5-bromoimidazo[1,2-a]pyridin-2-amine. Saturated NH$_3$/EtOH (30 mL) was added and the resultant mixture was stirred at ambient temperature for 6 hrs. The crude reaction mixture was concentrated to dryness and the residue was treated with water. Precipitate was collected, dried, and then washed with EA to afford N-(5-bromoimidazo[1,2-a]pyridin-2-yl)cyclopropane carboxamide. $^1$H NMR (400 MHz, DMSO-d$_6$) δ (ppm) 11.14 (br, 1H), 8.05 (s, 1H), 7.50-7.52 (m, 1H), 7.19-7.28 (m, 2H), 1.92-1.99 (m, 1H), 0.82-0.84 (m, 4H).

Step 4: 4-(4-(4,4,5,5-Tetramethyl-1,3,2-dioxaborolan-2-yl)benzyl)-1,1-dioxo-1-thiomorpholine

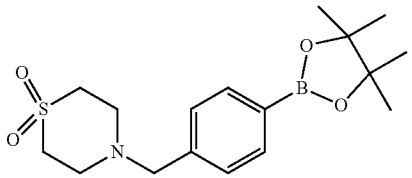 [SMILES: CC1(C)OB(c2ccc(CN3CCS(=O)(=O)CC3)cc2)OC1(C)C]

To a stirred solution of 2-(4-(bromomethyl)phenyl)-4,4,5,5-tetramethyl-1,3,2-dioxaborolane (5.00 g, 16.8 mmol, 0.6 eq.) in MeOH (50 mL) and DCM (150 mL) was added dropwise DIPEA (11.30 g, 87.3 mmol, 3.0 eq.) at an ice-water bath temperature was added dropwise, followed by portionwise addition of 1,1-dioxo-1-thiomorpholine HCl salt (5.00 g, 29.1 mmol, 1.0 eq.). The resultant mixture was stirred at ambient temperature for 16 hrs. TLC indicated the disappearance of 2-(4-(bromomethyl)phenyl)-4,4,5,5-tetramethyl-1,3,2-dioxaborolane. The crude reaction mixture was concentrated to dryness and the resulting residue was treated with water. Precipitate was collected and dried to afford 4-(4-(4,4,5,5-tetramethyl-1,3,2-dioxaborolan-2-yl)

benzyl)-1,1-dioxo-1-thiomorpholine. ¹H NMR (400 MHz, DMSO-d₆) δ (ppm) 7.56 (d, J=7.8 Hz, 2H), 7.35 (d, J=7.8 Hz, 2H), 3.69 (s, 2H), 3.09-3.11 (m, 4H), 2.85-2.86 (m, 4H), 1.29 (s, 12H).

Step 4: N-(5-(4-((1,1-Dioxo-1-thiomorpholino)methyl)phenyl)imidazo[1,2-a]pyridin-2-yl) cyclopropanecarboxamide To a stirred solution of N-(5-bromoimidazo[1,2-a]pyridin-2-yl)cyclopropanecarboxamide (0.17 g, 0.61 mmol, 1.0 eq.) and 2-(4-(bromomethyl)phenyl)-4,4,5,5-tetramethyl-1,3,2-dioxaborolane (0.26 g, 0.73 mmol, 1.2 eq.) in dioxane (30 mL) was added a solution of K₂CO₃ (0.17 g, 1.22 mmol, 2.0 eq.) in water (10 mL), followed by a catalytic amount of Pd(dppf)Cl₂. The resultant mixture was heated to reflux under nitrogen atmosphere for 12 hrs. The reaction mixture was concentrated to dryness and the resulting residue was purified by a column chromatography (200-300 mesh silica gel, DCM/MeOH=20/1) and then further purified using PE/EA to afford N-(5-(4-((1,1-dioxo-1-thiomorpholino)methyl)phenyl)imidazo[1,2-a]pyridin-2-yl) cyclopropanecarboxamide. ¹H NMR (400 MHz, DMSO-d₆) δ (ppm) 11.02 (br, 1H), 7.91 (s, 1H), 7.67-7.68 (m, 2H), 7.56-7.58 (m, 2H), 7.45-7.47 (m, 1H), 7.31-7.35 (m, 1H), 6.86-6.88 (m, 1H), 3.79 (s, 2H), 3.15 (m, 4H), 2.95 (m, 4H), 1.92 (m, 1H), 0.76-0.78 (m, 4H); LC-MS (m/z): 425 [M+H]⁺.

Compounds 2 to 12 in Table 5 were prepared according to the procedures as described in Example 1. NMR spectra data are reported in δ ppm using a 400 MHz spectrometer and DMSO-d₆ as the solvent.

TABLE 5

| Cmpd. | Structure | Characterization |
|---|---|---|
| 2 | 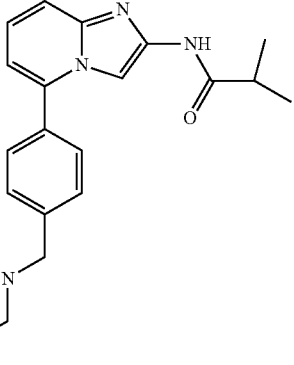 | ¹H NMR (400 MHz, DMSO-d₆) δ (ppm) 10.81 (s, 1H), 8.10 (s, 1H), 7.50 (d, J = 8.7 Hz, 1H), 7.27 (d, J = 7.4 Hz, 1H), 7.19-7.23 (m, 1H), 2.70-2.77 (m, 1H), 1.11 (d, J = 6.8 Hz, 6H); LC-MS (m/z): 427 [M + H]⁺; Purity: >96%. |
| 3 | 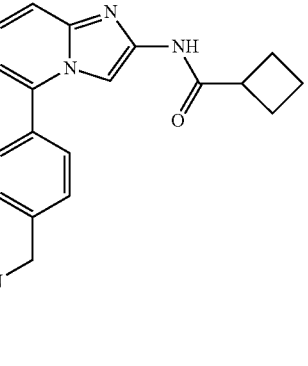 | ¹H NMR (400 MHz, DMSO-d₆) δ (ppm) 10.59 (s, 1H), 7.97 (s, 1H), 7.69-7.71 (m, 2H), 7.58-7.60 (m, 2H), 7.44-7.46 (m, 1H), 7.31-7.35 (m, 1H), 6.86-6.88 (m, 1H), 3.81 (s, 2H), 3.17 (m, 4H), 2.96 (m, 4H), 1.79-2.19 (m, 7H); LC-MS (m/z): 439 [M + H]⁺; Purity: >96%. |
| 4 | 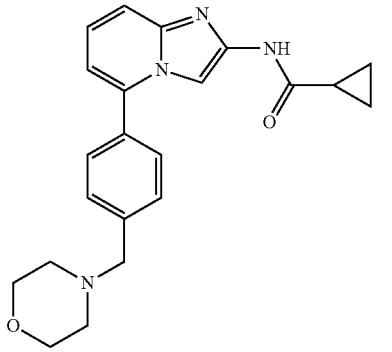 [SMILES: O=C(Nc1cn2c(-c3ccc(CN4CCOCC4)cc3)cccc2n1)C1CC1] | ¹H NMR (400 MHz, DMSO-d₆) δ (ppm) 11.01 (s, 1H), 7.90 (s, 1H), 7.65 (d, J = 7.8 Hz, 2H), 7.54 (d, J = 7.9 Hz, 2H), 7.46 (d, J = 8.9 Hz, 1H), 7.31-7.35 (m, 1H), 6.86 (d, J = 6.8 Hz, 1H), 3.60-3.61 (m, 4H), 3.57 (s, 2H), 2.42 (m, 4H), 1.99 (m, 1H), 0.76-0.78 (m, 4H); LC-MS (m/z): 377 [M + H]⁺; Purity: >96%. |

TABLE 5-continued

| Cmpd. | Structure | Characterization |
|---|---|---|
| 5 | 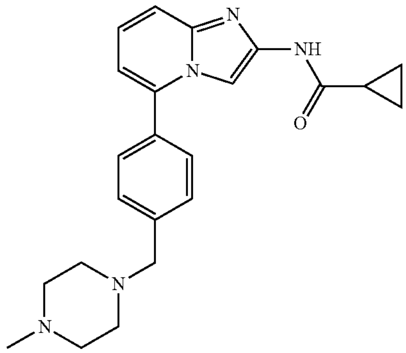 [SMILES: CN1CCN(Cc2ccc(-c3cccc4nc(NC(=O)C5CC5)cn34)cc2)CC1] | $^1$H NMR (400 MHz, DMSO-d$_6$) δ (ppm) 11.01 (s, 1H), 7.90 (s, 1H), 7.65 (d, J = 7.6 Hz, 2H), 7.52 (d, J = 7.3 Hz, 2H), 7.46 (d, J = 8.7 Hz, 1H), 7.31-7.35 (m, 1H), 6.86 (d, J = 6.5 Hz, 1H), 3.57 (s, 2H), 2.33 (m, 8H), 2.21 (s, 3H), 1.92 (m, 1H), 0.76 (m, 4H); LC-MS (m/z): 390 [M + H]$^+$; Purity: >96%. |
| 6 | 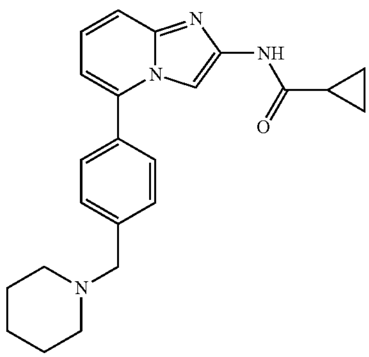 [SMILES: O=C(Nc1cn2c(-c3ccc(CN4CCCCC4)cc3)cccc2n1)C1CC1] | $^1$H NMR (400 MHz, DMSO-d$_6$) δ (ppm) 11.02 (s, 1H), 7.90 (s, 1H), 7.64 (m, 2H), 7.53 (m, 2H), 7.45-7.47 (m, 1H), 7.31-7.35 (m, 1H), 6.86-6.87 (m, 1H), 3.53 (s, 2H), 2.39 (m, 4H), 1.92-1.99 (m, 1H), 1.42-1.35 (m, 6H), 0.76 (m, 4H); LC-MS (m/z): 375 [M + H]$^+$; Purity: >96%. |
| 7 | 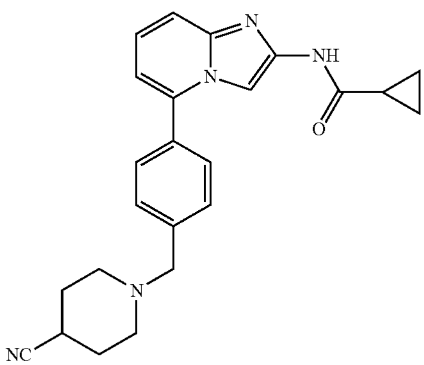 [SMILES: N#CC1CCN(Cc2ccc(-c3cccc4nc(NC(=O)C5CC5)cn34)cc2)CC1] | LC-MS (m/z): 400 [M + H]$^+$; Purity: >96%. |
| 8 | 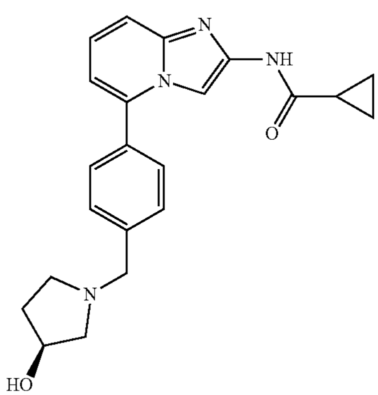 [SMILES: O=C(Nc1cn2c(-c3ccc(CN4CC[C@H](O)C4)cc3)cccc2n1)C1CC1] | LC-MS (m/z): 377 [M + H]$^+$; Purity: >96%. |

TABLE 5-continued

| Cmpd. | Structure | Characterization |
|---|---|---|
| 9 | 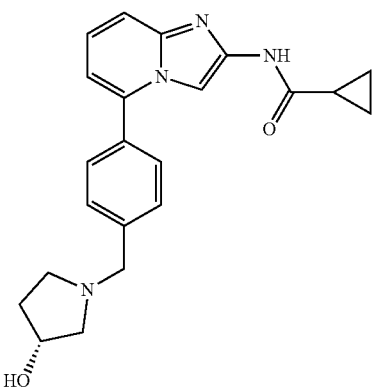 [SMILES: O=C(Nc1cn2c(-c3ccc(CN4CC[C@@H](O)C4)cc3)cccc2n1)C1CC1] | $^1$H NMR (400 MHz, DMSO-$d_6$) δ (ppm) 11.02 (s, 1H), 7.90 (s, 1H), 7.64 (d, J = 7.2 Hz, 2H), 7.53 (d, J = 7.3 Hz, 2H), 7.46 (d, J = 9.0 Hz, 1H), 7.31-7.35 (m, 1H), 6.86 (d, J = 6.6 Hz, 1H), 4.73 (br, 1H), 4.23 (m, 1H), 3.67-3.70 (m, 2H), 2.67-2.74 (m, 2H), 2.33-2.40 (m, 2H), 1.99-2.04 (m, 1H), 1.91 (m, 1H), 1.59 (m, 1H), 0.76 (m, 4H); LC-MS (m/z): 377 [M + H]$^+$; Purity: >96%. |
| 10 | 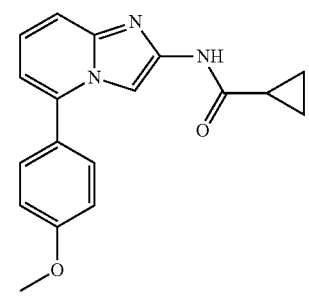 [SMILES: COc1ccc(-c2cccc3nc(NC(=O)C4CC4)cn23)cc1] | $^1$H NMR (400 MHz, DMSO-$d_6$) δ (ppm) 11.00 (s, 1H), 7.89 (s, 1H), 7.62 (d, J = 8.7 Hz, 2H), 7.43 (d, J = 8.9 Hz, 1H), 7.29-7.33 (m, 1H), 7.15 (d, J = 8.7 Hz, 2H), 6.81 (d, J = 6.9 Hz, 1H), 3.86 (s, 3H), 1.90-1.93 (m, 1H), 0.76-0.78 (m, 4H); LC-MS (m/z): 308 [M + H]$^+$; Purity: >96%. |
| 11 | 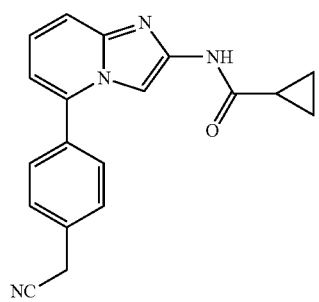 [SMILES: N#CCc1ccc(-c2cccc3nc(NC(=O)C4CC4)cn23)cc1] | $^1$H NMR (400 MHz, DMSO-$d_6$) δ (ppm) 11.02 (s, 1H), 7.86 (s, 1H), 7.73 (d, J = 8.2 Hz, 2H), 7.59 (d, J = 8.1 Hz, 2H), 7.48 (d, J = 8.9 Hz, 1H), 7.32-7.36 (m, 1H), 6.88 (d, J = 6.2 Hz, 1H), 4.18 (s, 2H), 1.90-1.97 (m, 1H), 0.76-0.78 (m, 4H); LC-MS (m/z): 317 [M + H]$^+$; Purity: >96%. |
| 12 | 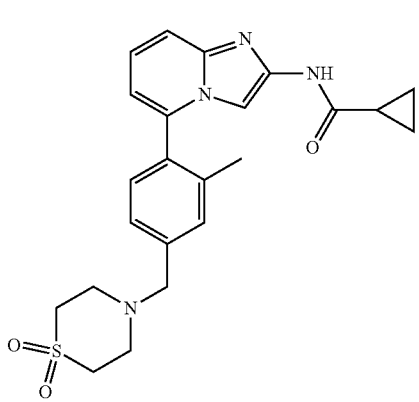 [SMILES: Cc1cc(CN2CCS(=O)(=O)CC2)ccc1-c1cccc2nc(NC(=O)C3CC3)cn12] | $^1$H NMR (400 MHz, DMSO-$d_6$) δ (ppm) 11.04 (br, 1H), 7.48 (d, J = 9.0 Hz, 2H), 7.43 (s, 1H), 7.32-7.38 (m, 3H), 7.27 (s, 1H), 6.81 (d, J = 6.9 Hz, 1H), 3.76 (s, 2H), 3.17 (m, 4H), 2.95 (m, 4H), 2.05 (s, 3H), 1.86-1.92 (m, 1H), 0.82-0.87 (m, 4H); LC-MS (m/z): 439 [M + H]$^+$; Purity: >96%. |

Example 2

N-(5-(4-(1,1-Dioxo-1-thiomorpholine-4-carbonyl)phenyl)imidazo[1,2-a]pyridin-2-yl)cyclopropane carboxamide 13

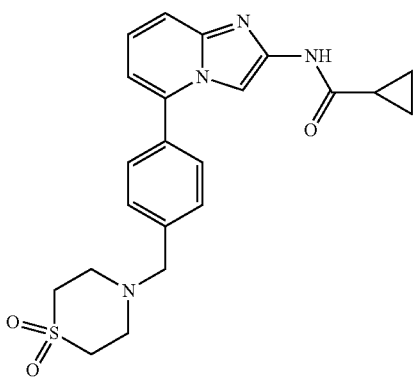

Step 1: (4-Bromophenyl)(1,1-dioxo-1-thiomorpholino)methanone

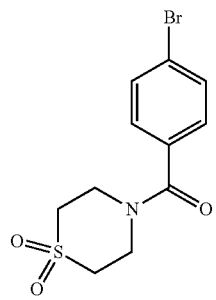 [SMILES: O=C(c1ccc(Br)cc1)N1CCS(=O)(=O)CC1]

To a stirred suspension of 1,1-dioxo-1-thiomorpholine HCl salt (188 mg, 1.1 mmol, 1.2 eq.) in DCM (50 mL) was added 4-bromobenzoyl chloride (200 mg, 0.91 mmol, 1.0 eq.), followed by $Et_3N$ (276 mg, 2.73 mmol, 3.0 eq.). The resultant mixture was stirred at ambient temperature for 16 hrs. TLC indicated the disappearance of 4-bromobenzoyl chloride. The reaction mixture was concentrated to dryness and then treated with water. The resulting precipitates were collected by filtration and dried to afford (4-bromophenyl) (1,1-dioxo-1-thiomorpholino)methanone. $^1$H NMR (400 MHz, DMSO-$d_6$) δ (ppm) 7.67 (d, J=6.3 Hz, 2H), 7.46 (d, J=6.2 Hz, 2H), 3.68-3.98 (m, 4H), 3.25 (m, 4H).

Step 2: N-(5-(4-(1,1-Dioxo-1-thiomorpholine-4-carbonyl)phenyl)imidazo[1,2-a]pyridin-2-yl)cyclopropanecarboxamide To a stirred solution of (4-bromophenyl)(1,1-dioxo-1-thiomorpholino)-methanone (50 mg, 0.16 mmol, 1.2 eq.) and $B_2(pin)_2$ (41 mg, 0.16 mmol, 1.2 eq.) in 1,4-dioxane (10 mL) was added solid $K_2CO_3$ (36 mg, 0.26 mmol, 2.0 eq.), followed by catalytic amount of $Pd(dppf)Cl_2$. The resultant mixture was heated to reflux under nitrogen atmosphere for 16 hrs. TLC indicated the disappearance of (4-bromophenyl) (1,1-dioxo-1-thiomorpholino)methanone. After the reaction mixture was cooled to ambient temperature, N-(5-bromo-imidazo[1,2-a]pyridin-2-yl)cyclopropanecarboxamide (36 mg, 0.13 mmol, 1.0 eq.) was added, followed by a solution of $K_2CO_3$ (36 mg, 0.26 mmol, 2.0 eq.) in water (3 ml). The resultant mixture was heated to reflux under nitrogen atmosphere for 4 hrs. TLC indicated the disappearance of N-(5-bromoimidazo[1,2-a]pyridin-2-yl)cyclopropanecarboxamide. The reaction mixture was concentrated to dryness and the resultant residue was purified by a column chromatography (200-300 mesh silica gel, DCM/MeOH=40/1) to afford N-(5-(4-(1,1-dioxo-1-thiomorpholine-4-carbonyl)phenyl)imidazo[1,2-a]pyridin-2-yl)cyclopropane carboxamide. $^1$H NMR (400 MHz, DMSO-$d_6$) δ (ppm) 11.04 (s, 1H), 7.93 (s, 1H), 7.80 (m, 2H), 7.73 (m, 2H), 7.49-7.51 (m, 1H), 7.35 (m, 1H), 6.92-6.937 (m, 1H), 3.86-4.04 (m, 8H), 1.92 (m, 1H), 0.17 (m, 4H); LC-MS (m/z): 439 [M+H]$^+$.

Compounds 14, 16, and 17 in Table 6 were prepared according to the procedures as described in Examples 2.

TABLE 6

| Cmpd. | Structure | Characterization |
|---|---|---|
| 14 | 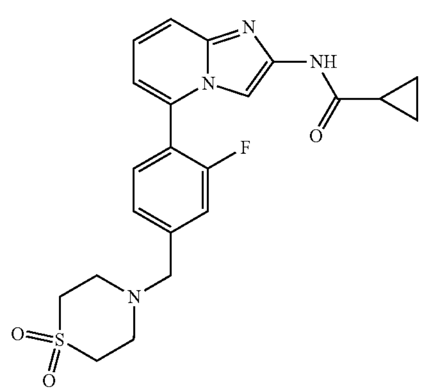 [SMILES: O=C(Nc1cn2c(-c3ccc(CN4CCS(=O)(=O)CC4)cc3F)cccc2n1)C1CC1] | $^1$H NMR (400 MHz, DMSO-$d_6$) δ (ppm) 7.34-7.61 (m, 6H), 6.94 (s, 1H), 3.82 (s, 2H), 3.17 (m, 4H), 2.96 (m, 4H), 1.98 (m, 1H), 0.75 (m, 4H); LC-MS (m/z): 443 [M + H]$^+$; Purity: >96%. |

| Cmpd. | Structure | Characterization |
|---|---|---|
| 16 | 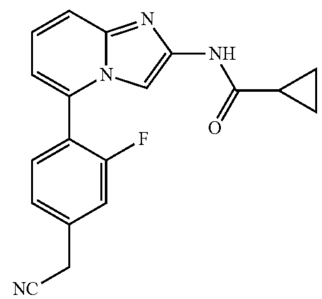 [SMILES: N#CCc1ccc(-c2cccc3nc(NC(=O)C4CC4)cn23)c(F)c1] | $^1$H NMR (400 MHz, DMSO-$d_6$) δ (ppm) 11.05 (br, 1H), 7.70 (m, 1H), 7.46-7.54 (m, 3H), 7.36 (m, 1H), 6.97 (m, 1H), 4.22 (s, 2H), 1.91 (m, 1H), 0.76 (m, 4H); LC-MS (m/z): 335 [M + H]$^+$; Purity: >96%. |
| 17 | 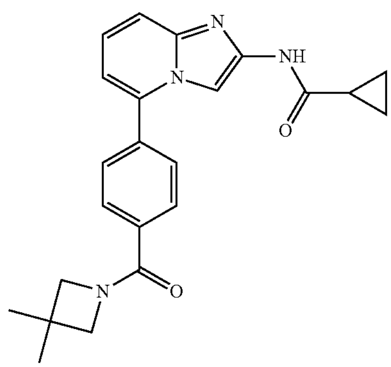 [SMILES: CC1(C)CN(C(=O)c2ccc(-c3cccc4nc(NC(=O)C5CC5)cn34)cc2)C1] | $^1$H NMR (400 MHz, DMSO-$d_6$) δ (ppm) 11.06 (s, 1H), 7.91 (s, 1H), 7.84-7.87 (d, 2H), 7.77-7.79 (d, 2H), 7.49-7.52 (d, 1H), 7.34-7.38 (t, 1H), 6.91-6.93 (d, 1H), 4.08 (s, 2H), 3.78 (s, 2H), 1.92 (m, 1H), 1.28 (s, 6H), 0.77-0.79 (m, 4H); LC-MS (m/z): 389 [M + H]$^+$; Purity: >96%. |

Example 3

5-(2-Fluoro-4-(1,1-dioxo-1-thiomorpholinomethyl)phenyl) imidazo[1,2-a]pyridin-2-amine 18

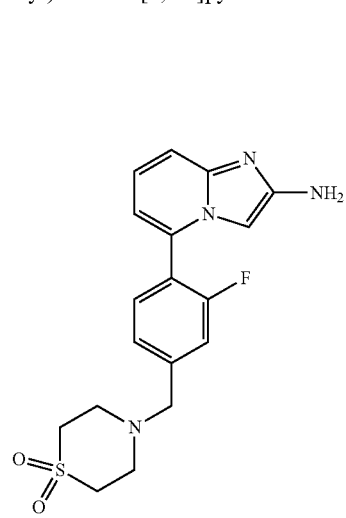

Step 1: 4-(4-Bromo-3-fluorobenzyl)-1,1-dioxo-1-thiomorpholine

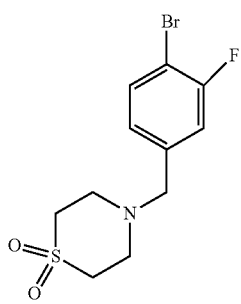 [SMILES: O=S1(=O)CCN(Cc2ccc(Br)c(F)c2)CC1]

To a stirred solution of 1,1-dioxo-1-thiomorpholine HCl salt (100 mg, 0.58 mmol, 1.0 eq.) in DCM (30 mL) and MeOH (10 mL) was added DIPEA (225 mg, 1.74 mmol, 3.0 eq.). The resultant mixture was stirred at ambient temperature for 10 mins. 1-Bromo-4-(bromomethyl)-2-fluorobenzene (94 mg, 0.35 mmol, 0.6 eq.) in DCM (3 mL) was added. The resultant mixture was heated to reflux for 8 hrs. TLC indicated the disappearance of 1-bromo-4-(bromomethyl)-2-fluorobenzene. The crude reaction mixture was concentrated to dryness, and the resultant residue was treated with water. The mixture was extracted with EA, dried over $Na_2SO_4$, and concentrated to dryness to afford 4-(4-bromo-3-fluorobenzyl)-1,1-dioxo-1-thiomorpholine (88 mg, 78% yield), which was used directly in next step without further purification.

Step 2: 5-(2-Fluoro-4-(1,1-dioxo-1-thiomorpholinomethyl)phenyl)imidazo[1,2-a]pyridin-2-amine To a stirred solution of 4-(4-bromo-3-fluorobenzyl)-1,1-dioxo-1-thiomorpholine (42 mg, 0.13 mmol, 1 eq.) and $B_2(pin)_2$ (41 mg, 0.16 mmol, 1.2 eq.) in 1,4-dioxane (10 mL) was added solid $K_2CO_3$ (36 mg, 0.26 mmol, 2.0 eq.), followed by a catalytic amount of $Pd(dppf)Cl_2$. The resultant mixture was heated to reflux under nitrogen atmosphere for 16 hrs. TLC indicated the disappearance of 4-(4-bromo-3-fluorobenzyl)-1,1-dioxo-1-thiomorpholine. After the reaction mixture was cooled to ambient temperature, tert-butyl 5-bromoimidazo[1,2-a]pyridin-2-ylcarbamate (41 mg, 0.13 mmol, 1.0 eq.) was added, followed by a solution of $K_2CO_3$ (36 mg, 0.26 mmol, 2.0 eq.) in water (3 mL). The resultant mixture was heated to reflux under nitrogen atmosphere for 4 hrs. TLC indicated the disappearance of tert-butyl 5-bromoimidazo[1,2-a]pyridin-2-ylcarbamate. The reaction mixture was concentrated to dryness. The residue was taken up with DCM and washed with brine. The aqueous layer was extracted with DCM. The combined organic layers were dried ($Na_2SO_4$) and concentrated to give tert-butyl 5-(2-fluoro-4-(1,1-dioxo-1-thiomorpholinomethyl)phenyl)imidazo[1,2-a]pyridin-2-ylcarbamate as a yellow residue. The residue was dissolved into 1 mL of DCM and 0.3 mL of TFA was added at an ice-water temperature. The solution was stirred for 6 hrs at ambient temperature. The solution was diluted with DCM and washed with 1N NaOH. The aqueous layer was extracted with DCM. The combined organic layers were dried ($Na_2SO_4$), concentrated, and purified by a column chromatography (200-300 mesh silica gel, DCM/MeOH=30/1) to afford 5-(2-fluoro-4-(1,1-dioxo-1-thiomorpholinomethyl)-phenyl)imidazo[1,2-a]pyridin-2-amine (6 mg, 13%). $^1H$ NMR (400 MHz, DMSO-$d_6$) δ (ppm) 7.34-7.61 (m, 6H), 6.94 (s, 1H), 6.12 (bs, 2H), 3.82 (s, 2H), 3.17 (m, 4H), 2.96 (m, 4H), 1.98 (m, 1H), 0.75 (m, 4H); LC-MS (m/z): 343 [M+H]+.

Compounds 20 to 35 in Table 7 were prepared according to an procedures as described in Examples 1 to 3.

TABLE 7

| Cmpd. | Structure | Characterization |
|---|---|---|
| 20 | 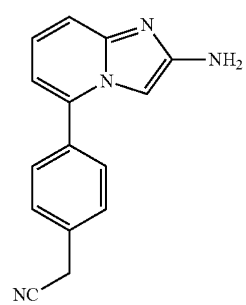 [SMILES: N#CCc1ccc(-c2cccc3nc(N)cn23)cc1] | $^1H$ NMR (400 MHz, DMSO-$d_6$) δ (ppm) 7.73-7.78 (m, 3H), 7.67-7.69 (d, 2H), 7.60-7.62 (d, 1H), 7.27-7.29 (d, 2H), 4.09 (s, 2H); LC-MS (m/z): 250 [M + H]+; Purity: >96%. |
| 21 | 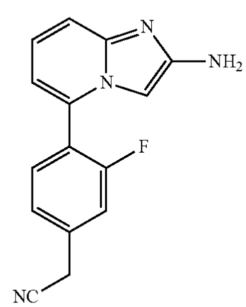 [SMILES: N#CCc1ccc(-c2cccc3nc(N)cn23)c(F)c1] | $^1H$ NMR (400 MHz, DMSO-$d_6$) δ (ppm) 7.66-7.70 (t, 1H), 7.42-7.49 (m, 2H), 7.28-7.30 (d, 1H), 7.12-7.16 (m, 1H), 6.76-6.78 (d, 1H), 6.48-6.49 (d, 1H), 5.07 (s, 2H), 4.22 (s, 2H); LC-MS (m/z): 267 [M + H]+; Purity: >96%. |
| 22 | 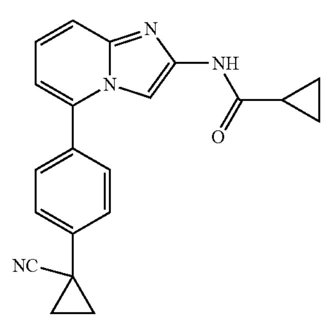 [SMILES: N#CC1(c2ccc(-c3cccc4nc(NC(=O)C5CC5)cn34)cc2)CC1] | $^1H$ NMR (400 MHz, DMSO-$d_6$) δ (ppm) 11.04 (s, 1H), 7.87 (s, 1H), 7.72-7.74 (d, 2H), 7.55-7.57 (d, 2H), 7.47-7.49 (d, 1H), 7.32-7.36 (t, 1H), 6.87-6.88 (d, 1H), 1.91-1.93 (m, 1H), 1.83-1.86 (m, 2H), 1.64-1.68 (m, 2H), 0.77-0.79 (m, 4H); LC-MS (m/z): 342 [M + H]+; Purity: >96%. |

TABLE 7-continued

| Cmpd. | Structure | Characterization |
| --- | --- | --- |
| 23 | 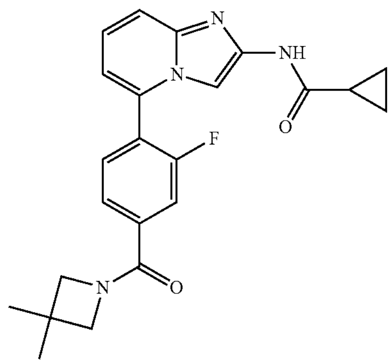 [SMILES: CC1(C)CN(C(=O)c2ccc(-c3cccc4nc(NC(=O)C5CC5)cn34)c(F)c2)C1] | $^1$H NMR (400 MHz, DMSO-d$_6$) δ (ppm) 11.09 (s, 1H), 7.68-7.75 (m, 2H), 7.56-7.58 (m, 2H), 7.35-7.39 (m, 2H), 6.99-7.01 (d, 1H), 4.10 (s, 2H), 3.79 (s, 2H), 1.92 (m, 1H), 1.24-1.28 (m, 6H), 0.77-0.79 (m, 4H); LC-MS (m/z): 407 [M + H]$^+$; Purity: 96%. |
| 24 | 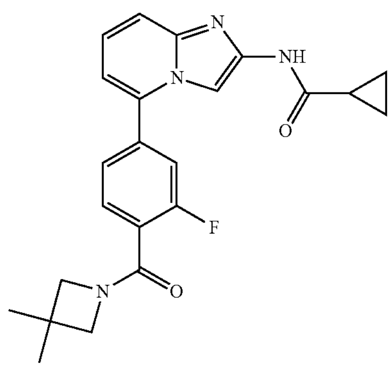 [SMILES: CC1(C)CN(C(=O)c2ccc(-c3cccc4nc(NC(=O)C5CC5)cn34)cc2F)C1] | $^1$H NMR (400 MHz, DMSO-d$_6$) δ (ppm) 11.08 (s, 1H), 7.92 (s, 1H), 7.70-7.76 (m, 2H), 7.64-7.66 (d, 1H), 7.52-7.54 (d, 1H), 7.34-7.38 (t, 1H), 6.96-6.98 (d, 1H), 3.77 (s, 4H), 1.93 (m, 1H), 1.27 (s, 6H), 0.78-0.80 (m, 4H); LC-MS (m/z): 407 [M + H]$^+$; Purity: >96%. |
| 25 | 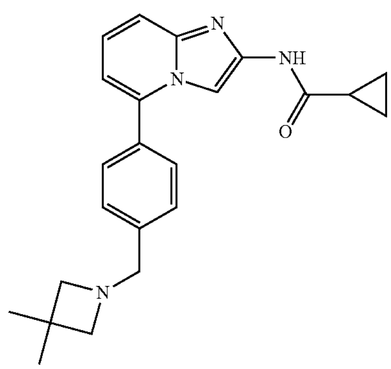 [SMILES: CC1(C)CN(Cc2ccc(-c3cccc4nc(NC(=O)C5CC5)cn34)cc2)C1] | $^1$H NMR (400 MHz, DMSO-d$_6$) δ (ppm) 11.01 (s, 1H), 7.89 (s, 1H), 7.61-7.63 (d, 2H), 7.45-7.49 (m, 3H), 7.31-7.35 (t, 1H), 6.84-6.86 (d, 1H), 3.66 (s, 2H), 2.96 (s, 4H), 1.89-1.93 (m, 1H), 1.21 (s, 6H), 0.76-0.78 (m, 4H); LC-MS (m/z): 375 [M + H]$^+$; Purity: >96%. |
| 26 | 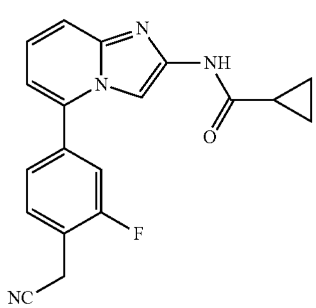 [SMILES: N#CCc1ccc(-c2cccc3nc(NC(=O)C4CC4)cn23)cc1F] | $^1$H NMR (400 MHz, DMSO-d$_6$) δ (ppm) 11.05 (s, 1H), 7.87 (s, 1H), 7.68-7.72 (m, 2H), 7.60-7.62 (d, 1H), 7.50-7.52 (d, 1H), 7.33-7.37 (m, 1H), 6.93-6.94 (d, 1H), 4.20 (s, 2H), 1.89-1.95 (m, 1H), 0.77-0.79 (m, 4H); LC-MS (m/z): 355 [M + H]$^+$; Purity: >96%. |

TABLE 7-continued

| Cmpd. | Structure | Characterization |
| --- | --- | --- |
| 27 | 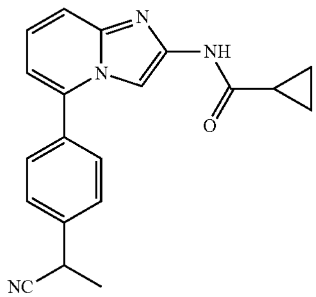 [SMILES: CC(C#N)c1ccc(-c2cccc3nc(NC(=O)C4CC4)cn23)cc1] | $^1$H NMR (400 MHz, DMSO-d$_6$) δ (ppm) 11.03 (s, 1H), 7.88 (s, 1H), 7.75-7.77 (d, 2H), 7.65-7.67 (d, 2H), 7.47-7.50 (d, 1H), 7.33-7.37 (t, 1H), 6.88-6.90 (d, 1H), 4.43-4.48 (q, 1H), 1.89-1.93 (m, 1H), 1.63-1.65 (d, 3H), 0.77-0.79 (m, 4H); LC-MS (m/z): 331 [M + H]$^+$; Purity: >96%. |
| 28 | 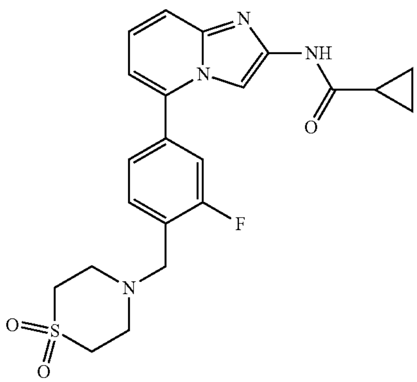 [SMILES: O=C(Nc1cn2c(-c3ccc(CN4CCS(=O)(=O)CC4)c(F)c3)cccc2n1)C1CC1] | $^1$H NMR (400 MHz, DMSO-d$_6$) δ (ppm) 11.04 (s, 1H), 7.92 (s, 1H), 7.69-7.73 (t, 1H), 7.56-7.61 (m, 2H), 7.49-7.51 (d, 1H), 7.32-7.36 (t, 1H), 6.92-6.94 (d, 1H), 3.85 (s, 2H), 3.16-3.17 (m, 4H), 2.99 (m, 4H), 1.89-1.96 (m, 1H), 0.77-0.79 (m, 4H); LC-MS (m/z): 443 [M + H]$^+$; Purity: >96%. |
| 29 | 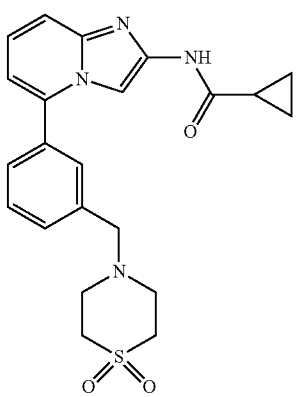 [SMILES: O=C(Nc1cn2c(-c3cccc(CN4CCS(=O)(=O)CC4)c3)cccc2n1)C1CC1] | $^1$H NMR (400 MHz, DMSO-d$_6$) δ (ppm) 11.03 (s, 1H), 7.96 (s, 1H), 7.76 (s, 1H), 7.56-7.60 (m, 2H), 7.47-7.52 (m, 2H), 7.33-7.37 (m, 1H), 6.90-6.91 (d, 1H), 3.76 (s, 2H), 3.13-3.14 (m, 4H), 2.93 (m, 4H), 1.89-1.95 (m, 1H), 0.77-0.78 (m, 4H); LC-MS (m/z): 425 [M + H]$^+$; Purity: >96%. |
| 30 | 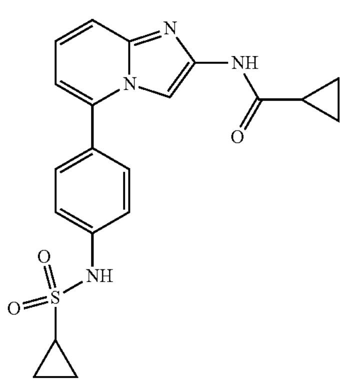 [SMILES: O=C(Nc1cn2c(-c3ccc(NS(=O)(=O)C4CC4)cc3)cccc2n1)C1CC1] | $^1$H NMR (400 MHz, DMSO-d$_6$) δ (ppm) 11.02 (s, 1H), 10.13 (s, 1H), 7.90 (s, 1H), 7.66-7.68 (d, 2H), 7.43-7.46 (m, 3H), 7.31-7.35 (m, 1H), 6.84-6.85 (d, 1H), 2.75-2.81 (m, 1H), 1.89-1.95 (m, 1H), 1.00-1.03 (m, 4H), 0.77-0.79 (m, 4H); LC-MS (m/z): 397 [M + H]$^+$; Purity: >96%. |

TABLE 7-continued

| Cmpd. | Structure | Characterization |
|---|---|---|
| 31 | 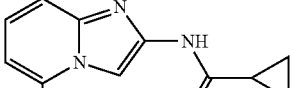 | $^{1}$H NMR (400 MHz, DMSO-$d_6$) δ (ppm) 11.04 (s, 1H), 8.85-8.88 (t, 1H), 7.87 (s, 1H), 7.66-7.68 (d, 2H), 7.46-7.50 (m, 3H), 7.32-7.36 (m, 1H), 6.85-6.87 (d, 1H), 4.42-4.44 (d, 2H), 3.36-3.42 (m, 2H), 1.88-1.94 (m, 1H), 0.77-0.80 (m, 4H); LC-MS (m/z): 363 [M + H]$^+$; Purity: >96%. |
| 32 | 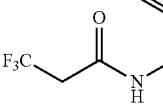 | $^{1}$H NMR (400 MHz, DMSO-$d_6$) δ (ppm) 11.04 (s, 1H), 7.90 (s, 1H), 7.59-7.66 (m, 4H), 7.44-7.47 (d, 1H), 7.30-7.34 (t, 1H), 7.18-7.21 (d, 1H), 7.08-7.12 (t, 1H), 6.84-6.86 (d, 1H), 6.55-6.64 (m, 2H), 6.12-6.15 (t, 1H), 4.49-4.50 (d, 2H), 3.94 (s, 2H), 1.88-1.94 (m, 1H), 0.76-0.80 (m, 4H); LC-MS (m/z): 422 [M + H]$^+$; Purity: >96%. |
| 33 | 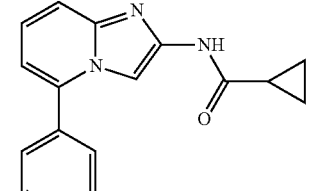 | $^{1}$H NMR (400 MHz, DMSO-$d_6$) δ (ppm) 10.96 (s, 1H), 7.81 (s, 1H), 7.66-7.68 (d, 2H), 7.56-7.58 (d, 2H), 7.25 (s, 1H), 6.74 (s, 1H), 3.79 (s, 2H), 3.15-3.16 (m, 4H), 2.96 (m, 4H), 2.39 (s, 3H), 1.87-1.93 (m, 1H), 0.75-0.77 (m, 4H); LC-MS (m/z): 439 [M + H]$^+$; Purity: >96%. |
| 34 | 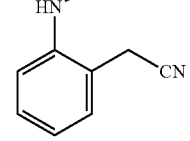 | $^{1}$H NMR (400 MHz, DMSO-$d_6$) δ (ppm) 11.06 (s, 1H), 7.61-7.63 (d, 2H), 7.52-7.56 (m, 3H), 7.44-7.46 (d, 2H), 3.84 (s, 2H), 3.17-3.18 (m, 4H), 2.98 (m, 4H), 1.86-1.92 (m, 1H), 0.75-0.78 (m, 4H); LC-MS (m/z): 459 [M + H]$^+$; Purity: >96%. |

TABLE 7-continued

| Cmpd. | Structure | Characterization |
|---|---|---|
| 35 | 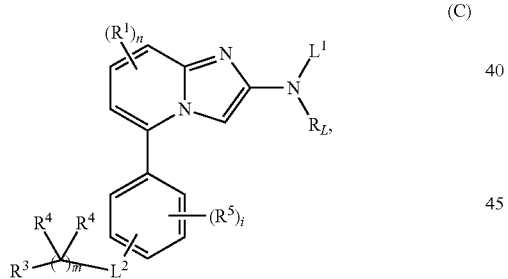 | $^1$H NMR (400 MHz, DMSO-$d_6$) δ (ppm) 11.18 (s, 1H), 7.90 (s, 1H), 7.64-7.66 (d, 2H), 7.55-7.57 (d, 2H), 7.16-7.18 (d, 1H), 6.79-6.81 (d, 1H), 3.79 (s, 2H), 3.16 (m, 4H), 2.96 (m, 4H), 1.87-1.91 (m, 1H), 0.75-0.76 (m, 4H); LC-MS (m/z): 439 [M + H]$^+$; Purity: >96%. |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such a publication, patent, or patent application were specifically and individually indicated to be incorporated herein by reference.

What is claimed is:

1. A compound of formula (C):

(C)

or a single enantiomer, a racemic mixture, a mixture of diastereomers, or an isotopic variant thereof; or a pharmaceutically acceptable salt or solvate thereof;
wherein:
  $L^1$ is —C(O)$R^2$;
  $L^2$ is a single bond, —O—, —NR$^6$—, —C(O)—, —C(O)O—, —OC(O)—, —CONR$^6$—, —NR$^6$CO—, —S(O)$_2$—, —NR$^6$SO$_2$—, or —SO$_2$NR$^6$—;
  m is an integer of 0, 1, 2, 3, 4, 5, or 6;
  n is an integer of 0, 1, 2, or 3;
  i is an integer of 1, 2, 3, or 4;
  $R^1$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)$R^{1a}$, —C(O)O$R^{1a}$, —C(O)NR$^{1b}$R$^{1c}$, —C(NR$^{1a}$)NR$^{1b}$R$^{1c}$, —OR$^{1a}$, —OC(O)$R^{1a}$, —OC(O)OR$^{1a}$, —OC(O)NR$^{1b}$R$^{1c}$, —OC(=NR$^{1a}$)NR$^{1b}$R$^{1c}$, —OS(O)$R^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)$R^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)$R^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)$R^{1a}$, —S(O)$_2$R$^{1a}$, —S(O)NR$^{1b}$R$^{1c}$, or —S(O)$_2$NR$^{1b}$R$^{1c}$;
  $R^2$ is $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl;
  $R^3$ is (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)$R^{1a}$, —C(O)O$R^{1a}$, —C(O)NR$^{1b}$R$^{1c}$, —C(NR$^{1a}$)NR$^{1b}$R$^{1c}$, —OR$^{1a}$, —OC(O)$R^{1a}$, —OC(O)OR$^{1a}$, —OC(O)NR$^{1b}$R$^{1c}$, —OC(=NR$^{1a}$)NR$^{1b}$R$^{1c}$, —OS(O)$R^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)$R^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)$R^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)$R^{1a}$, —S(O)$_2$R$^{1a}$, —S(O)NR$^{1b}$R$^{1c}$, or —S(O)$_2$NR$^{1b}$R$^{1c}$;
  $R^4$ at each occurrence is independently (a) hydrogen, cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)$R^{1a}$, —C(O)O$R^{1a}$, —C(O)NR$^{1b}$R$^{1c}$, —C(NR$^{1a}$)NR$^{1b}$R$^{1c}$, —OR$^{1a}$, —OC(O)$R^{1a}$, —OC(O)OR$^{1a}$, —OC(O)NR$^{1b}$R$^{1c}$, —OC(=NR$^{1a}$)NR$^{1b}$R$^{1c}$, —OS(O)$R^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)$R^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)$R^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)$R^{1a}$, —S(O)$_2$R$^{1a}$, —S(O)NR$^{1b}$R$^{1c}$, or —S(O)$_2$NR$^{1b}$R$^{1c}$; or two $R^4$ groups together with the C atom to which they are attached form $C_3$-$C_{10}$ cycloalkyl or heterocyclyl;
  $R^5$ at each occurrence is independently (a) cyano, halogen, or nitro; (b) $C_1$-$C_8$ alkyl, $C_2$-$C_8$ alkenyl, $C_2$-$C_8$ alkynyl, $C_3$-$C_{10}$ cycloalkyl, $C_6$-$C_{10}$ aryl, heteroaryl, or heterocyclyl; or (c) —C(O)$R^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^6$ at each occurrence is independently hydrogen, C$_1$-C$_8$ alkyl, C$_2$-C$_8$ alkenyl, C$_2$-C$_8$ alkynyl, C$_3$-C$_{10}$ cycloalkyl, C$_6$-C$_{10}$ aryl, heteroaryl, or heterocyclyl;

R$^L$ is hydrogen, C$_1$-C$_8$ alkyl, C$_2$-C$_8$ alkenyl, C$_2$-C$_8$ alkynyl, C$_3$-C$_{10}$ cycloalkyl, C$_6$-C$_{10}$ aryl, heteroaryl, or heterocyclyl; and each R$^{1a}$, R$^{1b}$, R$^{1c}$, and R$^{1d}$ is independently hydrogen, C$_1$-C$_8$ alkyl, C$_2$-C$_8$ alkenyl, C$_2$-C$_8$ alkynyl, C$_3$-C$_{10}$ cycloalkyl, C$_6$-C$_{10}$ aryl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

wherein each alkyl, alkenyl, alkynyl, cycloalkyl, aryl, heteroaryl, and heterocyclyl is optionally substituted with one or more substituents Q, where each Q is independently selected from (a) oxo, cyano, halogen, and nitro; (b) C$_1$-C$_8$ alkyl, C$_2$-C$_8$ alkenyl, C$_2$-C$_8$ alkynyl, C$_3$-C$_{10}$ cycloalkyl, C$_6$-C$_{10}$ aryl, heteroaryl, and heterocyclyl, each of which is further optionally substituted with one or more substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —S(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, where each R$^a$, R$^b$, R$^c$, and R$^d$ is independently (i) hydrogen; (ii) C$_1$-C$_8$ alkyl, C$_2$-C$_8$ alkenyl, C$_2$-C$_8$ alkynyl, C$_3$-C$_{10}$ cycloalkyl, C$_6$-C$_{10}$ aryl, heteroaryl, or heterocyclyl, each of which is optionally substituted with one or more substituents Q$^a$; or (iii) R$^b$ and R$^c$ together with the N atom to which they are attached form heterocyclyl, optionally substituted with one or more substituents Q$^a$;

wherein each Q$^a$ is independently selected from the group consisting of (a) oxo, cyano, halogen, and nitro; (b) C$_1$-C$_8$ alkyl, C$_2$-C$_8$ alkenyl, C$_2$-C$_8$ alkynyl, C$_3$-C$_{10}$ cycloalkyl, C$_6$-C$_{10}$ aryl, heteroaryl, and heterocyclyl; and (c) —C(O)R$^f$, —C(O)OR$^f$, —C(O)NR$^g$R$^h$, —C(NR$^f$)NR$^g$R$^h$, —OR$^f$, —OC(O)R$^f$, —OC(O)OR$^f$, —OC(O)NR$^g$R$^h$, —OC(=NR$^f$)NR$^g$R$^h$, —OS(O)R$^f$, —OS(O)$_2$R$^f$, —OS(O)NR$^g$R$^h$, —OS(O)$_2$NR$^g$R$^h$, —NR$^g$R$^h$, —NR$^f$C(O)R$^k$, —NR$^f$C(O)OR$^k$, —NR$^f$C(O)NR$^g$R$^h$, —NR$^f$C(=NR$^k$)NR$^g$R$^h$, —NR$^f$S(O)R$^k$, —NR$^f$S(O)$_2$R$^k$, —NR$^f$S(O)NR$^g$R$^h$, —NR$^f$S(O)$_2$NR$^g$R$^h$, —SR$^f$, —S(O)R$^f$, —S(O)$_2$R$^f$, —S(O)NR$^g$R$^h$, and —S(O)$_2$NR$^g$R$^h$; where each R$^f$, R$^g$, R$^h$, and R$^k$ is independently (i) hydrogen; (ii) C$_1$-C$_8$ alkyl, C$_2$-C$_8$ alkenyl, C$_2$-C$_8$ alkynyl, C$_3$-C$_{10}$ cycloalkyl, C$_6$-C$_{10}$ aryl, heteroaryl, and heterocyclyl; or (iii) R$^g$ and R$^h$ together with the N atom to which they are attached form heterocyclyl.

2. The compound of claim 1, wherein the compound is a compound of formula (D):

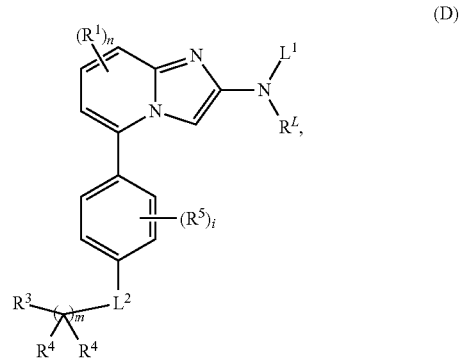

(D)

or a single enantiomer, a racemic mixture, a mixture of diastereomers, or an isotopic variant thereof; or a pharmaceutically acceptable salt or solvate thereof.

3. The compound of claim 1, wherein the compound is a compound of formula (E):

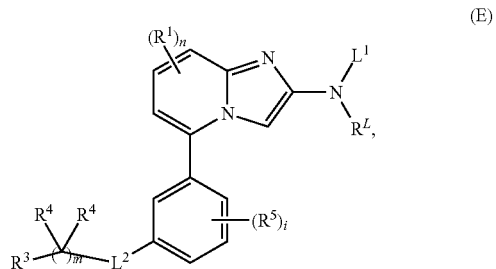

(E)

or a single enantiomer, a racemic mixture, a mixture of diastereomers, or an isotopic variant thereof; or a pharmaceutically acceptable salt or solvate thereof.

4. The compound of claim 1, wherein R$^L$ is hydrogen.

5. The compound of claim 1, wherein R$^2$ is C$_1$-C$_8$ alkyl, C$_3$-C$_{10}$ cycloalkyl, or heterocyclyl; each of which is optionally substituted with one or more substituents Q.

6. The compound of claim 5, wherein R$^2$ is C$_3$-C$_{10}$ cycloalkyl, optionally substituted with one or more substituents Q.

7. The compound of claim 6, wherein R$^2$ is cyclopropyl or cyclobutyl, each of which is optionally substituted with one or more substituents Q.

8. The compound of claim 1, wherein n is an integer of 0 or 1.

9. The compound of claim 1, wherein R$^1$ is halogen or C$_1$-C$_8$ alkyl, where the alkyl is optionally substituted with one or more substituents Q.

10. The compound of claim 9, wherein R$^1$ is chloro or methyl.

11. The compound of claim 1, wherein R$^3$ is (a) cyano; (b) heterocyclyl, which is optionally substituted with one or more substituents Q; (c) —NR$^{1b}$R$^{1c}$, —NR$^{1a}$C(O)R$^{1d}$, —OR$^{1a}$, or —NR$^{1a}$S(O)$_2$R$^{1d}$.

12. The compound of claim 11, wherein R$^3$ is heterocyclyl, optionally substituted with one or more substituents Q.

13. The compound of claim 12, wherein R$^3$ is azetidinyl, pyrrolidinyl, piperidinyl, piperazinyl, morpholino, or thiomorpholino, each of which is optionally substituted with one or more substituents Q.

14. The compound of claim 11, wherein $R^3$ is cyano, cyanomethylphenylamino, 3,3,3-trifluoropropanamido, hydroxypyrrolidinyl, piperidinyl, cyanopiperidinyl, morpholino, methyl-piperazinyl, 1,1-dioxidothiomorpholino, methoxy, dimethylazetidinyl, or cyclopropanesulfonamido.

15. The compound of claim 1, wherein $L^2$ is a single bond; m is an integer of 1; and $R^4$ at each occurrence is hydrogen.

16. The compound of claim 1, wherein i is an integer of 1.

17. The compound of claim 16, wherein $R^5$ is halogen or $C_1$-$C_8$ alkyl, where the alkyl is optionally substituted with one or more substituents Q.

18. The compound of claim 17, wherein $R^5$ is fluoro, chloro, or methyl.

19. A compound selected from:

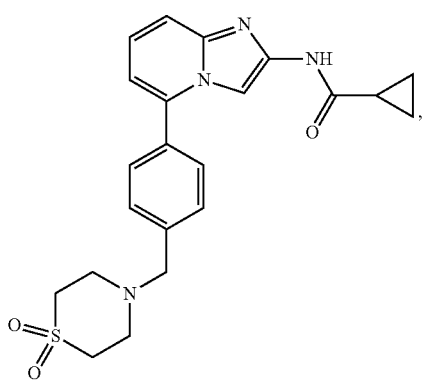
1,

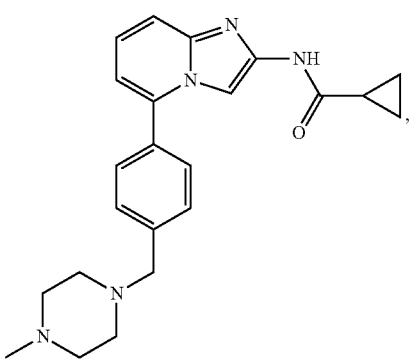
2,

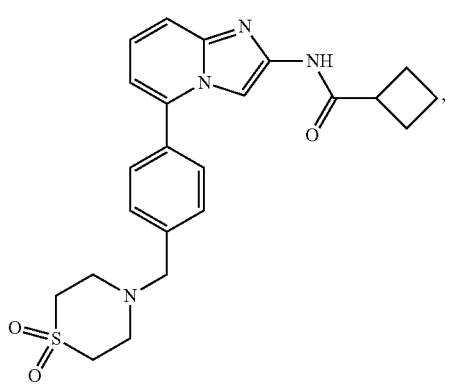
3,

-continued

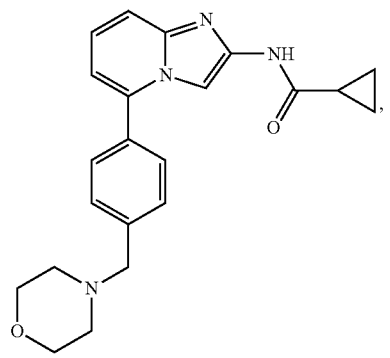
4,

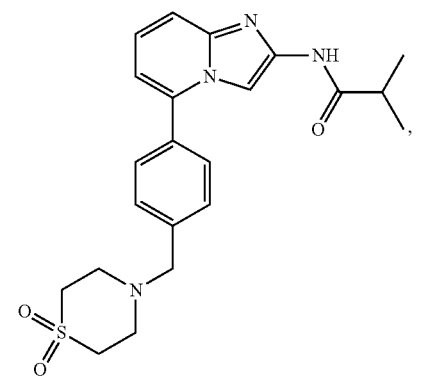
5,

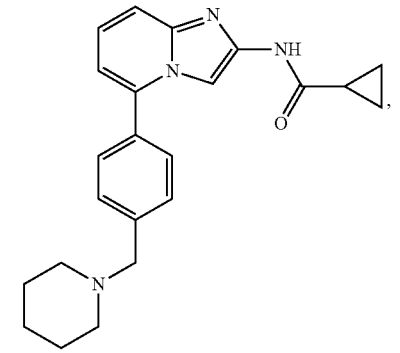
6,

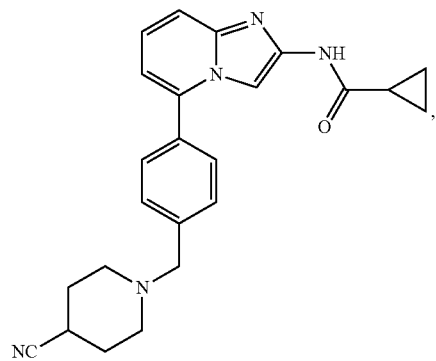
7,

115
-continued
8
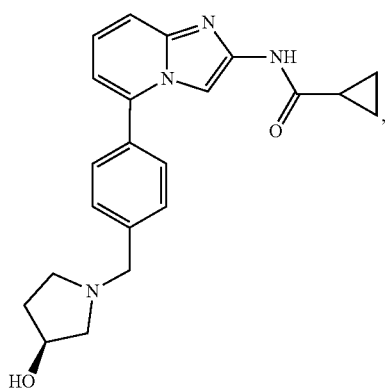
9
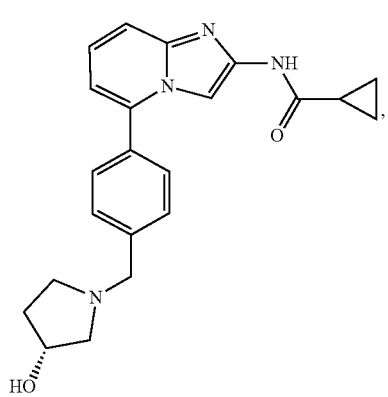
10
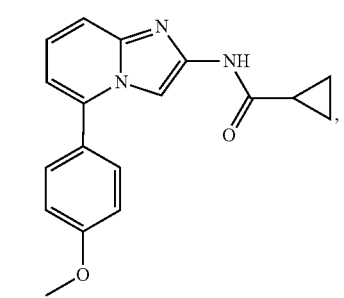
11
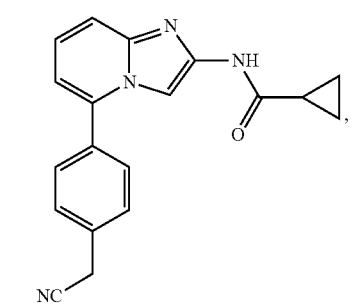
116
-continued
12
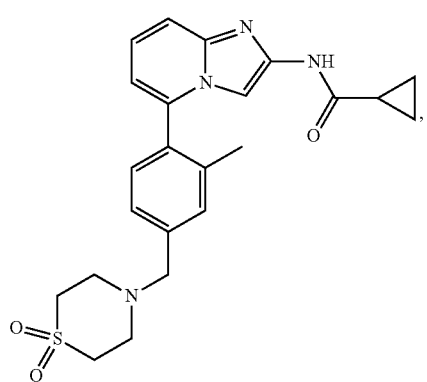
13
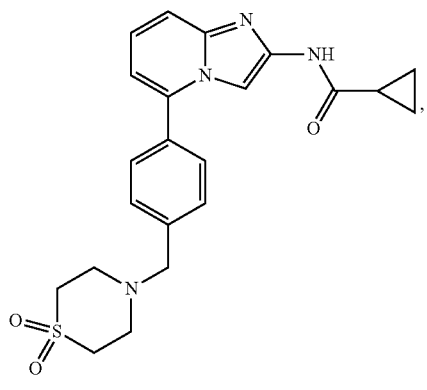
14
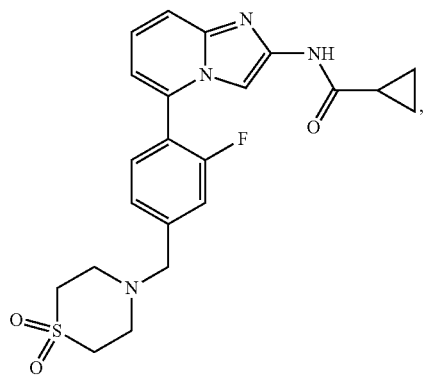
15
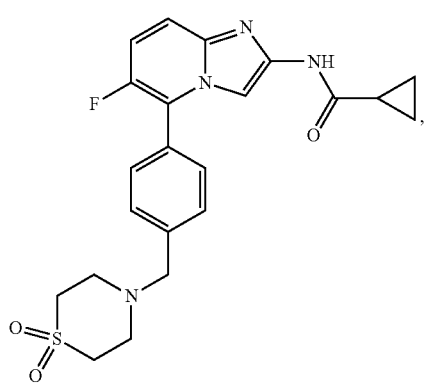

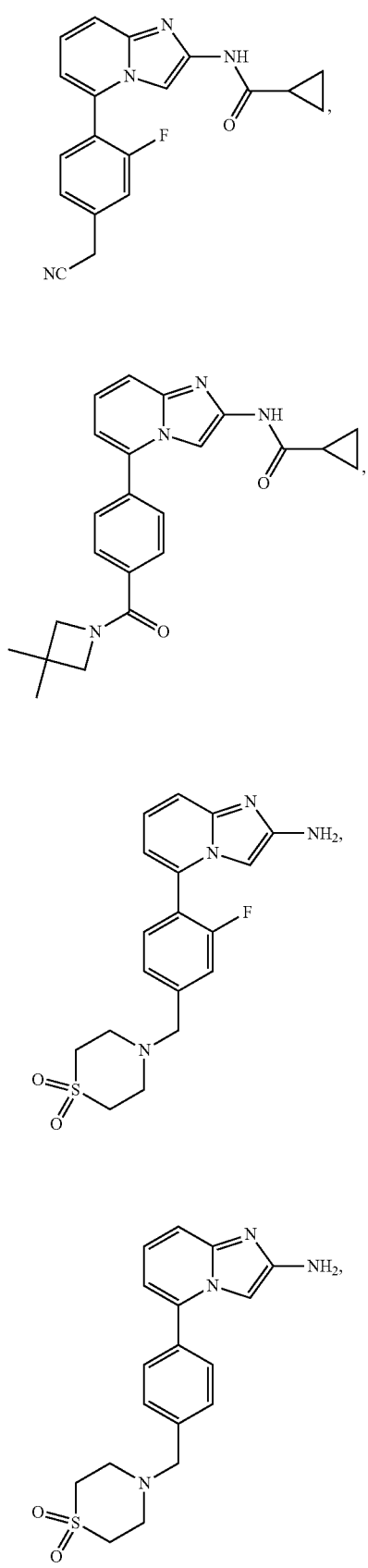
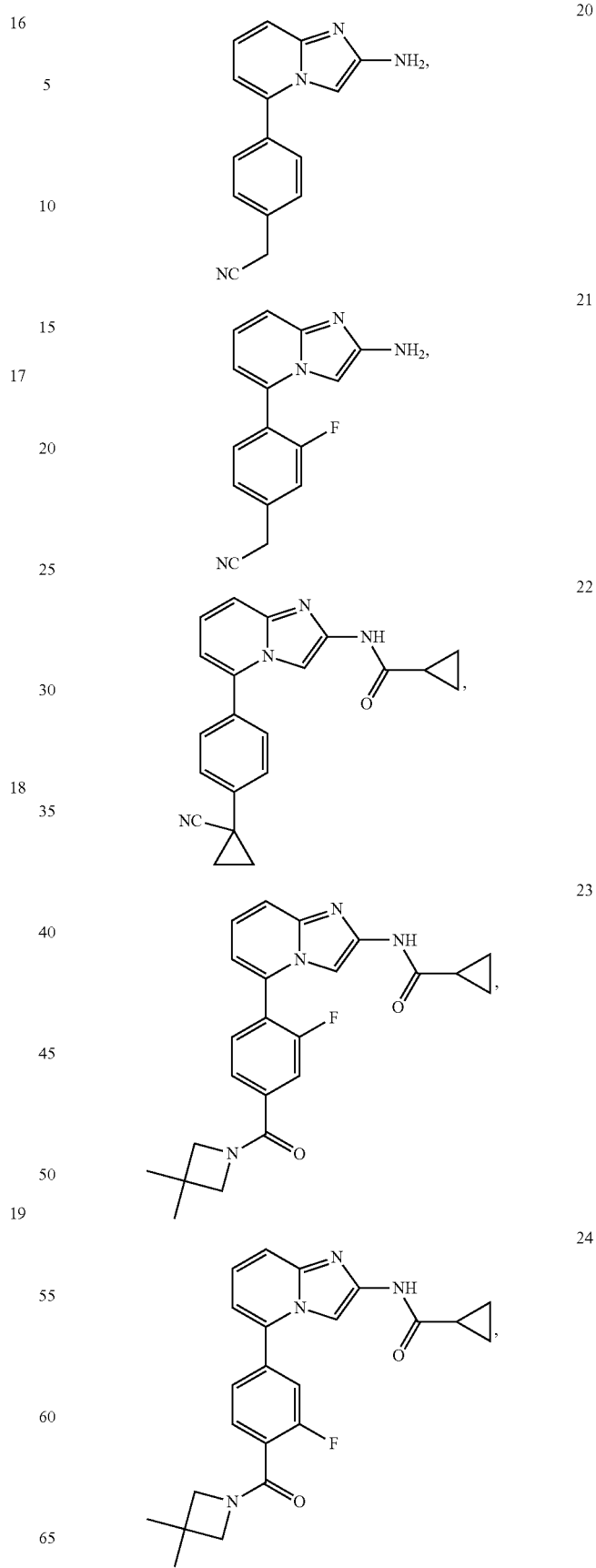

25
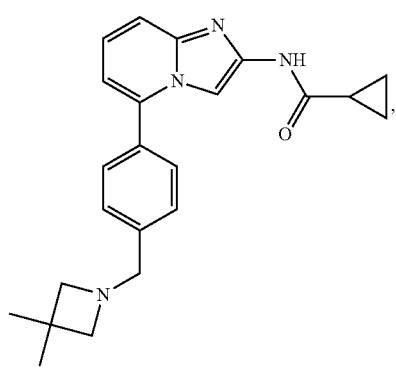
26
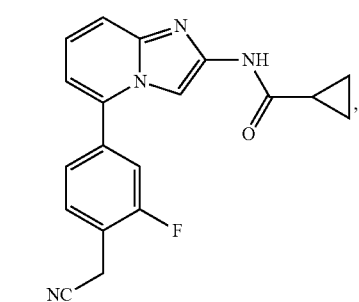
27
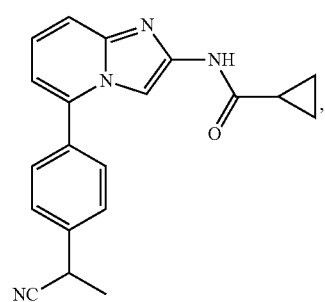
28
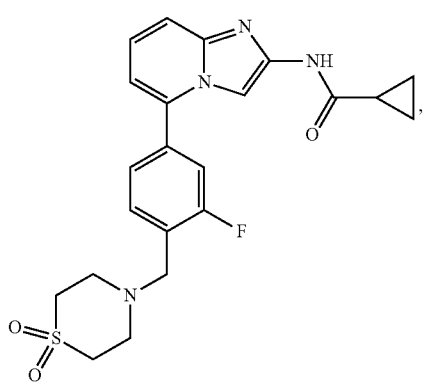
29
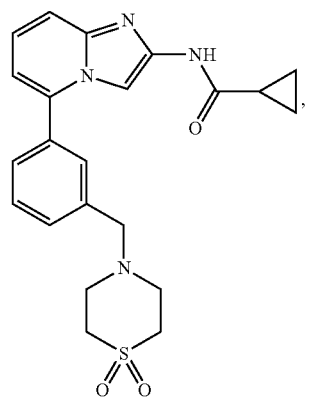
30
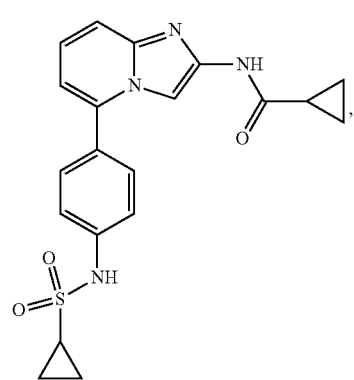
31
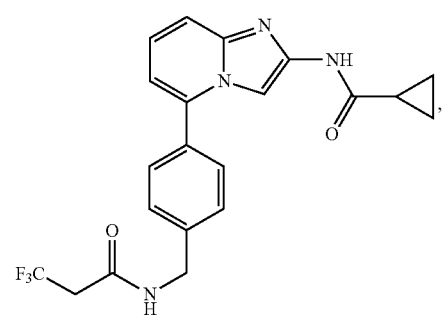
32
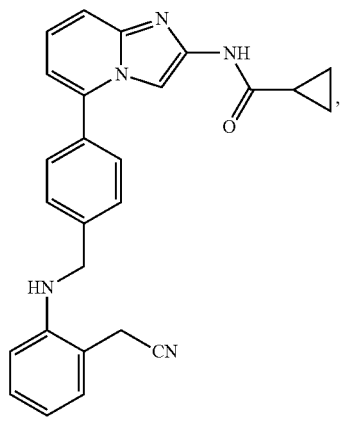

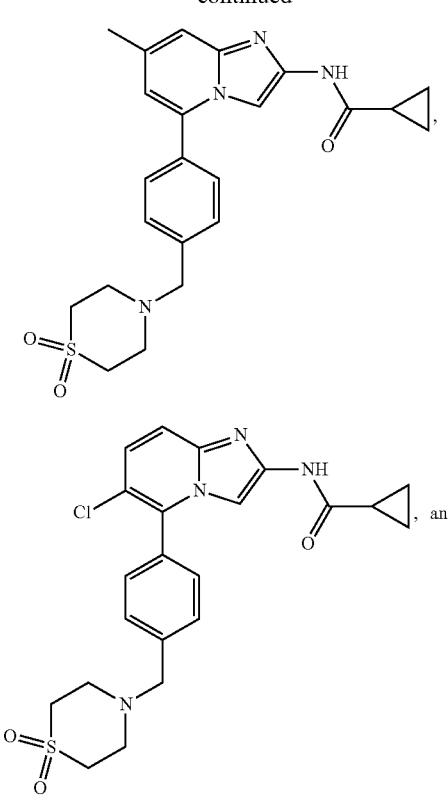
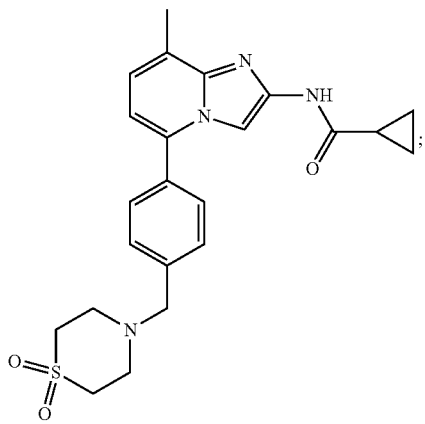
and isotopic variants thereof; and pharmaceutically acceptable salts and solvates thereof.
20. A pharmaceutical composition comprising the compound of claim 1 and a pharmaceutically acceptable excipient.
* * * * *